US012576142B2

(12) United States Patent
Bhoumik et al.

(10) Patent No.: US 12,576,142 B2
(45) Date of Patent: Mar. 17, 2026

(54) UNIVERSAL DONOR CELLS AND RELATED METHODS

(71) Applicant: ViaCyte, Inc., San Diego, CA (US)

(72) Inventors: Anindita Bhoumik, San Diego, CA (US); Alan D. Agulnick, San Diego, CA (US); Kevin Allen D'Amour, San Diego, CA (US)

(73) Assignee: ViaCyte, Inc., San Diego, CA (US)

( * ) Notice: Subject to any disclaimer, the term of this patent is extended or adjusted under 35 U.S.C. 154(b) by 264 days.

(21) Appl. No.: 18/472,072

(22) Filed: Sep. 21, 2023

(65) Prior Publication Data

US 2024/0165212 A1 May 23, 2024

Related U.S. Application Data

(62) Division of application No. 16/403,446, filed on May 3, 2019, now Pat. No. 11,904,001, which is a division of application No. 15/648,337, filed on Jul. 12, 2017, now Pat. No. 10,391,156.

(51) Int. Cl.
| | |
|---|---|
| *A61K 35/39* | (2015.01) |
| *A61K 39/00* | (2006.01) |
| *A61K 48/00* | (2006.01) |
| *C12N 5/071* | (2010.01) |
| *C12N 5/0735* | (2010.01) |
| *C12N 5/074* | (2010.01) |

(52) U.S. Cl.
CPC ............ *A61K 39/001* (2013.01); *A61K 35/39* (2013.01); *A61K 48/00* (2013.01); *C12N 5/0606* (2013.01); *C12N 5/0676* (2013.01); *C12N 5/0696* (2013.01); *C12N 2501/24* (2013.01); *C12N 2501/50* (2013.01); *C12N 2501/599* (2013.01); *C12N 2501/998* (2013.01); *C12N 2506/02* (2013.01); *C12N 2510/00* (2013.01)

(58) Field of Classification Search
CPC ...................................................... A61K 35/39
See application file for complete search history.

(56) References Cited

U.S. PATENT DOCUMENTS

| | | | |
|---|---|---|---|
| 5,011,494 | A | 4/1991 | Recum et al. |
| 5,100,392 | A | 3/1992 | Orth et al. |
| 5,219,361 | A | 6/1993 | Recum et al. |
| 5,314,471 | A | 5/1994 | Brauker et al. |
| 5,324,518 | A | 6/1994 | Orth et al. |
| 5,344,454 | A | 9/1994 | Clarke et al. |
| 5,421,923 | A | 6/1995 | Clarke et al. |
| 5,453,278 | A | 9/1995 | Chan et al. |
| 5,545,223 | A | 8/1996 | Neuenfeldt et al. |
| 5,549,675 | A | 8/1996 | Neuenfeldt et al. |
| 5,569,462 | A | 10/1996 | Martinson et al. |
| 5,593,440 | A | 1/1997 | Brauker et al. |
| 5,653,756 | A | 8/1997 | Clarke et al. |
| 5,713,888 | A | 2/1998 | Neuenfeldt et al. |
| 5,733,336 | A | 3/1998 | Neuenfeldt et al. |
| 5,741,330 | A | 4/1998 | Brauker et al. |
| 5,782,912 | A | 7/1998 | Brauker et al. |
| 5,800,529 | A | 9/1998 | Brauker et al. |
| 5,807,406 | A | 9/1998 | Brauker et al. |
| 5,882,354 | A | 3/1999 | Brauker et al. |
| 5,964,261 | A | 10/1999 | Neuenfeldt et al. |
| 5,964,804 | A | 10/1999 | Brauker et al. |
| 6,060,640 | A | 5/2000 | Pauley et al. |
| 6,156,305 | A | 12/2000 | Brauker et al. |
| 6,773,458 | B1 | 8/2004 | Brauker et al. |
| 7,432,104 | B2 | 10/2008 | Mitalipova et al. |
| 7,510,876 | B2 | 3/2009 | D'Amour et al. |
| 7,541,185 | B2 | 6/2009 | D'Amour et al. |
| 7,695,963 | B2 | 4/2010 | Agulnick et al. |
| 7,695,965 | B2 | 4/2010 | Martinson et al. |
| 7,964,402 | B2 | 6/2011 | Terskikh et al. |
| 7,985,585 | B2 | 7/2011 | D'Amour et al. |
| 8,008,075 | B2 | 8/2011 | Green et al. |
| 8,129,182 | B2 | 3/2012 | D'Amour et al. |
| 8,153,429 | B2 | 4/2012 | Robins et al. |
| 8,187,878 | B2 | 5/2012 | Dalton et al. |
| 8,211,699 | B2 | 7/2012 | Robins et al. |
| 8,278,106 | B2 | 10/2012 | Martinson et al. |

(Continued)

FOREIGN PATENT DOCUMENTS

| | | |
|---|---|---|
| EP | 2482761 A1 | 8/2012 |
| KR | 10-2016-0145186 A | 12/2016 |

(Continued)

OTHER PUBLICATIONS

2006, Gillespie KM, CMAJ, vol. 175(2), pp. 165-170. (Year: 2006).*
2005, Sjoholm et al., Diabetes/Metabolism Res. and Rev., vol. 22, pp. 4-10 (Year: 2005).*
Borisov et al., "Stem Cells in the Treatment of Insulin-Dependent Diabetes Mellitus," *Acta Naturae* 8(3):34-48, 2016.
Bottino et al., "Cellular ligands of activating NK receptors," *Trends Immunology* 26(4):221-226, 2005.
Chimienti, R. et al., "Engineering of immune checkpoints B7-H3 and CD155 enhances immune compatibility of MHC-I−/−iPSCs for beta cell replacement," *Cell Reports* 40(13): 111423, 26 pages, Sep. 2022.
Garrido F. et al., "Generation of MHC class I diversity in primary tumors and selection of the malignant phenotype," *International Journal of Cancer* 138:271-280, 2016.

(Continued)

*Primary Examiner* — Anoop K Singh
*Assistant Examiner* — David A Montanari
(74) *Attorney, Agent, or Firm* — Klarquist Sparkman, LLP; Susan Alpert Siegel; Sheree Lynn Rybak

(57) ABSTRACT

Disclosed herein are universal donor stem cells and cells derived therefrom and related methods of their use and production. The universal donor stem cells disclosed herein are useful for overcoming allogeneic immune rejection in cell-based transplantation therapies. In certain embodiments, the universal donor cells disclosed herein are pancreatic endoderm cells that do not express one or more MHC-Class I cell-surface proteins and whose expression of at least one NK activating ligand is disrupted or inhibited.

13 Claims, 21 Drawing Sheets

Specification includes a Sequence Listing.

(56) References Cited

U.S. PATENT DOCUMENTS

| | | |
|---|---|---|
| 8,334,138 B2 | 12/2012 | Robins et al. |
| 8,338,170 B2 | 12/2012 | Kelly et al. |
| 8,586,357 B2 | 11/2013 | D'Amour et al. |
| 8,633,024 B2 | 1/2014 | D'Amour et al. |
| 8,685,726 B2 | 4/2014 | Schulz et al. |
| 8,859,286 B2 | 10/2014 | Agulnick |
| 8,895,300 B2 | 11/2014 | Schulz |
| 9,109,245 B2 | 8/2015 | Agulnick et al. |
| 9,365,830 B2 | 6/2016 | Schulz et al. |
| 9,526,880 B2 | 12/2016 | So et al. |
| 10,391,156 B2 | 8/2019 | Bhoumik |
| 11,904,001 B2 | 2/2024 | Bhoumik |
| 2005/0266554 A1 | 12/2005 | D'Amour et al. |
| 2006/0222633 A1 | 10/2006 | Shlomchik et al. |
| 2007/0122905 A1 | 5/2007 | D'Amour et al. |
| 2009/0170198 A1 | 7/2009 | Rezania |
| 2009/0269845 A1 | 10/2009 | Rezania |
| 2010/0015100 A1 | 1/2010 | Xu |
| 2010/0112692 A1 | 5/2010 | Rezania |
| 2010/0112693 A1 | 5/2010 | Rezania et al. |
| 2010/0233755 A1 | 9/2010 | D'Amour et al. |
| 2010/0272695 A1 | 10/2010 | Agulnick et al. |
| 2011/0014702 A1 | 1/2011 | Xu |
| 2011/0014703 A1 | 1/2011 | Xu et al. |
| 2011/0151560 A1 | 6/2011 | Cu |
| 2011/0151561 A1 | 6/2011 | Davis et al. |
| 2012/0020938 A1 | 1/2012 | Hyde et al. |
| 2012/0052576 A1 | 3/2012 | Rezania |
| 2013/0330823 A1 | 12/2013 | Rezania |
| 2014/0134195 A1 | 5/2014 | Russell |
| 2014/0186953 A1 | 7/2014 | Rezania |
| 2014/0242693 A1 | 8/2014 | Fryer et al. |
| 2014/0295552 A1 | 10/2014 | Fryer et al. |
| 2015/0329828 A1 | 11/2015 | Rezania |
| 2016/0215268 A1 | 7/2016 | Fryer et al. |
| 2017/0029778 A1 | 2/2017 | Peterson et al. |

FOREIGN PATENT DOCUMENTS

| | | |
|---|---|---|
| RU | 2579278 C2 | 4/2016 |
| WO | 9204033 A1 | 3/1992 |
| WO | 1992004033 A1 | 3/1992 |
| WO | WO 2011/011300 A2 | 1/2011 |
| WO | WO 2011/041240 A1 | 4/2011 |
| WO | 2012115619 A1 | 8/2012 |
| WO | 2012145384 A1 | 10/2012 |
| WO | 2013192005 A2 | 12/2013 |
| WO | 2015065524 A2 | 5/2015 |
| WO | WO 2015/164740 A1 | 10/2015 |
| WO | 2016094679 A1 | 6/2016 |
| WO | 2016183041 A2 | 11/2016 |

OTHER PUBLICATIONS

Hartung, "Perspectives on In Vitro to In Vivo Extrapolations," *Applied in Vitro Toxicology* 4(4):305-316, 2018.

Ingulli, "Mechanism of cellular rejection in transplantation," *Pediatric Nephrology* 25(1):61-74, 2010.

Kang et al., "Significant impairment in immune recovery after cancer treatment," *Nursing Research* 58(2):105-114, 2009.

Khan et al., "Immunosuppressive drug therapy—biopharmaceutical challenges and remedies," *Expert Opinion Drug Delivery* 12(8):1333-1349, 2015.

Kirchberger et al., "Modulation of the immune system by human rhinoviruses," *International Archives Allergy Immunology* 142(1):1-10, 2006.

Manilay et al., "Natural killer cells and their role in graft rejection," *Current Opinion in Immunology* 10(5):532-539, 1998.

Matsuno et al., "Effect of cell seeding methods on the distribution of cells into the gelatin hydrogel nonwoven fabric," *Regenerative Therapy* 14:160-164, 2020.

Mattes, "In vitro to in vivo translation," *Current Opinion in Toxicology* 23-24:114-118, 2020.

Milner et al., "The impact of obesity on the immune response to infection," *Proceedings of the Nutritional Society* 71(2):298-306, 2012.

Pepper et al., "Posttransplant Characterization of Long-term Functional hESC-Derived Pancreatic Endoderm Grafts," *Diabetes* 68(5):953-962, 2019.

Russ et al., "Controlled induction of human pancreatic progenitors produces functional beta-like cells in vitro," *EMBO Journal* 34(13):1759-1772, 2015.

Singha et al., "Tumor-Associated Hyaluronan Limits Efficacy of Monoclonal Antibody Therapy," *Molecular Cancer Therapy* 14(2):523-53, E-PUB Dec. 15, 2014.

Siu et al., "T cell Allorecognition Pathways in Solid Organ Transplantation," *Frontiers in Immunology* 9:2548, 2018.

Unger et al., "Growth of human cells on a non-woven silk fibroin net: a potential for use in tissue engineering," *Biomaterials* 25(6):1069-1075, 2004.

Agulnick, Alan D. et al., Insulin-Producing Endocrine Cells Differentiated in Vitro from Human Embryonic Stem Cells Function in Macroencapsulation Devices in Vivo, Stem Cells Translational Medicine, 2015; 4: 1214-1222.

Aquino-Lopez, Arianexys et al., Interferon Gamma Induces Changes in Natural Killer (NK) Cell Ligand Expression and Alters NK Cell-Mediated Lysis of Pediatric Cancer Cell Lines; Frontiers in Immunology, Apr. 2017; vol. 8, Article 391.

Bonini, Chiara et al., HSV-TK Gene Transfer into Donor Lymphocytes for Control of Allogeneic Graft-Versus-Leukemia, Science, vol. 276; Jun. 13, 1997.

Bordignon, Claudio et al., Transfer of the HSV-tk Gene into Donor Peripheral Blood Lymphocytes for In Vivo Modulation of Donor Anti-Tumor Immunity after Allogeneic Bone Marrow Transplantation, Human Gene Therapy, 6:813-819 (Jun. 1995).

Braun, Robert E., et al., Infertility in Male Transgenic Mice: Disruption of Sperm Development by HSV-tk Expression in Postmeiotic Germ Cells, Biology of Reproduction 43, 684-693 (1990).

D'Amour, et al., "Production of Pancreatic Hormone-Expressing Endocrine Cells From Human Embryonic Stem Cells ," Nature Biotechnology 24:1392-1401,2006.

Dekelver, et al., (2010, Genome Res. vol. 20, pp. 1133-1142) Year 2010.

Hanna, Jacob H., et al., Pluripotency and Cellular Reprogramming: Fact, Hypotheses, Unresolved Issues, Cell, 143, Nov. 12, 2010.

Howard, et al., (2014, J. Surgical Res., vol. 187, pp. 19-23) Year 2014.

International Search Report and Written Opinion from PCT application No. PCT/US2018/041648, 11 pages (May 7, 2019).

Isobe, et al., Specific Acceptance of Cardiac Allograft After Treatment With Antibodies to ICAM-1 and LFA-1, 255 Science 1125-1127 (Feb. 1992).

Karabekian, Z, et al., HLA Class I Depleted hESC as a Source of Hypoimmunogenic Cells for Tissue Engineering Applications, Tissue Eng. Part A, 2015, vol. 21, No. 19-20, pp. 2559-2571. See abstract: pp. 2560, 2562; figure 7.

Knoepfler, Paul S., et al., Deconstructing Stem Cell Tumorigenicity: A Roadmap to Safe Regenerative Medicine, Stem Cells, 2009, 27:1050-1056.

Minasi, Lori-Ann, et al., The Selective Ablation of Interleukin 2-producing Cells Isolated from Tansgenic Mice, J. Exp. Med., The Rockefeller University Press, vol. 177, May 1993, 1451-1459.

Parham, Peter, et al., MHC Class I Molecules and KIRS in Human History, Health and Survival, Nature Reviews/Immunology, vol. 5, Mar. 2005, 201-214.

PCT application No. PCT/US2016/061442, PDX1 Pancreatic Endoderm Cells in Cell Delivery Devices and Methods Thereof, filed Nov. 10, 2016.

Pegram, Hollie, et al., Activating and Inhibitory receptors of natural killer cells, Immunology and Cell Biology (2011), 89, 216-224.

Schuldiner et al., (2003, Stem Cells, vol. 21, pp. 257-265) Year 2003.

Schulz, Thomas, et al., "A Scalable System for Production of Functional Pancreatic Progenitors from Human Embryonic Stem Cells", PLOS ONE, vol. 7, Issue 5, e37004, (1-17) (May 2012).

(56) References Cited

OTHER PUBLICATIONS

Takahashi et al., "Induction of pluripotent stem cells from mouse embryonic and adult fibroblast cultures by defined factors,", Cell, 2006, 126(4):663-76.

Takahashi et al., "Induction of Pluripotent Stem Cells from Mouse Embryonic and Adult Fibroblast cultures by Defined Factors" Cell, (2006), 126:663-676.

Teunissen M., (1992, J. Investigative Dermatology, vol. 99(5), pp. 77S-79S). Year 1992.

U.S. Appl. No. 11/993,399, Embryonic Stem Cell Culture Compositions and Methods Thereof, filed Jun. 20, 2006, now abandoned.

U.S. Appl. No. 12/099,759 entitled Methods of Producing Pancreatic Hormones, filed Apr. 8, 2008.

Zeng, Y. et al., Inhibition of Transplant Rejection by Pretreatment of Xenogeneic Pancreatic Islet Cells With ANTI-ICAM-1 Antibodies, Transplantation, Sep. 27, 1994, vol. 58, No. 6, pp. 681-689, See abstract: pp. 682-683; figure 1.

Vertex Pharmaceuticals Incorporated, "Vertex to acquire ViaCyte, with the goal of accelerating its potentially curative VX-880 programs in Type 1 Diabetes," Press Release (Jul. 11, 2022) (2 pages).

Fiorina et al., "Immunological Applications of Stem Cells in Type 1 Diabetes," *Endocrine Reviews* 32(6):725-754, E-pub Aug. 23, 2011.

Riolobos et al., "HLA Engineering of Human Pluripotent Stem Cells," *Molecular Therapy* 21(6):1232-1241, E-pub Apr. 30, 2013.

Thakur et al., "Retroviral expression of MIR2 decreases both surface MHC class I and the alloimmune CTL response," *Journal of Tissue Engineering and Regenerative Medicine* 5(7):520-528, E-pub Jan. 10, 2011.

* cited by examiner

| Sample ID | Sample | Antibody | MFI |
|---|---|---|---|
| A | WT ESC with IFNγ | B2M-PE | 182387 |
| B | WT ESC | B2M-PE | 69974 |
| C | WT ESC | Unstained-PE | 419 |

| Sample ID | Sample | Antibody | MFI |
|---|---|---|---|
| A | B2M-/- ESC with IFNγ | B2M-PE | 1559 |
| B | B2M-/- ESC | B2M-PE | 1604 |
| C | B2M-/- ESC | Unstained-PE | 1044 |

| Sample ID | Sample | Antibody | MFI |
|---|---|---|---|
| A | WT ESC with IFNγ | HLA-ABC-AF488 | 35549 |
| B | WT ESC | HLA-ABC-AF488 | 14243 |
| C | WT ESC | Unstained-AF488 | 869 |

| Sample ID | Sample | Antibody | MFI |
|---|---|---|---|
| A | B2M-/- ESC with IFNγ | HLA-ABC-AF488 | 2158 |
| B | B2M-/- ESC | HLA-ABC-AF488 | 2057 |
| C | B2M-/- ESC | Unstained-AF488 | 2017 |

| Sample ID | Sample | Antibody | MFI |
|---|---|---|---|
| A | WT PEC with IFNγ | B2M-PE | 1894 |
| B | WT PEC | B2M-PE | 25 |
| C | WT PEC | Unstained-PE | 4 |

| Sample ID | Sample | Antibody | MFI |
|-----------|--------|----------|-----|
| A | B2M-/- PEC with IFNγ | B2M-PE | 3.89 |
| B | B2M-/- PEC | B2M-PE | 3.82 |
| C | B2M-/- PEC | Unstained-PE | 3.62 |

| Sample ID | Sample | Antibody | MFI |
|---|---|---|---|
| A | WT PEC with IFNγ | HLA-ABC-AF488 | 667 |
| B | WT PEC | HLA-ABC-AF488 | 10.8 |
| C | WT PEC | Unstained-AF488 | 4.83 |

| Sample ID | Sample | Antibody | MFI |
|---|---|---|---|
| A | B2M-/- PEC with IFNγ | HLA-ABC-AF488 | 4.49 |
| B | B2M-/- PEC | HLA-ABC-AF488 | 4.41 |
| C | B2M-/- PEC | Unstained-AF488 | 4.22 |

| Sample ID | Sample | Antibody | MFI |
|---|---|---|---|
| A | WT ESC with IFNγ | ICAM1-PE | 98,879 |
| B | WT ESC | ICAM1-PE | 4,372 |
| C | WT ESC | Unstained-PE | 428 |

| Sample ID | Sample | Antibody | MFI |
|---|---|---|---|
| A | B2M-/- ESC with IFNγ | ICAM1-PE | 109,811 |
| B | B2M-/- ESC | ICAM1-PE | 2,321 |
| C | B2M-/- ESC | Unstained-PE | 532 |

| Sample ID | Sample | Antibody | MFI |
|---|---|---|---|
| A | WT PEC with IFNγ | ICAM1-PE | 17,662 |
| B | WT PEC | ICAM1-PE | 782 |
| C | WT PEC | Unstained-PE | 417 |

| Sample ID | Sample | Antibody | MFI |
|-----------|--------|----------|-----|
| A | B2M-/- PEC with IFNγ | ICAM1-PE | 19,501 |
| B | B2M-/- PEC | ICAM1-PE | 1230 |
| C | B2M-/- PEC | Unstained-PE | 537 |

| Sample ID | Sample | Antibody | MFI |
|---|---|---|---|
| A | WT PEC with IFNγ | CD58-PE/Cy5 | 42,524 |
| B | WT PEC | CD58-PE-Cy5 | 29,206 |
| C | WT PEC | Unstained-APC | 1141 |

| Sample ID | Sample | Antibody | MFI |
|---|---|---|---|
| A | WT PEC with IFNγ | CD155-PE | 17,879 |
| B | WT PEC | CD155-PE | 20,680 |
| C | WT PEC | Unstained-PE | 596 |

| Sample ID | Sample | Antibody | MFI |
|---|---|---|---|
| A | WT PEC with IFNγ | CEACAM1-PE | 2760 |
| B | WT PEC | CEACAM1-PE | 1272 |
| C | WT PEC | Unstained-PE | 596 |

| Sample ID | Sample | Antibody | MFI |
|---|---|---|---|
| A | WT PEC with IFNγ | BAT3-PE | 2,292 |
| B | WT PEC | BAT3-PE | 2,554 |
| C | WT PEC | Unstained-PE | 596 |

| Sample ID | Sample | Antibody | MFI |
|---|---|---|---|
| A | WT PEC with IFNγ | CADM1-FITC | 12,447 |
| B | WT PEC | CADM1-FITC | 12,363 |
| C | WT PEC | Unstained-FITC | 596 |

| Sample ID | Sample | Antibody | MFI |
|---|---|---|---|
| A | WT PEC with IFNγ | CD112-PE | 1,928 |
| B | WT PEC | CD112-PE | 1,922 |
| C | WT PEC | Unstained-PE | 596 |

UNIVERSAL DONOR CELLS AND RELATED METHODS

CROSS REFERENCE TO RELATED APPLICATIONS

This is a divisional of U.S. patent application Ser. No. 16/403,446, filed May 3, 2019, which is a divisional of U.S. patent application Ser. No. 15/648,337, filed Jul. 12, 2017, issued as U.S. Pat. No. 10,391,156. The prior applications are incorporated by reference herein in their entirety.

FIELD

This relates to the fields of gene expression, genome engineering and gene/cell therapy.

REFERENCE TO AN ELECTRONIC SEQUENCE LISTING

The contents of the electronic sequence listing, entitled "Sequence.xml", which has a size of 12,288 bytes and a Date of Creation of Sep. 7, 2023, is herein incorporated by reference in its entirety.

BACKGROUND

Human pluripotent stem cells (hPSCs) are a useful tool to generate any adult cell type for transplantation into patients. In principle, hPSC-based cell therapies have the potential to treat most if not all degenerative illnesses, however the success of such therapies may be limited by a subject's immune response.

The immune system protects organisms from infection with layered defenses of increasing specificity. In simple terms, physical barriers prevent pathogens such as bacteria and viruses from entering the organism. If a pathogen breaches these barriers, the innate immune system provides an immediate, but non-specific response. If pathogens successfully evade the innate response, vertebrates possess a second layer of protection, the adaptive immune system, which is activated by the innate response. The adaptive immune system generates a much more specific response. Here, the immune system adapts its response during an infection to improve its recognition of the pathogen. This improved response is then retained after the pathogen has been eliminated, in the form of an immunological memory, and allows the adaptive immune system to mount faster and stronger attacks each time this pathogen is encountered The adaptive immune response is antigen-specific and requires the recognition of specific "non-self" antigens during a process called antigen presentation. Antigen specificity allows for the generation of responses that are tailored to specific pathogens or pathogen-infected cells. Interferon gamma (IFN-γ) plays an essential role in combating infectious and non-infectious diseases. The principal source of IFN-γ in the human immune response is T cells. NK cells, macrophages, and IFN-play an important role in both innate and acquired immunity.

The major histocompatibility complex (MHC) is a set of cell surface proteins essential for the regulation of the immune system. The main function of MHC molecules is to bind to antigens derived from pathogens and display them on the cell surface for recognition by the appropriate T-cells. The MHC gene family is divided into three subgroups: class I, class II, and class III. The human MHC is also called the HLA (human leukocyte antigen) complex (often just the HLA).

Natural killer (NK) cells are lymphocytes that function at the interface between innate and adaptive immunity. NK cells contribute directly to immune defense through their effector functions, such as cytotoxicity and cytokine secretion, and by regulating innate and adaptive immune responses. When a target or host cell encounters NK cells several outcomes are possible. The extent of the NK response is determined by the amount and type of activating and inhibitory receptors on the NK cells and the amount and type of activating and inhibitory ligands on the target cell. See FIG. 1. In scenario A, when target cells have no human leucocyte antigen (HLA) Class 1 and no NK activating ligands, NK cells expressing MHC-Class I inhibitory receptors and activating ligand receptors do not attack target cells (no response, or not-licensed). In scenario B, when target cells express HLA-Class I but have no activating ligands, the NK cells expressing inhibitory receptors and activating receptors cannot attack the targets. In scenario C, when target cells have downregulated HLA-Class I or no HLA-Class I and express NK activating ligands, NK cells expressing inhibitory receptors and activating receptors attack target cells. In scenario D, when target cells express both self-HLA-Class I and NK activating ligands, then the level of response by NK cells expressing inhibitory receptors and activating receptors is determined by the balance of inhibitory and activating signals to the NK cell. Haynes et al., THE IMMUNE SYSTEM IN HEALTH AND DISEASE, PART 15: Immune-Mediated, Inflammatory, and Rheumatologic Disorders, 372e Introduction to the Immune System.

Historically, efforts to overcome a host's immune response to allogenic cells focused on the adaptive immune response, that is, interfering with adhesion between T-cells and MHC-Class I antigens presented on foreign cells. As such, CRISPR and TALEN systems have been used to generate loss of function genetic modifications and thus make stem cells that do not express one or more classic MHC/HLA genes. However, these cells and cells derived therefrom are still vulnerable to the host's innate immune response (NK cells). See, e.g., Parham et al. (2005) Nat Rev Immunol.

5(3):201-214. In order to overcome the host's innate immune response, others have tried to reintroduce tolerogenic factors back into the target cell; the focus was on the "missing self." See WO2016183041A2 the disclosure of which is incorporated by reference in its entirety. Applicants surprisingly discovered that the key to evading the host's NK mediated immune response is not the "missing self" but the expression and magnitude of NK cell activating ligands on target cells.

Thus, there remains a need for compositions and methods for developing target cells that lack some or all classic HLA expression but which cells are not attacked by NK cells for lysis.

SUMMARY

Disclosed herein are strategies to overcome graft rejection, in particular, allogenic immune graft rejection in cell-based transplantation therapies by providing universal donor cell lines. In one embodiment, human pluripotent stem cells are provided that lack some or all classic HLA-Class I cell surface protein expression and NK activating ligand expression. In one embodiment, a cell derived from a human pluripotent stem cell, such as a pancreatic cell, is provided that lack some or all classic HLA-Class I cell surface protein expression and NK activating ligand expression. In one embodiment, there is provided a method of preventing cell graft rejection by providing transplanted pancreatic cells wherein at least one MHC gene, such as beta-2-microgobulin (B2M), and at least one NK activating ligand gene, such as Intercellular Adhesion Molecule 1 (ICAM-1), has been disrupted, deleted, modified, or inhibited. In another embodiment, there is provided a method of preventing cell graft rejection by providing transplanted pancreatic cells wherein the expression of at least one MHC protein such as B2M and at least one NK activating ligand protein such as ICAM-1 has been disrupted, deleted, modified, or inhibited. Disruption, deletion, modification, or inhibition of B2M, results in deficiency in all of HLA class I surface expression and function.

SEQUENCES

The nucleic and amino acid sequences listed in the accompanying sequence listing are shown using standard letter abbreviations for nucleotide bases and amino acids, as defined in 37 C.F.R. 1.822. Only one strand of each nucleic acid sequence is shown, but the complementary strand is understood as included by any reference to the displayed strand.

DETAILED DESCRIPTION

MHC-Class I molecules are one of two primary classes of major histocompatibility complex (MHC) molecules (the other being MHC-Class II). Their function is to display peptide fragments of non-self proteins from within the cell to cytotoxic T cells; this will trigger an immediate response from the immune system against a particular non-self antigen displayed with the help of an MHC-Class I protein. In humans, the HLAs corresponding to MHC-Class I are HLA-A, HLA-B, HLA-C, HLA-E, HLA-F, and HLA-G. The human HLA-E, HLA-F, and HLA-G are non-classical MHC class I molecules characterized by limited polymorphism and a lower cell surface expression than the classical paralogues (HLA-A, -B and -C). All MHC class I proteins must associate with β2-microglobulin (B2M) to produce a functional heterodimer MHC Class I protein complex prior to functional expression on the cell surface. MHC-Class I molecules can also serve as an inhibitory ligand for NK cells. Reduction in the normal levels of cell surface MHC-Class I, activates NK cell killing.

Figure 1:
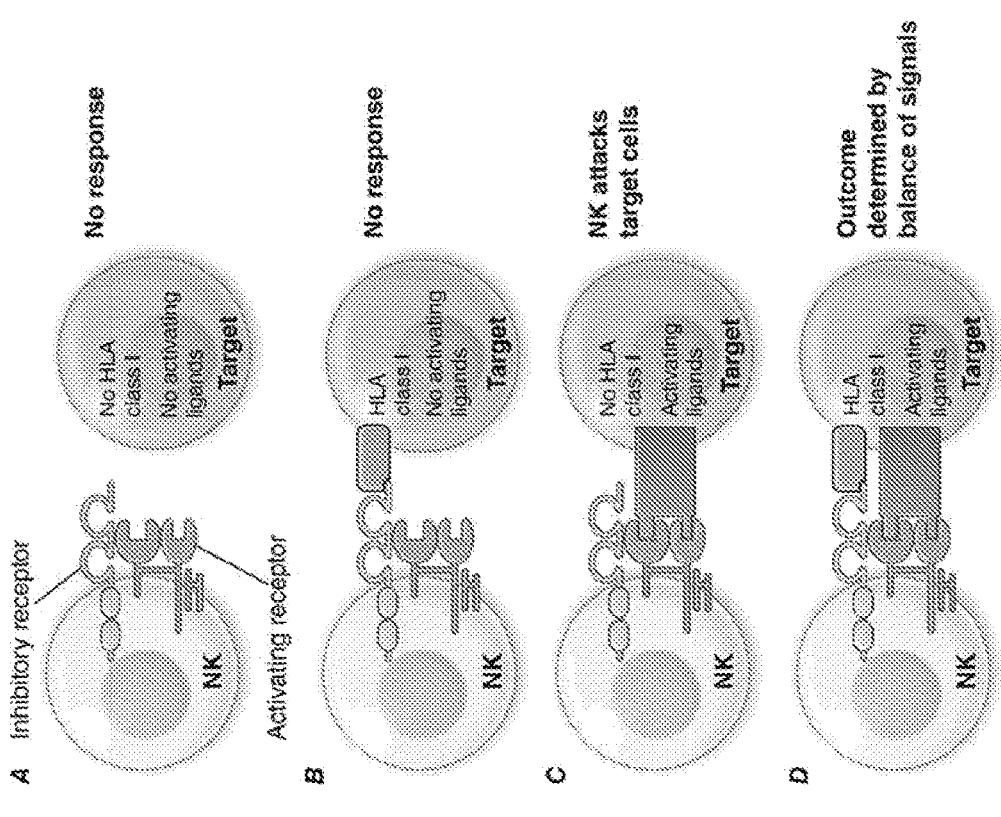
FIG. 1 is a reproduction from Haynes et al., supra, (which is incorporated herein in its entirety) showing different scenarios (A of NK mediated response to target cells. In the absence of MHC-Class I and absence of NK activating ligands on the target cell, inhibitory and activating receptors on NK cells are not engaged and NK cells remain unresponsive (Scenario A). In the presence of MHC Class I, but in the absence of NK activating ligands on the target cell, inhibitory receptors on NK cells are engaged but activating receptors on NK cells are not engaged and NK cells remain unresponsive (Scenario B). In the absence of self-MHC-Class I but in the presence of NK activating ligands on the target cell, inhibitory receptors on NK cells are not engaged but activating receptors on NK cells are engaged and NK cells attack (Scenario C). In the presence of MHC-Class I and NK activating ligands on the target cell, inhibitory and activating receptors on NK cells are engaged and the outcome is determined by a balance of signals (Scenario D).

Historically, it was believed that target cells bearing MHC-Class I inhibitory ligands evade attack when exposed to NK cells because of the assumed dominate nature of the MHC-Class I's inhibitory signal (see FIG. 1 scenario B reproduced from Harrison's Principles of Internal Medicine 19 E (Vol. 1 and Vol. 2) A Major Histocompatibility Complex, Part 15, FIG. 372e-4 therein). But, Applicants surprisingly found the opposite to be true.

Figure 15:
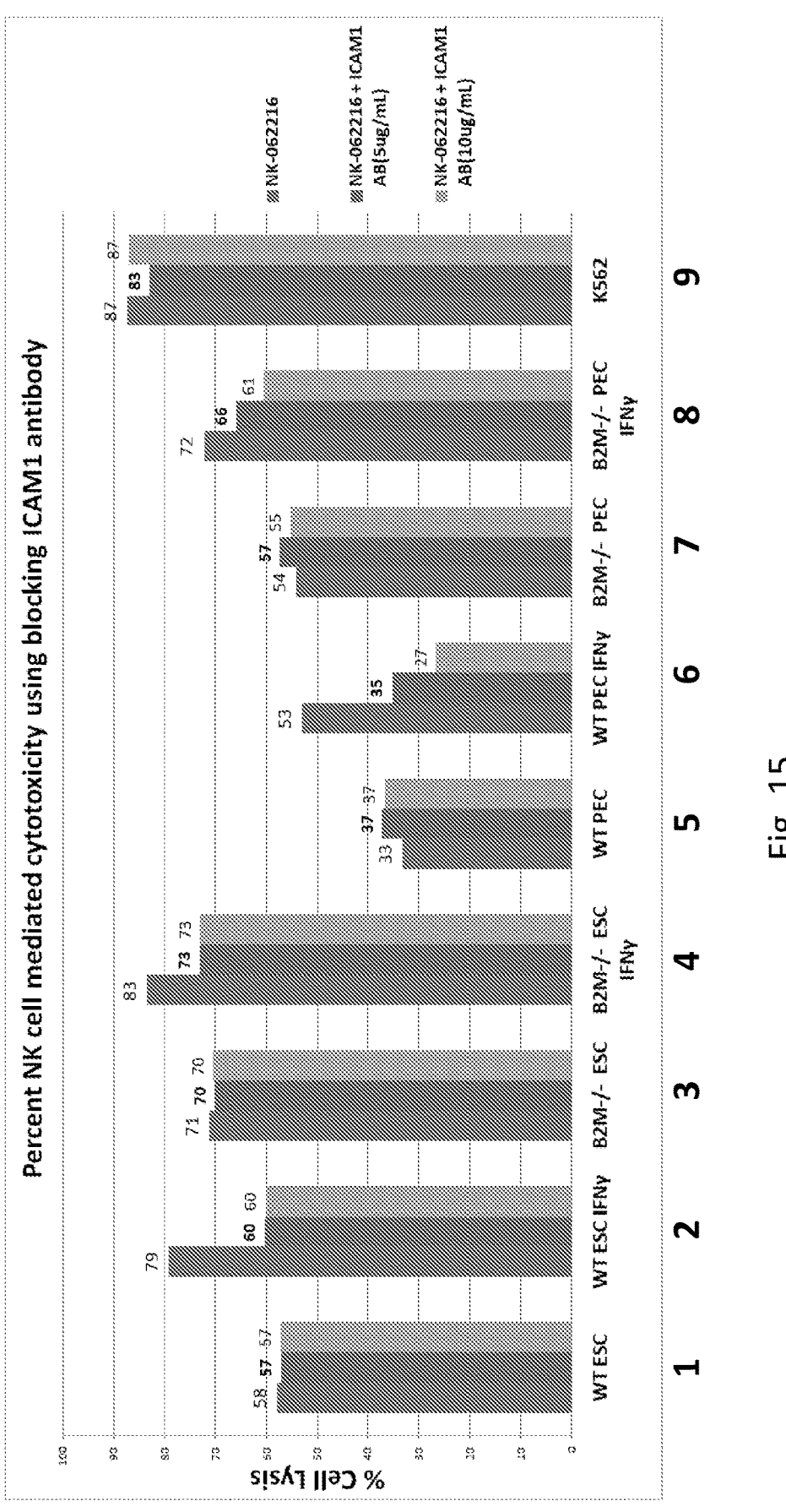
FIG. 15 is a bar graph showing a reduction in NK cell lysis of target cells after blocking ICAM-1 expression in the target cell with an anti-ICAM1 antibody (left to right, WT hESC, WT hESC exposed to IFN-γ, B2M–/– hESC, B2M–/– hES exposed to IFN-γ, WT PEC, WT PEC exposed to IFN-γ, B2M–/– PEC, B2M–/– PEC exposed to IFN-γ, K562-control cell line for the NK cytotoxicity assay).

It has been shown that exposure of cells to IFN-γ increases mRNA expression of MHC-Class I molecules and also MHC Class I protein complex expression on the cell surface. It is expected that this increase in MHC-Class I expression inhibits NK cells. Applicants discovered that wild type (WT) hES cells when exposed to IFN-γ (which has been shown to increase MHC-Class I molecules on the cell surface of hES cells, FIG. 2A and 3A) have increased NK cell-mediated cytotoxicity. See FIG. 15 showing NK cell mediated toxicity (lysis) increases from 58% to 79% (compare first bars in condition 1 and 2 in FIG. 15). The same was true when WT PEC cells were exposed to IFN-γ, the cells also had increased B2M and HLA-ABC expression, see FIG. 4A and 5A and NK mediated toxicity (lysis) increased from 33% to 53% (compare first bars in conditions 5 and 6 in FIG. 15). This data suggested that the key to overcoming a host's NK cell immune response is not in overexpressing inhibitory MHC-Class I signals but in blocking NK activating ligand signals.

To further test this hypothesis in the context of accentuated NK cell-mediated cytotoxicity, Applicants made a B2M–/– (knockout) hES cell (similar to FIG.1 scenario C). As expected, B2M–/– eliminated cell surface expression of MHC Class I molecules on hES cells (FIGS. 2B and 3B) and PEC (FIGS. 4B and 5B). Also as expected, the B2M–/– cells exhibited increased NK cell-mediated lysis relative to the WT cells, 58% to 71% for hES cells and 33% to 54% for PEC (compare first bars in condition 1 vs. 3 or 5 vs. 7 in FIG. 15). Applicants discovered that exposure of B2M–/– hES cells or PEC to IFN-γ further increased the percentage of NK cell mediated toxicity (lysis) (compare first bars in condition 2 vs. 4 and 6 vs. 8 in FIG. 15). Correspondingly. Applicants discovered that NK cell activating ligand cell surface expression (FIGS. 6B and 7B), and mRNA expression (FIG. 8) is increased under exposure to IFN-γ. This data suggested that NK cell activating ligands on the target cell play a critical role in the cytotoxicity of NK cells and led to the hypothesis that inhibiting NK cell activating ligand expression could protect against NK cell mediated cytotoxicity in the context of reduced MCH Class I expression, for example in the context of B2M–/–.

To determine whether NK cell toxicity may be reduced by inhibiting the effect of the NK activating ligands on target cells, Applicants blocked the expression of NK activating ligand in WT and B2M–/– hES cells and PEC, for example, using an ICAM1 blocking antibody to block ICAM1 protein on the target cell surface. The Applicants surprisingly discovered that cell lysis of target cells was reduced (compare first bars to 2nd and third bars for conditions 2, 4, 6 and 8 in FIG. 15). Thus, Applicants discovered that cell lysis by NK cells can be reduced by blocking an NK activating ligand. Blocking ICAM1 expression using an antibody against an NK activating ligand in B2M–/– cells is the proof of concept for producing a cell having a double knockout (HLA-Class I gene knockout and NK activating ligand gene knockout). In doing so, Applicants can transition target cells (e.g. hES and/or pancreatic lineage cells) from scenario C to A in FIG. 1. Specifically, the cells, tissues and organs of the invention have inhibited or no HLA-Class I cell surface protein expression (B2M–/–) and inhibited or no NK activating ligand cell surface protein expression (e.g., ICAM1–/–). Inhibiting cell surface protein expression can be achieved by knocking out the gene or blocking expression of the protein using an antibody. Other strategies for interfering with cell surface protein expression include using anti-sense RNA, RNA decoys, ribozymes, RNA aptamers, siRNA, shRNA/miRNA, Transdominant negative proteins (TNPs), chimeric/fusion proteins, Nucleases, Chemokine ligands, Anti-infectious cellular proteins, Intracellular antibodies (sFvs), Nucleoside analogues (NRTIs), non-nucleoside analogues (NNRTIs), Integrase inhibitors (Oligonucleotides, dinucleotides and chemical agents), and protease inhibitors. A double or multiple gene knockout would effectively prevent both cytotoxic T cell (CTL) mediated and NK cell mediated toxicity because there would be little to no HLA-Class I and little to no NK activating ligand proteins expressed on the cell surface for the CTL or NK cell to bind to. Further, in order to completely eliminate NK activation, Applicants anticipate that expression of multiple NK activating ligands will need to be eliminated/reduced either by gene knockout in the target cell (e.g. the hES cell-derived cell therapy), or by using a blocking antibody or other strategies now known or developed in the future.

NK Cell Activating Ligand Blocking Agents

According to one aspect of the invention, a method of treatment to suppress NK cell function is provided. According to another aspect of the invention, a method of treatment to suppress at least one immune response is provided. Each method involves administering to a subject in need of treatment an agent that inhibits NK cell function. In some embodiments, the agent is an antibody. In some embodiments the antibody selectively binds to a NK cell activating ligand on a target cell.

It is contemplated that reagents of various types, including antibodies and blocking proteins can be used to interfere with adhesion between NK cells and target cells' NK activating ligands.

In certain embodiments, such NK activating ligands are selected from Table 1.

TABLE 1

| Natural Killer (NK) Activating Ligands | | |
| --- | --- | --- |
| Category | GENE ID | Description |
| Category 1 Known NK activating ligands | ICAM1 | Intercellular adhesion molecule 1 |
| | CEACAM1 | Carcinoembryonic antigen-related cell adhesion molecule 1 |
| | BAG6 | Large proline-rich protein BAG6 |
| | CADM1 | Cell adhesion molecule 1 |
| | CD58 | Lymphocyte function-associated antigen 3 |
| | CD72 | B-cell differentiation antigen CD72 |
| | CD74 | |
| | HLA-E | |
| | MICA | MHC-Class I polypeptide-related sequence A |

TABLE 1-continued

| Natural Killer (NK) Activating Ligands | | |
| --- | --- | --- |
| Category | GENE ID | Description |
| | MICB | MHC-Class I polypeptide-related sequence B |
| | PVR | Poliovirus receptor |
| | PVRL2 | NECTIN2 |
| Category 2 Potential NK activating ligands identified from RNA expression array data (upregulated in PEC and/ or ESC after IFNγ) | BTN3A3 | Butyrophilin subfamily 3 member A3 |
| | CD47 | Leukocyte surface antigen CD47 |
| | CTSS | Cathepsin S |
| | NTRK2 | BDNF/NT-3 growth factors receptor |
| | RTP4 | Receptor-transporting protein 4 |
| | TLR3/CD283 | Toll-like receptor 3 |
| | TMEM140 | Transmembrane protein 140 |
| | TMPRSS3 | Transmembrane protease serine 3 |
| | BST2/CD317 | Bone marrow stromal antigen 2 |
| | BTN3A1 | Butyrophilin subfamily 3 member A1 |
| | CD40 | |
| | EPSTI1 | Epithelial-stromal interaction protein 1 |
| | ERAP1 | Endoplasmic reticulum aminopeptidase 1 |
| | ERAP2 | Endoplasmic reticulum aminopeptidase 2 |
| | GJD3 | Gap junction delta-3 protein |
| | HCP5 | HLA-Class I histocompatibility antigen protein P5 |
| | IFI6 | Interferon alpha-inducible protein 6 |
| | IFITM1 | Interferon-induced transmembrane protein 1 |
| | IFITM2 | Interferon-induced transmembrane protein 2 |
| | IFITM3 | Interferon-induced transmembrane protein 3 |
| | LGALS3BP | Galectin-3-binding protein |
| Category 3 | C1QBP | Complement component 1 Q subcomponent-binding protein, mitochondrial |
| Potential NK activating ligands identified from RNA expression array data (upregulated in ESC) | CD24 | |
| | CD55 | Complement decay-accelerating factor |
| | CD9 | Leukocyte antigen MIC3 |
| | GJA1 | Gap junction alpha-1 protein |
| | GPRC5B | G-protein coupled receptor family C group 5 member B |
| | HMMR | Hyaluronan mediated motility receptor |
| | ICAM3 | Intercellular adhesion molecule 3 |
| | IGSF5 | Immunoglobulin superfamily member 5 |
| | SYNGR3 | Synaptogyrin-3 |
| | TFRC/CD71 | Transferrin receptor protein 1 |
| | THY-1/CD90 | Thy-1 membrane glycoprotein |
| | TMEM68 | Transmembrane protein 68 |
| | TMEM97 | Transmembrane protein 97 |
| | ANKRD27 | Ankyrin repeat domain-containing protein 27 |

NK activating ligands are further described in Pegram et al., Activating and inhibitory receptors of NK cells Immunology and Cell Biology (2011) 89, 216-224 which is herein incorporated by reference in its entirety.

Hypoimmunogenic hES Cells and Cells Derived Therefrom

HLA is a cell surface molecule that is encoded by a large gene family and can be divided into class I and class II molecules. HLA-Class I molecules are found on the surface of every nucleated cell and is the focus of the invention described herein. HLA mismatch between donor (target) cells and the recipient's immune cells (e.g. T cells) during transplantation often results in immune rejection or graft rejection. HLA-Class I complexes structurally consist of a polymorphic heavy chain consisting of HLA-Class I peptides (e.g., HLA-A, HLA-B and HLA-C) and a light chain beta-2-microglobulin (B2m or B2M). In the absence of B2M, class I HLAs cannot be properly assembled and are also not expressed on the cell surface or cell membrane. In the invention described herein, Applicants produced hES cell lines and cells derived therefrom by disrupting (a few base pairs are added or removed, creating a frame shift in the mRNA/protein and a loss of function mutation) the B2M gene, and thereby depleting HLA-Class 1 expression from the cell surface in hESCs.

The above methodology can also be used to produce or generate hES cell lines and cells derived therefrom by additionally disrupting genes that encode for NK activating ligands, such as ICAM1. Thus, in one embodiment of the invention, compositions and methods are provided to make a target cell that is missing at least one HLA-Class I antigen and at least one NK activating ligand, and thereby creating a hypoimmunogenic cell. Such a hypoimmunogenic cell is expected to be less prone to immune rejection by a subject into whom such cells are transplanted. When transplanted, this hypoimmunogenic cell should engraft (not be rejected). In one embodiment, such a target cell is capable of engrafting and surviving with little to no immune suppression required of the recipient.

In one embodiment, the inhibition, reduction, and/or deletion of both HLA-Class I expression and NK activating ligand expression (or HLA-Class I deficient and NK activating ligand deficient) in hESC cells and cells derived therefrom can serve as a universal donor cell source for transplantation therapy. These double knockouts (HLA-Class I deficient and NK activating ligand deficient) can be transplanted universally without minor histocompatibility complex (MiHC) matching, human leukocyte antigen (HLA) matching or immune suppression.

Disclosed herein are novel in vitro derived hypoimmunogenic compositions and cells. Specifically, in certain embodiments, the inventions disclosed herein relate to a stem cell, the genome of which has been altered (modified) to reduce or delete critical components of both a MHC-Class I gene(s) and a NK activating ligand gene(s). In certain embodiments, the inventions disclosed herein relate to pancreatic lineage cells such as pancreatic endoderm cells, pancreatic epithelial cells, pancreatic progenitor cells, pancreatic precursor endocrine cells, pancreatic endocrine cells, pancreatic pre-beta cells, or pancreatic beta cells, the genome of which has been altered (modified) to reduce or delete critical components of both a MHC-Class I gene(s) and a NK activating ligand gene(s) thereby generating hypoimmunogenic pancreatic-lineage type cells. Natural killer activating ligands include but are not limited to the ligands listed in Table 1, from category 1, 2, 3, or combinations thereof. Natural killer activating ligands include, for example ICAM-1,CEACAMI, CADMI, MICA and MICB. MHC-Class I genes include HLA-A, HLA-B, HLA-C, HLA-E, HLA-F, HLA-G and B2M. In certain aspects, such reduced expression or knock out of the MHC-Class I and/or MHC-Class II genes is accomplished by directly and/or indirectly targeting the NLRC5, B2M and CIITA genes and other components of the MHC enhanceosome (an enhanceosome is a higher-order protein complex assembled at the enhancer and regulates expression of a target gene, e.g., transcriptional regulators of MHC-Class I or MHC-Class II).

Also disclosed herein are methods of preparing hypoimmunogenic cells, the method comprising modulating expression of one or more NK activating ligands expressed by the cell and modulating expression of one or more MHC-Class I and/or MHC-Class II by the cell, thereby preparing the hypoimmunogenic cell. In certain aspects, modulating cell surface protein expression of one or more MHC-Class I and/or MHC-Class II complexes comprises reducing, inhibiting and/or interfering with the expression of one or more MHC-Class I and/or MHC-Class II genes or proteins. In certain embodiments, modulating expression of the one or more MHC-Class I and/or MHC-Class II complexes comprises deleting one or more genes encoding one or more transcriptional regulators of MHC-Class I or MHC-Class II from at least one allele of the cell. For example, in certain embodiments such methods comprise deleting one or more genes encoding one or more of the transcriptional regulators of MHC-Class I or MHC-Class II genes selected from the group consisting of LRC5, CIITA, B2M and combinations thereof. In certain aspects, modulating expression of the one or more NK activating ligands comprises deleting, inhibiting, or reducing expression of one or more genes encoding a NK activating ligand. In certain embodiments, such NK activating ligands are selected from Table 1. In certain embodiments, such NK activating ligands are selected from Table 1, category 1, 2, 3 or combinations thereof. In certain embodiments, such NK activating ligands are selected from Table 1 category 1, 2 and 3. In certain embodiments, such NK activating ligands are selected from Table 1 category 1 and 3. In certain embodiments, such NK activating ligands are selected from Table 1 category 1 and 3. In certain embodiments, such NK activating ligands are selected from Table 1 category 1 and 2. In certain embodiments, such NK activating ligands are selected from Table 1 category 2 and 3. In certain embodiments, such NK activating ligands are selected from the group consisting of ICAM-1, CEACAMI, CADMI MICA, MICB and combinations thereof.

In certain embodiments, the implanted hypoimmunogenic cells are in a media free of animal-sourced products, e.g. xenofree products.

The present invention contemplates altering target polynucleotide sequences in any manner which is available to the skilled artisan, for example, utilizing any of zinc-finger nucleases (ZFN or ZNF), TALEN or a CRISPR/Cas systems or traditional homologous recombination techniques. Such CRISPR/Cas systems can employ a variety of Cas proteins (Haft et al. PLOS Comput Biol. 2005; 1(6)e60). In some embodiments, the CRISPR/Cas system is a CRISPR type I system. In some embodiments, the CRISPR/Cas system is a CRISPR type II system. In some embodiments, the CRISPR/Cas system is a CRISPR type V system. NEXTGEN™ CRISPR (Transposagen Inc., Lexington Kentucky), which incorporates dual guide RNA's and a catalytically inactive Cas9 protein fused to the FokI nuclease can also be used to alter a target polynucleotide sequence. Other methods of targeting polynucleotide sequences to reduce or ablate expression in target cells now known to the skilled artisan or later discovered can be utilized to generate the hypoimmunogenic cells described herein.

In some embodiments, the alteration results in reduced expression of the target polynucleotide sequence. In some embodiments, the alteration is a homozygous alteration. In some embodiments, the alteration is a heterozygous alteration.

In some embodiments, the target polynucleotide sequence is a genomic sequence. In some embodiments, the target polynucleotide sequence is a human genomic sequence. In some embodiments, the target polynucleotide sequence is a mammalian genomic sequence. In some embodiments, the target polynucleotide sequence is a vertebrate genomic sequence.

In some embodiments, the hypoimmunogenic cells are embryonic stem cells. In certain embodiments, the hypoimmunogenic cells are pluripotent stem cells. In certain embodiments, the hypoimmunogenic cells are induced pluripotent stem cells, reprogrammed cells, dedifferentiated or transdifferentiated cells. In certain embodiments, the hypoimmunogenic cells are multipotent pancreatic progenitor cells. In certain embodiments, the hypoimmunogenic cells are singly hormonal or polyhormonal cells. In certain embodiments, the hypoimmunogenic cells are mesendoderm cells, definitive endoderm cells, PDX1-negative foregut endoderm cells, PDX1-positive foregut endoderm cells, pancreatic endoderm cells, endocrine progenitor/precursor cells, endocrine cells, properly specified endocrine cells, immature endocrine cells, or functional beta-cells. In some embodiments, the hypoimmunogenic cells can be homogenous or heterogeneous cell populations. In some embodiments, the hypoimmunogenic cell are cells producing one or more biologically active substances of interest. Hypoimmunogenic cells may not initially be therapeutically active when first implanted, e.g. pancreatic progenitors or PDX1-positive pancreatic endoderm, but once transplanted they further develop and mature and have a therapeutic effect.

In some embodiments, the hypoimmunogenic cells may be any cell capable of being derived from human pluripotent stem cells including but not limited to any cell, tissue, or organ and can include skin cells, beta cells (i.e., cells in the pancreas located in the islets of Langerhans), parathyroid cells, intestinal cells, endocrine cells cardiac cells, brain cells, kidney cells, liver cells, cells of the digestive tract and accessory digestive organs, salivary gland cells, adrenal gland cells, prostate cells, lung cells, pancreatic cells, bone cells, immune cells, hematopoietic cells, vascular cells, cells of the eye, connective tissue cells, musculoskeletal cells, bone tissue, musculoskeletal tissue, cornea tissue, skin tissue, heart valves, blood vessels, immune cells, connective tissue, lung tissue, skin, a cornea, a kidney, a liver, a lung, a pancreas, a heart, and intestine.

In some embodiments, the hypoimmunogenic cell can be individual (single) cells in suspension or cell aggregates. In some embodiments, the hypoimmunogenic cells include totipotent cells. In one embodiment, the hypoimmunogenic cells include multipotent cells. In one embodiment, the hypoimmunogenic cells include unipotent cells.

In some embodiments, the hypoimmunogenic cells are derived from the pluripotent cell population lacking functional HLA-Class I expression and NK activating ligand expression. The derived cells can be selected from the group consisting of: any cell, tissue, or organ and can include skin cells, beta cells (i.e., cells in the pancreas located in the islets of Langerhans), parathyroid cells, intestinal cells, endocrine cells cardiac cells, brain cells, kidney cells, liver cells, cells of the digestive tract and accessory digestive organs, salivary gland cells, adrenal gland cells, prostate cells, lung cells, pancreatic cells, bone cells, immune cells, hematopoietic cells, vascular cells, cells of the eye, connective tissue cells, musculoskeletal cells, bone tissue, musculoskeletal tissue, cornea tissue, skin tissue, heart valves, blood vessels, immune cells, connective tissue, lung tissue, skin, a cornea, a kidney, a liver, a lung, a pancreas, a heart, and intestine.

The hypoimmunogenic cell, tissue and/or organ to be transplanted can be syngeneic or allogenic to the subject receiving the transplant.

In one embodiment the hypoimmunogenic cell is a human pluripotent cell. In one embodiment the hypoimmunogenic cell is a human pancreatic-lineage cell. In one embodiment the hypoimmunogenic cell is a human pancreatic endoderm cell. In one embodiment the hypoimmunogenic cell is a human pancreatic precursor cell. In one embodiment the hypoimmunogenic cell is a human pancreatic progenitor cell. In one embodiment the hypoimmunogenic cell is a human pancreatic endocrine cell. In one embodiment the hypoimmunogenic cell is a human pancreatic endocrine precursor cell. In one embodiment the hypoimmunogenic cell is a human pancreatic endocrine pre-beta cell. In one embodiment the hypoimmunogenic cell is a human pancreatic beta cell. In one embodiment the hypoimmunogenic cell is a human pancreatic singly hormonal or polyhormonal cell. In one embodiment the hypoimmunogenic cell is a human insulin expressing cell.

In one embodiment, the hypoimmunogenic cells are well known, publicly available pluripotent cell lines. The invention described herein is useful with all hES cell and iPSC lines, and at least hESC, e.g., CyT49, CyT25, CyT203 and CyT212. Pluripotent cell lines include those cells available for commercial purchase from WiCell on the world wide web at wicell.org/home/stem-cell-lines/order-stem-cell-lines/obtain-stem-cell-lines.cmsx and specifically include BG01, BG02, and BG03.

In one embodiment, the hypoimmunogenic cells are substantially similar to the cells described in D'Amour et al. "Production of Pancreatic Hormone-Expressing Endocrine Cells From Human Embryonic Stem Cells" (Nov. 1, 2006) Nature Biotechnology 24, 1392-1401 which is herein incorporated by reference in its entirety. D'Amour et al. describe a 5 step differentiation protocol: stage 1 (results in mostly definitive endoderm production), stage 2 (results in mostly PDX1-negative foregut endoderm production), stage 3 (results in mostly PDX1-positive foregut endoderm production), stage 4 (results in mostly pancreatic endoderm also called multipotent pancreatic progenitor or pancreatic endocrine progenitor production) and stage 5 (results in mostly hormone-expressing endocrine cell production). In one embodiment, the hypoimmunogenic cells are substantially similar to that described in U.S. Pat. Nos. 7,510,876, 7,695, 965, 7,985,585, 8,586,357, 8,633,024 and 8,129,182 (which are herein incorporated by reference in their entirety).

In one embodiment, the hypoimmunogenic cells are substantially similar to the cells described in Schulz et al. A Scalable System for Production of Functional Pancreatic Progenitors from Human Embryonic Stem Cells, PLOS One 7:5 1-17 (2012) which is herein incorporated in its entirety by reference. Schulz et. al. describe hESC expansion and banking methods and a suspension-based differentiation system. Specifically, undifferentiated pluripotent cells were aggregated into clusters in dynamic rotational suspension culture, followed by differentiation en masse for two weeks with a four-stage protocol. Briefly, from hES cell aggregate suspensions, hESC monolayers are dissociated with Accutase (Innovative Cell Technologies), collected and resuspended at 1×106 cells/mL in StemPro hESC SFM (Life Technologies; combined DMEM/F12 containing Glutamax, StemPro hESC supplement, BSA, and 1% (v/v) Penicillin/streptomycin; omitted FGF-2 and 2-Mercaptoethanol). The single cell suspensions were dispensed to non-TC treated 6-well plates (5.5 mL/well) and rotated at 95 rpm on an Innova 2000 rotator (New Brunswick Scientific), or dispensed to 500 mL Nalgene filter receiver storage bottles (150 mL/bottle) and rotated at 65 rpm on a Sartorius Certomat RM-50 rotator (configured with a 5 cm axis of rotation). Cells were rotated overnight in a 370C/8% CO2 incubator and formed aggregates of approximately 100-200 μm. For aggregate diameters between 100-200 μm rotation speeds between 60-140 rpm for a 6-well dish can be used; rotation speeds between 5-20 rpm for a 500 mL bottle can be used. Differentiation of suspension aggregates involved only a few modifications from D'Amour. The TGF-BRI kinase Inhibitor IV was included during Stage-2, and retinoic acid was replaced with a more stable retinoid analog. TTNPB (3 nM), during Stage-3. The growth factors KGF (50 ng/mL) and EGF (50 ng/mL) were added to Stage-4 to preserve cell mass. Noggin (50 ng/mL) was also included at Stage-4. In one embodiment, the hypoimmunogenic cells are substantially similar to that described in U.S. Pat. Nos. 8,008,075 and 8,895,300 (which are herein incorporated by reference in their entirety).

In one embodiment, hypoimmunogenic cells are substantially similar to the cells described in Agulnick et al. Insulin-Producing Endocrine Cells Differentiated In Vitro From Human Embryonic Stem Cells Function in Macroencapsulation Devices In Vivo Stem Cells Translationalmedicine 4:1-9 (2015) which is herein incorporated in its entirety by reference. Agulnick et al. described a modified protocol for making pancreatic progenitors cells such that 73%-80% of the cell population consist of PDX1-positive (PDX1+) and NKX6.1+ pancreatic progenitors. The pancreatic progenitor cells were further differentiated into islet-like cells (ICs) that reproducibly contained 73%-89% endocrine cells, of which approximately 40%-50% expressed insulin. A large fraction of these insulin-positive cells were single hormone-positive and expressed the transcription factors PDX1 and NKX6.1. Agulnick et al. describe a protocol wherein the Schulz et al. 2012 protocol was modified by additionally treating with activin A, Wnt3A, and heregulin β1 at stage 3 (days 5-7) and with activin A and heregulin β1 at stage 4 (days 7-13). In one embodiment, the hypoimmunogenic cells are substantially similar to the cells described in U.S. Pat. No. 8,859,286 (which is herein incorporated by reference in its entirety).

Growth, passaging and proliferation of human embryonic stem cells can be performed substantially as described in U.S. Pat. Nos. 7,964,402; 8,211,699; 8,334,138; 8,008,07; and 8,153,429.

Standard Manufacturing Protocol

A standard manufacturing method for making pancreatic endoderm cells (PEC) derived from hESC is disclosed below in Table 2.

| Time point (day) | Stage (1-4) | Media Condition | Roller Bottle Speed (rpm) | 6-well tray Speed (rpm) |
|---|---|---|---|---|
| d(−1) | | hESC XF HA; SP Agg. | 31 | 95 |
| d 0 | 1 | r0.2FBS-ITS1:5000 A100 W50 | 31 | 95 |
| d 1 | | r0.2FBS-ITS1:5000 A100 | 31 | 95 |
| d 2 | 2 | r0.2FBS-ITS1:1000 K25 IV | 31 | 95 |
| d 3 | | r0.2FBS-ITS1:1000 K25 | 31 | 95 |
| d 4 | | r0.2FBS-ITS1:1000 K25 | 31 | 105 |
| d 5 | 3 | db-CTT3 N50 | 31 | 105 |
| d 6 | | db-CTT3 N50 | 31 | 105 |
| d 7 | | db-CTT3 N50 | 31 | 105 |
| d 8 | 4 | db-N50 K50 E50 | 31 | 105 |
| d 9 | | db-N50 K50 E50 | 31 | 95 |
| d 10 | | db-N50 K50 E50 | 31 | 95 |

-continued

| Time point (day) | Stage (1-4) | Media Condition | Roller Bottle Speed (rpm) | 6-well tray Speed (rpm) |
|---|---|---|---|---|
| d 11 | | db-N50 K50 E50 | 31 | 95 |
| d 12 | | db-N50 K50 E50 | 31 | 95 | hESC Agg.: hESC aggregates; XF HA: DMEM/F12 containing GlutaMAX, supplemented with 10% v/v of Xeno-free KnockOut Serum Replacement, 1% v/v non-essential amino acids, 1% v/v penicillin/streptomycin (all from Life Technologies), 10 ng/mL heregulin-1β (Peprotech) and 10 ng/mL activin A (R&D Systems); SP: StemPro ® hESC SFM (Life Technologies); r0.2FBS: RPMI 1640 (Mediatech); 0.2% FBS (HyClone), 1x GlutaMAX-1 (Life Technologies), 1% v/v penicillin/streptomycin; ITS: Insulin-Transferrin-Selenium (Life Technologies) diluted 1:5000 or 1:1000; A100: 100 ng/mL recombinant human Activin A (R&D Systems); W50: 50 ng/mL recombinant mouse Wnt3A (R&D Systems); K25: 25 ng/mL recombinant human KGF (R&D Systems); IV: 2.5 μM TGF-β RI Kinase inhibitor IV (EMD Bioscience); db: DMEM HI Glucose (HyClone) supplemented with 0.5x B-27 Supplement (Life Technologies), 1x GlutaMAX, and 1% v/v penicillin/streptomycin; CTT3: 0.25 μM KAAD-Cyclopamine (Toronto Research Chemicals) and 3 nM TTNPB (Sigma-Aldrich); N50: 50 ng/mL recombinant human Noggin (R&D Systems); K50: 50 ng/mL recombinant human KGF (R&D Systems); E50: 50 ng/mL recombinant human EGF (R&D Systems).

Calcein Release Assay

Calcein release assay is a non-radioactive alternative for studying NK cell cytotoxicity. The target cells take up the fluorescent dye (calcein AM) and cytoplasmically convert it into the active fluorochrome, which is only released from the cell upon lysis. Lysed cells release the fluorochrome into the supernatant, which is then harvested and the amount of fluorescence quantitated in a fluorometer. The percent cell lysis is calculated from the amount of fluorescence present in the supernatant after incubation in the presence or absence of NK cells (effectors), blocking antibody or both.

Specific lysis can be calculated by using the formula, % lysis=100×[(mean fluorescence with antibody-mean spontaneous fluorescence)/(mean maximum fluorescence-mean spontaneous fluorescence)]. Maximum fluorescence was determined by the lysis of cells incubated with detergent (1% Triton X-100) and spontaneous lysis was the fluorescence obtained with target cells without any antibody or effector cells.

Various cell compositions derived from pluripotent stem cells and methods thereof are described herein and can be found in Applicant's U.S. patent application Ser. No. 10/486,408, entitled METHODS FOR CULTURE OF HESC ON FEEDER CELLS, filed Aug. 6, 2002; Ser. No. 11/021,618, entitled DEFINITIVE ENDODERM, filed Dec. 23, 2004; Ser. No. 11/115,868, entitled PDX1 EXPRESSING ENDODERM, filed Apr. 26, 2005; Ser. No. 11/165, 305, entitled METHODS FOR IDENTIFYING FACTORS FOR DIFFERENTIATING DEFINITIVE ENDODERM, filed Jun. 23, 2005; Ser. No. 11/573,662, entitled METHODS FOR INCREASING DEFINITIVE ENDODERM DIFFERENTIATION OF PLURIPOTENT HUMAN EMBRYONIC STEM CELLS WITH PI-3 KINASE INHIBITORS, filed Aug. 15, 2005; Ser. No. 12/729,084 entitled PDX1-EXPRESSING DORSAL AND VENTRAL FOREGUT ENDODERM, filed Oct. 27, 2005; Ser. No. 12/093,590, entitled MARKERS OF DEFINITIVE ENDO-DERM, filed Nov. 14, 2005; Ser. No. 11/993,399, entitled EMBRYONIC STEM CELL CULTURE COMPOSITIONS AND METHODS OF USE THEREOF, filed Jun. 20, 2006; Ser. No. 11/588,693, entitled PDX1-EXPRESSING DOR-SAL AND VENTRAL FOREGUT ENDODERM, filed Oct. 27, 2006; Ser. No. 11/681,687, entitled ENDOCRINE PRO-GENITOR/PRECURSOR CELLS, PANCREATIC HOR-MONE-EXPRESSING CELLS AND METHODS OF PRO-DUCTION, filed Mar. 2, 2007; Ser. No. 11/807,223, entitled METHODS FOR CULTURE AND PRODUCTION OF SINGLE CELL POPULATIONS OF HESC, filed May 24, 2007; Ser. No. 11/773,944, entitled METHODS OF PRO- DUCING PANCREATIC HORMONES, filed Jul. 5, 2007; Ser. No. 11/860,494, entitled METHODS FOR INCREAS-ING DEFINITIVE ENDODERM PRODUCTION, filed Sep. 24, 2007; Ser. No. 12/099,759, entitled METHODS OF PRODUCING PANCREATIC HORMONES, filed Apr. 8, 2008; Ser. No. 12/107,020, entitled METHODS FOR PURI-FYING ENDODERM AND PANCREATIC ENDODERM CELLS DERIVED FORM HUMAN EMBRYONIC STEM CELLS, filed Apr. 21, 2008; Ser. No. 12/618,659, entitled ENCAPSULATION OF PANCREATIC LINEAGE CELLS DERIVED FROM HUMAN PLURIPOTENT STEM CELLS, filed Nov. 13, 2009; Ser. Nos. 12/765,714 and 13/761,078, both entitled CELL COMPOSITIONS FROM DEDIFFERENTIATED REPROGRAMMED CELLS, filed Apr. 22, 2010 and Feb. 6, 2013; Ser. No. 11/838,054, entitled COMPOSITIONS AND METHODS USEFUL FOR CUL-TURING DIFFERENTIABLE CELLS, filed Aug. 13, 2007; Ser. No. 12/264,760, entitled STEM CELL AGGREGATE SUSPENSION COMPOSITIONS AND METHODS OF DIFFERENTIATION THEREOF, filed Nov. 4, 2008; Ser. No. 13/259,15, entitled SMALL MOLECULES SUPPORT-ING PLURIPOTENT CELL GROWTH, filed Apr. 27, 2010; PCT/US11/25628, entitled LOADING SYSTEM FOR AN ENCAPSULATION DEVICE, filed Feb. 21, 2011; Ser. No. 13/992,931, entitled AGENTS AND METHODS FOR INHIBITING PLURIPOTENT STEM CELLS, filed Dec. 28, 2010; and U.S. Design Application Numbers: 29/408, 366 filed Dec. 12, 2011; 29/408,368 filed Dec. 12. 2011; 29/423,365 filed May 31, 2012; and 29/447,944 filed Mar. 13, 2013; U.S. application Ser. No. 14/201,630 entitled 3-DIMENSIONAL LARGE CAPACITY CELL ENCAP-SULATION DEVICE ASSEMBLY, filed Mar. 7, 2014; and U.S. application Ser. No. 14/106,330 entitled IN VITRO DIFFERENTIATION OF PLURIPOTENT STEM CELLS TO PANCREATIC ENDODERM CELLS (PEC) AND ENDOCRINE CELLS, filed Dec. 13, 2013; PCT/US2016/061442, entitled PDX1 PANCREATIC ENDODERM CELLS IN CELL DELIVERY DEVICES AND METHODS THEREOF, filed Nov. 10, 2016; all of which are herein incorporated by reference in their entirety.

Various cell compositions derived from pluripotent stem cells and methods thereof are described herein and can be found in Applications exclusively licensed by Applicant: U.S. Patent Publication no. 2009/0269845 entitled Pluripo-tent cells filed Apr. 24, 2008; U.S. Patent Publication no. 2011/0014703 entitled Differentiation of Human Embryonic Stem Cells filed Jul. 20, 2010; U.S. Patent Publication no. 2011/0014702 entitled Differentiation of Human Embryonic Stem Cells filed Jul. 19, 2010; U.S. Patent Publication no. 2011/0151561 entitled Differentiation of Human Embryonic Stem Cells filed Dec. 16, 2010; U.S. Patent Publication no. 2010/0112692 entitled Differentiation of Human Embryonic Stem Cells filed Oct. 22, 2009; U.S. Patent Publication no. 2012/0052576 entitled Differentiation of Pluripotent Stem Cells filed Aug. 17, 2011; U.S. Patent Publication no. 2010/0112693 entitled Differentiation of human pluripotent stem cells filed Oct. 23, 2009; U.S. Patent Publication no. 2011/0151560 entitled Differentiation of human embryonic stem cells filed Dec. 16, 2010; U.S. Patent Publication no. 2010/0015100 entitled Differentiation of human embryonic stem cells filed Jul. 31, 2008; U.S. Patent Publication no. 2009/0170198 entitled Differentiation of human embryonic stem cells filed Nov. 25, 2008; U.S. Patent Publication no. 2015/0329828 entitled Use of Small Molecules to Enhance MAFA Expression in Pancreatic Endocrine Cells filed May 7, 2015; U.S. Patent Publication no U.S. 2013/0330823 entitled Differentiation of Human Embryonic Stem Cells into Pancreatic Endocrine Cells filed Jun. 6, 2013; Interna-tional patent publication no. WO 2013/192005 entitled Dif-ferentiation of human embryonic stem cells into pancreatic endocrine cells filed Jun. 13, 2013; U.S. Patent Publication no U.S. 2014/0242693 entitled Suspension and clustering of human pluripotent stem cells for differentiation into pancre-atic endocrine cells filed Dec. 30, 2013; U.S. Patent Publi-cation no U.S. 2014/0295552 entitled Suspension and clus-tering of human pluripotent stem cells for differentiation into pancreatic endocrine cells filed Jun. 17, 2014; International patent publication no. WO 2015/065524 entitled Suspension and clustering of human pluripotent stem cells for differen-tiation into pancreatic endocrine cells filed May 21, 2014; U.S. Patent Publication no U.S. 2013/0330823 entitled Dif-ferentiation of Human Embryonic Stem Cells into Pancre-atic Endocrine Cells filed Jun. 6, 2013; U.S. Patent Publi-cation no U.S. 2014/0186953 entitled Differentiation of Human Embryonic Stem Cells Into Pancreatic Endocrine Cells Using HB9 Regulators filed Dec. 18, 2013; U.S. application Ser. No. 14/963,730 filed Dec. 9, 215; U.S. application Ser. No. 14/898,015 filed Dec. 11, 2015 all of which are herein incorporated by reference in their entire-ties.

In one embodiment, hypoimmunogenic cells are encap-sulated within a cell delivery device. The cell delivery device may comprise a non-woven fabric. Cell delivery devices include various layers each of which serves a function or multiple functions. In some embodiments, the cell delivery device includes both a cell-excluding mem-brane and a non-woven fabric. In another embodiment, the delivery device is a TheraCyte (formerly Baxter) device (Irvine, Calif.). TheraCyte cell delivery devices are further described in U.S. Pat. Nos. 6,773,458; 6,156,305; 6,060, 640; 5,964,804; 5,964,261; 5,882,354; 5,807,406; 5,800, 529; 5,782,912; 5,741,330; 5,733,336; 5,713,888; 5,653, 756; 5,593,440; 5,569,462; 5,549,675; 5,545,223; 5,453, 278; 5,421,923; 5,344,454; 5,314,471; 5,324,518; 5,219, 361; 5,100,392; and 5,011,494, which are all herein incorporated by reference in their entireties.

In another embodiment, the delivery device is a device as substantially described in U.S. Pat. Nos. 8,278,106, and as described in U.S. application Ser. No. 14/201,630 filed Mar. 7, 2014 and in PCT Application No. PCT/US2016/061442 filed Nov. 10, 2016, and in U.S. Design Nos. 29/447,944, 29/509,102, 29/484,363, 29/484,360, 29/484,359, 29/484, 357, 29/484,356, 29/484,355, 29/484,362, 29/484,358, 29/408,366, 29/517,319, 29/408,368, 29/518,513, 29/518, 516, 29/408,370, 29/517,144, 29/423,365, 29/530,325, 29/584,046 which are all herein incorporated by reference in their entireties. In other embodiments, cell delivery device or large capacity assembly consist of one or two or more seals that further partition the lumen of the cell delivery device, i.e., a partition seal. See, e.g. Applicant's U.S. Design Application Nos. 29/408366, 29/408368, 29/408370, 29/423,365 and 29/584,046.

In one embodiment, hypoimmunogenic cells are implanted in a perforated cell delivery device which pro-vides direct cell-to-cell contact between host vasculature and the encapsulated cells. Perforated means a hole or pore in the device. In some embodiments not all the layers of the device are perforated. For example see PCT Application No. PCT/US2016/0061442 which is herein incorporated by reference in its entirety which discuses perforated cell delivery devices with perforations in just one layer, for example, the cell-excluding membrane; or, in just the cell-excluding mem-brane and the non-woven fabric layer. In one embodiment, hypoimmunogenic cells are encapsulated in a perforated device surrounded by a non-woven fabric. In these embodiments, the non-woven fabric is on the outside of the cell delivery device. Rather than affecting implanted cells, the non-woven fabric enhances host vascularization surrounding the cell housing. See e.g. PCT/US2016/0061442 and U.S. Pat. No. 8,278,106 (both of which are herein incorporated by reference in their entirety) which describe perforated devices and device polymers.

In one embodiment, the holes/perforations are smaller than cell aggregates contained in the device, such as the hPSC-derived aggregates, e.g. definitive endoderm lineage cell aggregates, contained therein. In one embodiment, a perforated cell delivery device implanted into a rat or human contains perforations in just the cell-excluding membrane (the other layers of the device are not perforated) and wherein the holes are separated by about 2 mm or more and wherein the hole diameter is less than about 100 microns is provided.

Hypoimmunogenic Cell Depletion ("Suicide Gene")

The versatility of embryonic stem cells and induced pluripotent stem (iPS) cells to replace and restore any tissue in the body comes in tandem with an increased risk of cancer. An increased cancer risk has also been associated with gene therapy. Hence, reprogrammed tissues, whether derived from ES cells or iPS cells (Takahashi, K. & Yamanaka, S. Induction of pluripotent stem cells from mouse embryonic and adult fibroblast cultures by defined factors. Cell 126, 663-676, (2006), and Hanna, J. H., Saha, K. & Jaenisch, R. Pluripotency and Cellular Reprogramming: Facts, Hypotheses, Unresolved Issues. Cell 143, 508-525, (2010) both of which are herein incorporated by reference in their entireties) or from other multipotent or progenitor cell, as well as from cells treated with gene therapy vectors, present safety concerns (Knoepfler, P. S. Deconstructing Stem Cell Tumorigenicity: A Roadmap to Safe Regenerative Medicine. Stem Cells 27. 1050-1056, (2009) incorporated by reference in its entirety). For example, subcutaneously implanted iPS cells cause teratomas, and iPS chimeric animals develop primitive malignant cancers with high incidence (Takahashi, K. & Yamanaka, S. Induction of pluripotent stem cells from mouse embryonic and adult fibroblast cultures by defined factors. Cell 126, 663-676, (2006); Knoepfler, P. S. Deconstructing Stem Cell Tumorigenicity: A Roadmap to Safe Regenerative Medicine. Stem Cells 27, 1050-1056, (2009)). While benign teratomas may readily be removed by surgery, invasive cancers remain a risk with cell therapies.

Strategies for overcoming stem cell tumorigenicity, including a suicide gene strategy, have been considered (Knoepfler, P. S. Deconstructing Stem Cell Tumorigenicity: A Roadmap to Safe Regenerative Medicine. Stem Cells 27, 1050-1056, (2009)). Specifically, a gene can be selectively introduced into the implanted cell which encodes for an enzyme that metabolizes a systemically available pro-drug to an active anti-neoplastic agent locally. For example, treatment with ganciclovir, which is converted by thymidine kinase into compounds that become toxic after triphosphorylation by cellular kinases, resulted in destruction of the tumor cells in vitro. Thus, implanted cells can be modified to artificially generate exploitable biochemical differences between host tissues and implanted cells. Targeting of the implanted cells is achieved by selection of the vector used to deliver the suicide gene, as well as by the biology of suicide gene/prodrug system employed. As a result, high doses of the drug generated only in the environment where the cells are implanted limits side effects in other tissues.

Hypoimmunogenic cell depletion may be accomplished by selectively introducing a gene into the hypoimmunogenic cell, the expression of which gene either directly results in hypoimmunogenic cell death or renders the hypoimmunogenic cell specifically susceptible to other pharmacological agents. In vivo or ex vivo depletion of hypoimmunogenic cell according to this method may be accomplished by delivering the desired gene to the hypoimmunogenic cell using a viral gene delivery systems such as, but not limited to a retrovirus, adenovirus or an adeno-associated virus gene delivery system. The desired viral delivery system may comprise a virus whose genome encodes a protein which, for example, directly causes cell death, for example by inducing apoptosis of the hypoimmunogenic cell. Alternatively, the viral delivery system may contain a virus whose genome encodes, for example, a herpes simplex virus thymidine kinase gene. Expression of the herpes simplex virus thymidine kinase gene in the hypoimmunogenic cell renders the hypoimmunogenic cell sensitive to pharmacologic doses of ganciclovir. Thus, subsequent contact of the virally transduced hypoimmunogenic cell with ganciclovir results in death of the hypoimmunogenic cell. Hypoimmunogenic cell depletion may be accomplished by introducing a so call "suicide gene" via genome editing applications, e.g., ZFN, CRISPR/cas and TALEN systems.

Agents such as ganciclovir which mediate killing of a cell upon expression of a gene such as thymidine kinase, are referred to herein as "cell death inducing agent."

Genes which can be used to kill hypoimmunogenic cells include, but are not limited to, herpes simplex virus thymidine kinase and cytosine deaminase, or any gene which induces the death of a cell that can be placed under the control of an inducible promoter/regulatory sequence (referred to interchangeably herein as a "promoter/regulatory sequence" or as a "promoter"). The gene is transferred into a hypoimmunogenic cell, the cells are selected under an appropriate selective pressure, the cells are transferred to the patient, and are allowed to engraft therein. The patient is then treated with an agent, which induces promoter activity, thereby inducing expression of the gene whose product functions to kill hypoimmunogenic cells. In the case of thymidine kinase, other agents which facilitate killing of the cell by this enzyme may also be used, such as, for example, ganciclovir (Bonini et al., 1997, Science 276:1719-1724; Bordignon et al., 1995, Human Gene Therapy 6:813-819; Minasi et al., 1993, J. Exp. Med. 177: 1451-1459; Braun et al., 1990, Biology of Reproduction 43:684-693). Other genes useful for this purpose include, but are not limited to, constitutively active forms of caspases 3, 8, and 9, bax, granzyme, diphtheria toxin, *Pseudomonas* A toxin, ricin and other toxin genes are disclosed elsewhere herein. The generation of appropriate constructs for delivery of such genes to a human will be readily apparent to the skilled artisan and is described, for example, in Sambrook et al. (1989, Molecular Cloning: A Laboratory Manual, Cold Spring Harbor Laboratory, New York) and in Ausubel et al. (1997, Current Protocols in Molecular Biology, John Wiley & Sons, New York).

It is important that the gene which is transferred into the hypoimmunogenic cells, for the purpose of killing the cells, be placed under the control of the appropriate promoter sequence, such that induction of expression of the gene may be effected upon addition to the cells (administration to the mammal) of the appropriate inducer. Such inducible promoter sequences include, but are not limited to promoters which are induced upon addition of a metal to the cells, steroid inducible promoters and the like. In one preferred embodiment, the ecdysone promoter system may be employed. In this embodiment, the ecdysone promoter is cloned upstream of the ecdysone receptor protein sequence, which is positioned upstream of a second promoter sequence which drives expression of the ecdysone binding site operably linked to the desired gene, for example, the desired toxin. Induction of the promoter induces expression of the toxin, thereby effecting killing of the cell in which the toxin gene resides.

Cells which have transduced therein a gene for cell killing, when such cells are transduced in an ex vivo manner, may be selected (i.e., separated from cells which do not comprise the gene) by providing the cells with a selectable marker in addition to the transduced gene. Selectable markers are well known in the art and are described, for example, in Sambrook et al. (1989, Molecular Cloning: A Laboratory Manual, Cold Spring Harbor, N.Y.).

Hypoimmunogenic cell depletion may further be accomplished by introducing into a population of hypoimmunogenic cells an oligonucleotide (for example, but not limited to, an antisense molecule) or a ribozyme, which oligonucleotide or ribozyme is capable of inducing death of the hypoimmunogenic cell, or of inducing impairment of hypoimmunogenic cell function. Such oligonucleotides include those which target an essential function of an hypoimmunogenic cell, defined herein as being one which either kills a hypoimmunogenic cell or impairs the function of the hypoimmunogenic cell with respect to stimulation of T cells. Such functions of a hypoimmunogenic cell include, but are not limited to, the costimulatory function of B71 and B72, CD40, among others. Thus, oligonucleotides and ribozymes which are useful in the methods of the invention include, but are not limited to, those which are directed against these targets.

As noted herein, depletion of hypoimmunogenic cell includes impairment of hypoimmunogenic cell function. Impairment of hypoimmunogenic cell function includes all forms of hypoimmunogenic cell impairment with or without physical removal or depletion of hypoimmunogenic cell. Thus, impairment of hypoimmunogenic cell function includes the use of an antibody that blocks the function of hypoimmunogenic cell surface molecules which are critical for hypoimmunogenic cell function.

Alternatively, peptides which block the function of hypoimmunogenic cell surface molecules, which blocking results in impairment of hypoimmunogenic cell function, may be used to effectively deplete hypoimmunogenic cell in a host organism. Such peptides include, but are not limited to, those which are designed to specifically bind receptor molecules on the surface of hypoimmunogenic cells, and those which are designed to, for example, inhibit essential enzymatic functions in these cells.

Similarly, genes and oligonucleotides which are designed for the same purpose as described herein, are also included as tools in the methods of the invention. Thus, peptides, oligonucleotides and genes which impair the biological function of a hypoimmunogenic cell, as that term is defined herein, are also contemplated for use in the methods of the invention disclosed herein.

The invention further encompasses the use of pharmaceutical compositions of an appropriate hypoimmunogenic cell depleting composition to practice the methods of the invention, the compositions comprising an appropriate hypoimmunogenic cell depleting composition and a pharmaceutically-acceptable carrier. In some embodiments, the cell depleting composition is a chimeric composition comprising an antibody and a toxin.

As used herein, the term "pharmaceutically-acceptable carrier" means a chemical composition with which an appropriate hypoimmunogenic cell depleting composition may be combined and which, following the combination, can be used to administer the appropriate hypoimmunogenic cell depleting composition to a mammal.

Pharmaceutical compositions that are useful in the methods of the invention may be administered systemically in oral solid formulations, ophthalmic, suppository, aerosol, topical or other similar formulations. In addition to the hypoimmunogenic cell depleting composition, such pharmaceutical compositions may contain pharmaceutically-acceptable carriers and other ingredients known to enhance and facilitate drug administration. Other possible formulations, such as nanoparticles, liposomes, resealed erythrocytes, and immunologically based systems may also be used to administer an appropriate hypoimmunogenic cell depleting composition according to the methods of the invention.

Methods of introducing "suicide genes" into cells are disclosed in US20060222633 which is herein incorporated by reference in its entirety.

The invention includes a method of depleting hypoimmunogenic cells in a mammalian host. After the hypoimmunogenic cells have been transplanted into a host, the method comprises contacting the hypoimmunogenic cells with a cell depleting composition to effect impairment of hypoimmunogenic cell function or killing of the hypoimmunogenic cell, thereby depleting the hypoimmunogenic cells in the mammalian host.

In another aspect, the hypoimmunogenic cell depleting composition is selected from the group consisting of a toxin, an antibody, a radioactive molecule, a nucleic acid, a peptide, a peptidomemetic and a ribozyme.

In one aspect, the toxin is an immunotoxin. The toxin is selected from the group consisting of ricin, diptheria toxin and pseudomonas exotoxin A.

In another embodiment, the antibody is selected from the group consisting of antibody specific for CD1a, antibody specific for CD11c, antibody specific for MHCII, antibody specific for CD11b, antibody specific for DEC205, antibody specific for B71, antibody specific for B72, antibody specific for CD40, antibody specific for Type I lectins and antibody specific for Type II lectins.

In yet another embodiment, the nucleic acid molecule is selected from the group consisting of a gene and an oligonucleotide.

In a further embodiment, the radioactive molecule is a radioactively labeled antibody.

In another embodiment, the antigen depleting composition is a chimeric composition comprising an antibody and a toxin. The toxin may be selected from the group consisting of ricin, diptheria toxin and pseudomonas exotoxin A.

In another embodiment, the antibody is selected from the group consisting of f antibody specific for CD1a, antibody specific for CD11c, antibody specific for MHCII, antibody specific for CD11b, antibody specific for DEC205, antibody specific for B71, antibody specific for B72, antibody specific for CD40, antibody specific for Type I lectins and antibody specific for Type II lectins.

Combination Product

The embodiments described herein also disclose a combination product, which refers to a device loaded with hypoimmunogenic cells or therapeutic agent, i.e. each alone may be a candidate medical device or cell product, but used together they make a combination product. In one embodiment, the combination product refers to a perforated device loaded with hypoimmunogenic cells. This is referred to as a "combination product", or "perforated combination product." The device (perforated or not) can be any macro cell delivery device described herein including but not limited to those cell encapsulation devices as described in U.S. Pat. Nos. 8,278,106 and 9,526,880, PCT Application No. PCT/US2016/0061442 and U.S. Design Patent Nos. D714956, D718472, D718467, D718466, D718468, D718469, D718470, D718471, D720469, D726306, D726307, D728095, D734166, D734847, D747467, D747468, D747798, D750769, D750770, D755986, D760399, D761423, D761424 (incorporated by reference in their entirety). The cells loaded into the device (perforated or not) may be any hypoimmunogenic cells discussed above including but not limited to definitive endoderm, PDX1-positive endoderm, PDX1-positive foregut endoderm, pancreatic endoderm, pancreatic endoderm cells expressing PDX1 and NKX6.1, endocrine progenitors, endocrine progenitors expressing NKX6.1 and INS, immature beta cell, immature beta cells expressing NKX6.1, INS and MAFB, mature endocrine cells, mature endocrine cells expressing INS, GCG, SST and PP, and mature beta cells and mature beta cells expressing INS and MAFA.

Perforated delivery devices loaded with pancreatic endoderm or pancreatic progenitor hypoimmunogenic cells which mature when implanted in vivo are intended to reduce insulin dependence and/or reduce hypoglycemia in patients with diabetes. This includes, but is not limited to high-risk type I diabetic patients who are hypoglycemia unaware, labile (brittle), or have received an organ transplant and who can tolerate, or are already on, immune suppression therapy. As substantially described in PCT Application No. PCT/US2016/0061442 (incorporated by reference in its entirety), the primary method of action is via human pancreatic endoderm cells (PEC) or pancreatic progenitor hypoimmunogenic cells, contained in a permeable, durable, implantable medical device that facilitates direct host vascularization. The PEC hypoimmunogenic cells differentiate and mature into therapeutic glucose-responsive, insulin-releasing hypoimmunogenic cells after implantation. As such, the perforated combination product supports secretion of human insulin. The perforated combination product limits distribution (egress) of PEC hypoimmunogenic cells in vivo. The perforated combination product will be implanted in a location that permits sufficient vascular engraftment to sustain the population of therapeutic hypoimmunogenic cells within the device and facilitate distribution of insulin and other pancreatic products to the bloodstream. The perforated combination product is intended to be implanted and explanted with conventional surgical tools, and to provide a therapeutic dose for two years or more. The device is intended to retain an adequate dose of the PEC hypoimmunogenic cells product during formulation, shelf-life, handling and surgical implant to achieve clinical efficacy and ensure the cell product is located within the tissue capsule to meet safety requirements.

Knock-In

In certain embodiments, tolerogenic factors can be inserted or reinserted into genome-edited stem cell lines to create immune-privileged universal donor stem cell lines. In certain embodiments, the universal stem cells disclosed herein have been further modified to express one or more tolerogenic factors. Exemplary tolerogenic factors include, without limitation, one or more of HLA-C, HLA-E, HLA-F, HLA-G, PD-L1, CTLA-4-Ig, CD47, CI-inhibitor, and IL-35. Any method of gene editing can be used to facilitate the insertion of tolerogenic factors, such as the tolerogenic factors above, into an AAVSI locus, to actively inhibit immune rejection.

Specifically, in certain embodiments, the inventions disclosed herein relate to a stem cell, the genome of which has been altered to reduce or delete critical components of at least one MHC-Class I gene and at least one NK activating ligand gene and which has been further altered to increase expression of one or more tolerogenic factors. In certain embodiments, the inventions disclosed herein relate to a stem cell, the genome of which has been altered to reduce or delete critical components of at least one MHC-Class I gene and at least one NK activating ligand gene and which has been further altered to increase expression of one or more of HLA-C, HLA-E, HLA-F, HLA-G, PD-L1, CTLA-4-Ig, CD47, CI-inhibitor, and IL-35.

Embodiments

Other embodiments of the invention are described with reference to the numbered paragraphs below.

Related to Blocking Antibody: Composition

Paragraph 1: A composition comprising a pluripotent derived cell that lacks at least one human leucocyte antigen (HLA)-Class I gene and at least one agent that binds to a Natural Killer (NK) cell activating ligand. Paragraph 2: The composition of paragraph 1, wherein the agent is an antibody. Paragraph 3: The composition of paragraph 1, wherein the HLA-Class I gene is B2M.

Paragraph 4: The composition of paragraphs 1-3, wherein the NK cell activating ligand is ICAM-1, CEACAMI, CADM1, MICA, MICB or combinations thereof.

Paragraph 5: The composition of paragraphs 1-2, wherein the NK cell activating ligand is ICAM-1 and CEACAM1.

Paragraph 6: The composition of paragraphs 1-2, wherein the NK cell activating ligand is ICAM-1, CEACAMI, CADM1, MICA and MICB.

Paragraph 7: The composition of paragraphs 1-2, wherein the pluripotent derived cells further express a protein which when expressed in the presence of a cell death inducing agent, the agent is capable of killing the pluripotent cells.

Paragraph 8: The composition of paragraph 7, wherein the cell death inducing agent is ganciclovir.

Paragraph 9: The composition of any one of paragraphs 1-8, wherein the pluripotent derived cells further overexpress one or more tolerogenic factors.

Paragraph 10: The composition of paragraph 9, wherein the tolerogenic factors are HLA-C, HLA-E, HLA-G, PD-L1, CTLA-4-Ig, CD47, CI-inhibitor, or IL-35.

Paragraph 11: The composition of paragraph 9, wherein the tolerogenic factors are HLA-C, HLA-E and HLA-G.

Related to Blocking Antibody: Method

Paragraph 1: A method of preventing cellular graft rejection of human pluripotent derived cells, comprising administering to a subject in need of treatment a composition comprising a target cell population that lacks at least one HLA-Class I gene, and at least one agent that binds an NK cell activating ligand on the target cell in an amount effective to suppress the subject's NK cell attack thereby preventing cellular graft rejection of human pluripotent derived cells.

Paragraph 2: The method of paragraph 1, wherein the agent is an antibody.

Paragraph 3: The method of paragraph 1, wherein the subject's immune response to a NK cell activating ligand is suppressed.

Paragraph 4: The method of paragraph 1, wherein the NK cell activating ligand is ICAM-1, CEACAMI, CADM1, MICA or MICB.

Paragraph 5: The method of paragraph 1, wherein the NK cell activating ligand is ICAM-1, CEACAMI, CADM1, MICA and MICB.

Paragraph 6: The method of paragraph 1, wherein the subject is human.

Paragraph 7: The method of paragraph 2, wherein the antibody is a human antibody.

Related to hES Cell Double Knockout: Compositions

Paragraph 1: An in vitro cell population comprising pluripotent derived cells, wherein the pluripotent derived cells lack at least one HLA-Class I gene and at least one Natural killer (NK) cell activating ligand gene.

Paragraph 2: The in vitro cell population of paragraph 1, wherein the HLA-Class I gene is B2M.

Paragraph 3: The in vitro cell population of paragraph 1-2, wherein the NK cell activating ligand is ICAM-1, CEACAM1, CADM1, MICA, MICB or combinations thereof.

Paragraph 4: The in vitro cell population of paragraph 1-2, wherein the NK cell activating ligand is ICAM-1 and CEACAM1.

Paragraph 5: The in vitro cell population of paragraph 1-2, wherein the NK cell activating ligand is ICAM-1, CEACAMI, CADM1, MICA and MICB. Paragraph 6: The in vitro cell population of paragraph 1-5, wherein the pluripotent derived cells further express a protein which when expressed in the presence of a cell death inducing agent, the agent is capable of killing the pluripotent derived cells.

Paragraph 7: The in vitro cell population of paragraph 6, wherein the cell death inducing agent is ganciclovir.

Paragraph 8: The in vitro cell population of any one of paragraphs 1-7, wherein the derived pluripotent cells further overexpress one or more tolerogenic factors.

Paragraph 9: The in vitro cell population of paragraphs 8, wherein the tolerogenic factors are HLA-C, HLA-E, HLA-G, PD-L1, CTLA-4-Ig, CD47, CI-inhibitor, IL-35 or combinations thereof.

Paragraph 10: The in vitro cell population of paragraphs 9, wherein the tolerogenic factors are HLA-C, HLA-E and HLA-G.

Related to Pluripotent Stem Cells Triple Knockout: Compositions

A human pluripotent stem cell comprising a modified genome comprising: a first genomic modification in which the B2M gene has been edited to reduce or eliminate B2M surface expression and/or activity in the cell; (b) a second genomic modification in which the ICAM-1 gene has been edited to reduce or eliminate ICAM-1 surface expression and/or activity in the cell; and (c) a third genomic modification in which the CEACAM1 gene has been edited to reduce or eliminate CEACAMI surface expression and/or activity in the cell.

Related to Knockout of Transcriptional Regulators: Compositions

Paragraph 12: A pluripotent derived cell comprising modulated expression of one or more MHC-Class I or MHC-Class II genes or protein complexes and one or more NK cell activating ligands relative to a wild-type pluripotent stem cell, wherein the pluripotent stem cell has one or more genes encoding one or more transcriptional regulators of MHC-Class I or MHC-Class II and NK cell activating ligand genes deleted from at least one allele of the cell.

Paragraph 13: A pluripotent stem cell comprising modulated expression of one or more NK cell activating ligands relative to a wild-type human pluripotent stem cell.

Paragraph 14: A human pluripotent stem cell that does not express B2M or ICAM-1.

Paragraph 15: A human pluripotent stem cell that does not express CIITA or ICAM-1.

Paragraph 16: A human pluripotent stem cell that does not express LRC5 or ICAM-1.

Paragraph 17: A human pluripotent stem cell that does not express one or more of NLRC5, CIITA and B2M and further does not express one or more of ICAM-1, CEACAM1, CADM1, MICA and MICB.

Paragraph 18: A human pluripotent stem cell that does not express one or more of HLA-A, HLA-B and HLA-C and further does not express one or more of ICAM-1, CEACAMI, CADM1, MICA and MICB.

Paragraph 19: A human pluripotent stem cell that does not express one or more of one or more MHC-Class I antigens and one or more NK cell activating ligands and further has one or more tolerogenic factors inserted into a safe harbor locus of at least one allele of the cell.

Paragraph 20: A human pluripotent stem cell comprising a modified genome comprising a first genomic modification in which the B2M gene has been edited to reduce or eliminate B2M surface expression and/or activity in the cell and in which the ICAM-1 gene has been edited to reduce or eliminate ICAM-1 surface expression and/or activity in the cell.

Paragraph 21: A human pluripotent stem cell comprising a modified genome comprising: a first genomic modification in which the B2M gene has been edited to reduce or eliminate B2M surface expression and/or activity in the cell; and (b) a second genomic modification in which the ICAM-1 gene has been edited to reduce or eliminate ICAM-1 surface expression and/or activity in the cell.

Related to hES Double Knockout Cells: Compositions

Paragraph 1: An in vitro cell population comprising pluripotent cells, wherein the pluripotent cells lack at least one functional MHC-Class I cell surface protein and at least one functional Natural killer (NK) cell activating ligand cell surface protein.

Paragraph 2: The in vitro cell population of paragraph 1, wherein the MHC-Class I cell surface protein is HLA-A, HLA-B, HLA-C or combinations thereof.

Paragraph 3: The in vitro cell population of paragraphs 1-2, wherein the MHC-Class I cell surface protein is B2M.

Paragraph 4: The in vitro cell population of any one of paragraphs 1-3, wherein the pluripotent cells lack at least two functional NK cell activating ligand cell surface proteins.

Paragraph 5: The in vitro cell population of any one of paragraphs 1-4, wherein the pluripotent cells lack at least three functional NK cell activating ligand cell surface proteins.

Paragraph 6: The in vitro cell population of any one of paragraphs 1-5, wherein NK cell activating ligand cell surface protein is ICAM-1, CEACAMI, CADM1, MICA, MICB or combinations thereof.

Paragraph 7: The in vitro cell population of any one of paragraphs 1-5, wherein the NK cell activating ligand cell surface protein is ICAM-1 and CEACAM1.

Paragraph 8: The in vitro cell population of any one of paragraphs 1-7, wherein the pluripotent cells further express a protein which when expressed in the presence of a cell death inducing agent, the agent is capable of killing the pluripotent cells.

Paragraph 9: The in vitro cell population of any one of paragraphs 1-8, wherein the protein which when expressed in the presence of a cell death inducing agent, the agent is capable of killing the pluripotent cells is herpes simplex virus, thymidine kinase or cytosine deaminase.

Paragraph 10: The in vitro cell population of any one of paragraphs 8-9, wherein the cell death inducing agent is ganciclovir.

Related to hES Double Knockout Cells:
Compositions

Paragraph 1: An in vitro cell population comprising pluripotent cells, wherein the pluripotent cells have reduced expression of at least one MHC-Class I cell surface protein and reduced function and/or expression of at least one NK activating ligand cell surface protein relative to the original genotype or relative to a wild-type human cell.

Paragraph 2: An in vitro cell population comprising pluripotent cells, wherein the pluripotent cells have reduced expression of one or more of HLA-A, HLA-B and HLA-C cell surface protein and reduced function and/or expression of at least one NK activating ligand cell surface protein relative to the original genotype or relative to a wild-type human cell.

Paragraph 3: An in vitro cell population comprising pluripotent cells, wherein the pluripotent cells lack functional HLA cell surface protein expression, NK activating ligand cell surface protein expression and have a protein which when expressed in the pluripotent cells in the presence of the cell death inducing agent, the agent is capable of killing the pluripotent cells.

Paragraph 4: A stem cell wherein expression of one or more HLA-Class I cell surface protein and one or more NK activating ligand cell surface protein is modulated relative to a wild-type stem cell.

Paragraph 5: A pluripotent cell wherein expression of one or more HLA-Class I cell surface protein, one or more NK activating ligand cell surface protein, and one or more tolerogenic cell surface protein factors is modulated relative to a wild-type pluripotent cell and wherein the pluripotent cells further express a protein which when expressed in the presence of a cell death inducing agent, the agent is capable of killing the pluripotent cells.

Paragraph 6: An in vitro cell population comprising pluripotent cells, wherein the pluripotent cells lack functional MHC-Class I genes and Natural killer (NK) cell activating ligand genes and wherein the pluripotent cells overexpress tolerogenic cell surface protein factors relative to a wild-type pluripotent cell and wherein the pluripotent cells further express a protein which when expressed in the presence of a cell death inducing agent, the agent is capable of killing the pluripotent cells.

Related to PEC Double Knockout Cells:
Composition

Paragraph 1: An in vitro cell population comprising pancreatic endoderm (PEC) cells, wherein the PEC cells lack at least one functional HLA-Class I gene and at least one Natural killer (NK) cell activating ligand gene.

Paragraph 2: The in vitro cell population of paragraph 1, wherein the at least one HLA-Class I gene is B2M.

Paragraph 3: The in vitro cell population of paragraph 1-2, wherein the at least one NK cell activating ligand is ICAM-1, CEACAM1, CADM1, MICA, MICB or combinations thereof.

Paragraph 4: The in vitro cell population of paragraph 1-2, wherein the at least one NK cell activating ligand is ICAM-1 and CEACAM1.

Paragraph 5: The in vitro cell population of paragraph 1-2, wherein the at least one NK cell activating ligand is ICAM-1, CEACAMI, CADM1, MICA and MICB.

Paragraph 6: The in vitro cell population of paragraph 1-5, wherein the PEC cells further express a protein which when expressed in the presence of a cell death inducing agent, the agent is capable of killing the PEC cells.

Paragraph 7: The in vitro cell population of paragraph 6, wherein the cell death inducing agent is ganciclovir.

Paragraph 8: The in vitro cell population of paragraph 6, wherein the gene which when expressed in the presence of a cell death inducing agent, the agent is capable of killing the PEC cells, is herpes simplex virus, thymidine kinase or cytosine deaminase.

Paragraph 9: The in vitro cell population of any one of paragraphs 1-8, wherein the PEC cells further overexpress one or more tolerogenic cell surface proteins.

Paragraph 10: The in vitro cell population of paragraphs 1-9, wherein the tolerogenic factors are HLA-C, HLA-E, HLA-G, PD-L1, CTLA-4-Ig, CD47, CI-inhibitor, IL-35 or combinations thereof.

Paragraph 11: The in vitro cell population of paragraphs 1-9, wherein the tolerogenic factors are HLA-C, HLA-E and HLA-G.

Paragraph 12: An in vitro cell population comprising pancreatic endoderm (PEC) cells, wherein the PEC cells lack at least one functional MHC-Class I gene, MHC-Class II gene and Natural killer (NK) cell activating ligand gene.

Paragraph 13: An in vitro cell population comprising pancreatic endoderm (PEC) cells, wherein the PEC cells lack at least one functional MHC-Class I gene and MHC-Class II gene and lack at least two Natural killer (NK) cell activating ligand genes.

Paragraph 14: A pancreatic endoderm (PEC) cell wherein one or more HLA-Class I gene and one or more NK activating ligand gene is modulated relative to a wild-type PEC cell.

Paragraph 15: A pancreatic endoderm (PEC) cell wherein expression of one or more HLA-Class I cell surface proteins, one or more NK activating ligand, and one or more tolerogenic factors is modulated relative to a wild-type PEC cell and wherein the pancreatic endoderm cell further express a protein which when expressed in the presence of a cell death inducing agent, the agent is capable of killing the PEC cells.

Paragraph 16: A pancreatic endoderm (PEC) cell that does not express B2M or ICAM-1.

Paragraph 17: A pancreatic endoderm (PEC) cell that does not express CIITA or ICAM-1.

Paragraph 18: A pancreatic endoderm (PEC) cell that does not express LRC5 or ICAM-1.

Paragraph 19: A pancreatic endoderm (PEC) cell that does not express one or more of NLRC5, CIITA and B2M and further does not express one or more of ICAM-1, CEACAM1, CADM1, MICa and MICB.

Paragraph 20: A pancreatic endoderm (PEC) cell that does not express one or more of HLA-A, HLA-B and HLA-C and further does not express one or more of ICAM-1, CEACAM1, CADM1, MICa and MICB.

Paragraph 21: A pancreatic endoderm (PEC) cell that does not express one or more MHC-Class I cell surface proteins and one or more NK cell activating ligands and further has one or more tolerogenic factors inserted into a safe harbor locus of at least one allele of the cell.

Paragraph 22: A pancreatic endoderm (PEC) cell comprising a modified genome comprising a first genomic modification in which the B2M gene has been edited to reduce or eliminate B2M surface expression and/or activity in the cell and in which the ICAM-1 gene has been edited to reduce or eliminate ICAM-1 surface expression and/or activity in the cell.

Paragraph 23: A pancreatic endoderm (PEC) cell comprising a modified genome comprising: a first genomic modification in which the B2M gene has been edited to reduce or eliminate B2M surface expression and/or activity in the cell; and (b) a second genomic modification in which the ICAM-1 gene has been edited to reduce or eliminate ICAM-1 surface expression and/or activity in the cell.

Paragraph 24: A pancreatic endoderm (PEC) cell comprising a modified genome comprising: a first genomic modification in which the B2M gene has been edited to reduce or eliminate B2M surface expression and/or activity in the cell; (b) a second genomic modification in which the ICAM-1 gene has been edited to reduce or eliminate ICAM-1 surface expression and/or activity in the cell; and (c) a third genomic modification in which the CEACAMI-gene has been edited to reduce or eliminate CEACAMIsurface expression and/or activity in the cell.

Related to Hypoimmunogenic Cells

Paragraph 1: An in vitro cell population comprising hypoimmunogenic cells, wherein the hypoimmunogenic cells lack at least one functional HLA-Class I cell surface protein and at least one functional NK cell activating ligand cell surface protein.

Paragraph 2: The in vitro cell population of paragraph 1, wherein the HLA-Class I cell surface protein is B2M.

Paragraph 3: The in vitro cell population of paragraph 1-2, wherein the NK cell activating ligand is ICAM-1, CEACAM1, CADM1, MICA, MICB or combinations thereof.

Paragraph 4: The in vitro cell population of paragraph 1-2, wherein the NK cell activating ligand is ICAM-1 and CEACAM1.

Paragraph 5: The in vitro cell population of paragraph 1-2, wherein the NK cell activating ligand is ICAM-1, CEACAM1, CADM1, MICA and MICB.

Paragraph 6: The in vitro cell population of paragraph 1-5, wherein the hypoimmunogenic cells further express a protein which when expressed in the presence of a cell death inducing agent, the agent is capable of killing the hypoimmunogenic cells.

Paragraph 7: The in vitro cell population of any one of paragraphs 1-6, wherein the hypoimmunogenic cells further overexpresses one or more tolerogenic factors.

Paragraph 8: The in vitro cell population of paragraphs 1-7, wherein the tolerogenic factors are HLA-C, HLA-E, HLA-G, PD-L1, CTLA-4-Ig, CD47, CI-inhibitor, IL-35 and combinations thereof.

Paragraph 9: The in vitro cell population of paragraphs 1-7, wherein the tolerogenic factors are HLA-C, HLA-E and HLA-G.

Paragraph 10: An in vitro cell population comprising hypoimmunogenic cells, wherein the hypoimmunogenic cells lack at least one functional MHC-Class I gene and at least one NK cell activating ligand gene.

Paragraph 11: An in vitro cell population comprising hypoimmunogenic cells, wherein the hypoimmunogenic cells lack at least one functional MHC-Class I gene, MHC-Class II gene and NK cell activating ligand gene.

Paragraph 12: The in vitro cell population of paragraphs 10 or 11, wherein the MHC-Class I gene is HLA-A, HLA-B, HLA-C or combinations thereof.

Paragraph 13: The in vitro cell population of paragraphs 10, 11 or 12, wherein the MHC-Class I gene is B2M.

Paragraph 14: The in vitro cell population of any one of paragraphs 10-13, wherein the hypoimmunogenic cells lack at least two functional NK cell activating ligand genes.

Paragraph 15: The in vitro cell population of any one of paragraphs 10-13, wherein the hypoimmunogenic cells lack at least three functional NK cell activating ligand genes.

Paragraph 16: The in vitro cell population of any one of paragraphs 10-13, wherein NK cell activating ligand is ICAM-1, CEACAM1, CADM1, MICA, MICB or combinations thereof.

Paragraph 17: The in vitro cell population of any one of paragraphs 10-13, wherein the NK cell activating ligand is ICAM-1 and CEACAM1.

Paragraph 18: The in vitro cell population of any one of paragraphs 10-13, wherein the NK cell activating ligand is ICAM-1, CEACAMI, CADM1, MICA and MICB.

Paragraph 19: The in vitro cell population of any one of paragraphs 10-18, wherein the hypoimmunogenic cells further express a protein which when expressed in the presence of a cell death inducing agent, the agent is capable of killing the hypoimmunogenic cells.

Paragraph 20: The in vitro cell population of any one of paragraphs 7-15, wherein the hypoimmunogenic cells are hES cells or pancreatic lineage cells.

Paragraph 21: A hypoimmunogenic cell wherein expression of one or more HLA-Class I cell surface protein and one or more NK activating ligand cell surface protein is modulated relative to a wild-type hypoimmunogenic cells.

Paragraph 22: A hypoimmunogenic cell wherein expression of one or more HLA-Class I cell surface protein, one or more NK activating ligand, and one or more tolerogenic cell surface protein factors is modulated relative to a wild-type hypoimmunogenic cell and wherein the pluripotent cells further express a protein which when expressed in the presence of a cell death inducing agent, the agent is capable of killing the hypoimmunogenic cells.

Paragraph 23: A hypoimmunogenic stem cell comprising modulated expression of one or more MHC-Class I or MHC-Class II cell surface proteins and one or more NK cell activating ligands relative to a wild-type pluripotent stem cell, wherein the pluripotent stem cell has one or more genes encoding one or more transcriptional regulators of MHC-Class I or MHC-Class II and NK cell activating ligand genes deleted from at least one allele of the cell.

Paragraph 24: A hypoimmunogenic cell comprising modulated expression of one or more NK cell activating ligands relative to a wild-type human hypoimmunogenic cell.

Paragraph 25: A human hypoimmunogenic cell that does not express B2M or ICAM-1.

Paragraph 26: A human hypoimmunogenic cell that does not express CIITA or ICAM-1.

Paragraph 27: A human hypoimmunogenic cell that does not express LRC5 or ICAM-1.

Paragraph 28: A human hypoimmunogenic cell that does not express one or more of NLRC5, CIITA and B2M and further does not express one or more of ICAM-1, CEACAM1, CADM1, MICa and MICB.

Paragraph 29: A human hypoimmunogenic cell that does not express one or more of HLA-A, HLA-B and HLA-C and further does not express one or more of ICAM-1, CEACAM1, CADM1, MICa and MICB.

Paragraph 30: A human hypoimmunogenic cell that does not express one or more of one or more MHC-Class I cell surface proteins and one or more NK cell activating ligands and further has one or more tolerogenic factors inserted into a safe harbor locus of at least one allele of the cell.

Paragraph 31: A hypoimmunogenic cell comprising a modified genome comprising a first genomic modification in which the B2M gene has been edited to reduce or eliminate B2M surface expression and/or activity in the cell and in which the ICAM-1 gene has been edited to reduce or eliminate ICAM-1 surface expression and/or activity in the cell.

Paragraph 32: A hypoimmunogenic stem cell comprising a modified genome comprising: a first genomic modification in which the B2M gene has been edited to reduce or eliminate B2M surface expression and/or activity in the cell; and (b) a second genomic modification in which the ICAM-1 gene has been edited to reduce or eliminate ICAM-1 surface expression and/or activity in the cell.

Paragraph 33: A hypoimmunogenic stem cell comprising a modified genome comprising: a first genomic modification in which the B2M gene has been edited to reduce or eliminate B2M surface expression and/or activity in the cell; (b) a second genomic modification in which the ICAM-1 gene has been edited to reduce or eliminate ICAM-1 surface expression and/or activity in the cell; and (c) a third genomic modification in which the CEACAMI gene has been edited to reduce or eliminate CEACAM1 surface expression and/or activity in the cell.

Methods for Double Knockout

Paragraph 1: A method of reducing graft rejection, comprising:
 a) administering to a subject in need of a transplant, an effective amount of a graft comprising a pancreatic endoderm cell population wherein the function of at least one HLA-Class I cell surface protein and at least one NK cell activating ligand cell surface protein is disrupted.

Paragraph 2: The method of paragraph 1, wherein the HLA-Class I cell surface protein is B2M.

Paragraph 3: The method of paragraph 1-2, wherein the NK cell activating ligand cell surface protein is ICAM-1, CEACAM1, CADM1, MICA, MICB or combinations thereof.

Paragraph 4: The method of paragraph 1-2, wherein the NK cell activating ligand is ICAM-1 and CEACAM1.

Paragraph 5: The method of paragraph 1-2, wherein the NK cell activating ligand is ICAM-1, CEACAM1, CADM1, MICA and MICB.

Paragraph 6: A method of depleting hypoimmunogenic cells in a population of cells, said method comprising contacting said hypoimmunogenic cells with a hypoimmunogenic cell depleting composition to effect impairment of the hypoimmunogenic cell function or killing of said hypoimmunogenic cells, thereby depleting said hypoimmunogenic cells in said population of cells.

Paragraph 7: The method of claim 6, wherein the hypoimmunogenic cells lack at least one functional HLA-Class I cell surface protein and at least one NK activating ligand expression.

Paragraph 8: A method of removing hypoimmunogenic cells from a host mammal, said method comprising: (a) transferring hypoimmunogenic cells to said host mammal; and (b) contacting the host with a hypoimmunogenic cell depleting composition to effect impairment of the hypoimmunogenic cell function or killing of said hypoimmunogenic cells, thereby removing said hypoimmunogenic cells in the host mammal.

Paragraph 9: The method of paragraph 8, wherein the function of at least one HLA-Class I cell surface protein and at least one NK activating ligand is diminished.

Paragraph 10: A method of increasing NK activating ligands in a target cell population comprising exposing the target cell population to IFN-γ stimulation thereby increasing NK activating ligands in a target cell compared to wild type.

A method of preparing a hypoimmunogenic stem cell, the method comprising modulating expression of one or more MHC-Class I cell surface proteins and one or more NK activating ligands by the hypoimmunogenic stem cell and thereby preparing the hypoimmunogenic stem cell.

A method of preparing a hypoimmunogenic stem cell, the method comprising modulating expression of one or more MHC-Class I cell surface protein, one or more NK activating ligand and modulating expression of one or more tolerogenic factors on the stem cell and thereby preparing the hypoimmunogenic stem cell.

A method of modulating expression of one or more MHC-Class I cell surface proteins and NK cell activating ligand cell surface proteins on a stem cell, comprising deleting one or more genes encoding one or more transcriptional regulators of MHC-Class I genes and NK cell activating ligands from at least one allele of the cell and thereby modulating expression of the one or more MHC-Class I cell surface proteins and NK cell activating ligand cell surface proteins.

A hypoimmunogenic stem cell comprising a modified genome comprising (a) a first genomic modification in which the B2M gene has been edited to reduce or eliminate B2M surface expression and/or activity in the cell by contacting the cell with a Cas protein or a nucleic acid encoding a Cas protein and a ribonucleic acid comprising a sequence of any one of SEQ ID NOs: 1-3; and (b) a second genomic modification in which the ICAM-1 gene has been edited to reduce or eliminate ICAM-1 surface expression and/or activity in the cell by contacting the cell with a Cas protein or a nucleic acid encoding a Cas protein and a ribonucleic acid comprising a sequence of any one of SEQ ID NOs: 4-6.

A hypoimmunogenic stem cell comprising a modified genome comprising (a) a first genomic modification in which the B2M gene has been edited to reduce or eliminate B2M surface expression and/or activity in the cell by contacting the cell with a Cas protein or a nucleic acid encoding a Cas protein and a ribonucleic acid comprising a sequence of any one of SEQ ID NOs: 1-3; (b) a second genomic modification in which the ICAM-1 gene has been edited to reduce or eliminate ICAM-1 surface expression and/or activity in the cell by contacting the cell with a Cas protein or a nucleic acid encoding a Cas protein and a ribonucleic acid comprising a sequence of any one of SEQ ID NOs: 4-6.; and (c) a third genomic modification in which the CEACAMI gene has been edited to reduce or eliminate CEACAM1 surface expression and/or activity in the cell by contacting the cell with a Cas protein or a nucleic acid encoding a Cas protein and a ribonucleic acid comprising a sequence of any one of SEQ ID NOs: 7-9.

A pluripotent stem cell comprising a modified genome comprising (a) a first genomic modification in which the B2M gene has been edited to reduce or eliminate B2M surface expression and/or activity in the cell by contacting the cell with a Cas protein or a nucleic acid encoding a Cas protein and a ribonucleic acid comprising a sequence of any one of SEQ ID NOs: 1-3; and (b) a second genomic modification in which the ICAM-1 gene has been edited to reduce or eliminate ICAM-1 surface expression and/or activity in the cell by contacting the cell with a Cas protein or a nucleic acid encoding a Cas protein and a ribonucleic acid comprising a sequence of any one of SEQ ID NOs: 4-6.

The sequences of SEQ ID Nos: 1-9 are provided below in Table 4, and described below.

SEQ ID NO. 1: Exon 1, negative strand.

SEQ ID NO. 2: Exon 2, negative strand.

SEQ ID NO. 3: Exon 1, negative strand.

SEQ ID NO. 4: Exon 2, positive strand.

SEQ ID NO. 5: Exon 2, negative strand.

SEQ ID NO. 6: Exon 1, positive strand.

SEQ ID NO. 7: Exon 1, negative strand.

SEQ ID NO. 8: Exon 1, positive strand.

SEQ ID NO. 9: Exon 1, positive strand.

| Gene | Sequences | SEQ.ID NO. |
|---|---|---|
| B2M (beta-2-microglobulin) | CGCGAGCACAGC TAAGGCCACGG | 1 |
| | CAGTAAGTCAAC TTCAATGTCGG | 2 |
| | GAGTAGCGCGAG CACAGCTAAGG | 3 |
| ICAM1 (intercellular adhesion molecule 1) | CCTCAAAAGTCA TCCTGCCCCGG | 4 |
| | AGCAACTCCTTT TTAGGCAACGG | 5 |
| | CCGCACTCCTGG TCCTGCTCGGG | 6 |
| CEACAM1 (carcinoembryonic antigen related cell adhesion molecule 1) | GAGTGCGTGTAC CCTGGCAGGGG | 7 |

-continued

| Gene | Sequences | SEQ.ID NO. |
|---|---|---|
| | GGTACACGCACT CTGTGAAGTGG | 8 |
| | TACACGCACTCT GTGAAGTGGGG | 9 |

A pancreatic endoderm (PEC) cell comprising a modified genome comprising (a) a first genomic modification in which the B2M gene has been edited to reduce or eliminate B2M surface expression and/or activity in the cell by contacting the cell with a Cas protein or a nucleic acid encoding a Cas protein and a ribonucleic acid comprising a sequence of any one of SEQ ID NOs: 1-3; (b) a second genomic modification in which the ICAM-1 gene has been edited to reduce or eliminate ICAM-1 surface expression and/or activity in the cell by contacting the cell with a Cas protein or a nucleic acid encoding a Cas protein and a ribonucleic acid comprising a sequence of any one of SEQ ID NOs: 4-6.; and (c) a third genomic modification in which the CEACAM1 gene has been edited to reduce or eliminate CEACAM1 surface expression and/or activity in the cell by contacting the cell with a Cas protein or a nucleic acid encoding a Cas protein and a ribonucleic acid comprising a sequence of any one of SEQ ID NOs: 7-9.

A method of reducing hypoglycemia, comprising:

a) administering to a subject in need of a transplant, an effective amount of a graft comprising a pancreatic endoderm cell population wherein the function of at least one HLA-Class I cell surface protein and at least one NK cell activating ligand cell surface protein is disrupted wherein the pancreatic endoderm cell population matures in vivo and produces insulin in response to glucose stimulation in vivo, thereby reducing hypoglycemia in a patient.

A method of reducing insulin dependence, comprising:

a) administering to a subject in need of a transplant, an effective amount of a graft comprising a pancreatic endoderm cell population wherein the function of at least one HLA-Class I cell surface protein and at least one NK cell activating ligand cell surface protein is disrupted wherein the pancreatic endoderm cell population matures in vivo and produces insulin in response to glucose stimulation in vivo, thereby reducing insulin dependence in a patient.

Definitions

"Hypoimmunogenic" or "universal donor cells" or "mutant cell" or equivalents thereof means a cell with reduced or eliminated expression of at least one HLA-Class I cell surface protein and at least one NK activating ligand. Such a cell is expected to be less prone to immune rejection or graft rejection by a subject into which such cells or graft are transplanted. For example, relative to an unaltered wild-type cell, such a hypoimmunogenic cell may be about 2.5%, 5%, 10%, 20%, 30%, 40%, 50%, 60%, 70%, 80%, 90%, 95%, 97.5%, 99% or more less prone to immune rejection by a subject into which such cells are transplanted.

The term "treating" or "healing" or equivalents thereof refers to a therapeutic intervention that reduces (ameliorates) a sign or symptom.

The term "patient" or "host" or "mammalian host" or "subject" or equivalents thereof refers to living multi-cellular vertebrate organisms, a category that includes both human and non-human mammals. In some embodiments, the subject is a human subject. The preferred patient for treatment is a human. The target patient populations may change over time of clinical use/experience in ways that are independent of the combination product itself, but rather related to the nature of the immunosuppression regimen or lack thereof. For example, the combination product might be used in a T1D population using a hypoimmunogenic cell therapy in combination with an immuno-suppressive drug (ISD) regimen that achieves operational tolerance or is low in toxicity and side effect profile.

The term "blocking agent" herein refers to any agent capable of binding to an NK activating ligand on the surface of a target cell including but not limited to an antibody; or refers to an agent that prevents or inhibits protein expression of an NK activating ligand including but not limited to a protein, an enzyme or chemical presently known or later to be developed.

The term "antibody" herein is used in the broadest sense and specifically covers intact monoclonal antibodies, poly-clonal antibodies, multispecific antibodies (e.g., bispecific antibodies) formed from at least two intact antibodies, and antibody fragments so long as they exhibit the desired biological blocking activity.

The term "antibody fragments" used herein refers to a portion of an intact antibody, preferably comprising the antigen-binding or variable region thereof. Examples of antibody fragments include Fab, Fab', F(ab')2, and Fv frag-ments, diabodies, linear antibodies, single-chain antibody molecules, and multispecific antibodies formed from anti-body fragments.

The term "blocking antibody" used herein refers to an antibody that, when it binds to an NK cell activating ligand on the target cell in vivo or in vitro, results in preventing or lessening the ability of the NK cell to lyse the target cell.

As used herein, the term "syngenic" or "syngeneic" refers to cells, tissues or organs that are genetically identical or are derived from a genetically identical source to the transplant recipient {e.g., an identical twin), especially with respect to antigens or immunological reactions. Such cells, tissues or organs are called isografts. As used herein, the term "allo-genic" or "allogeneic" refers to cells, tissues or organs that are not genetically identical or are derived from a non-genetically identical source to the transplant recipient (e.g., a non-related donor), especially with respect to antigens or immunological reactions. Such cells, tissues or organs are called allografts, allogeneic transplants, homografts or allotransplants.

As used herein, the term "promoter/regulatory sequence" means a nucleic acid sequence which is required for expres-sion of a gene product operably linked to the promoter/ regulator sequence. In some instances, this sequence may be the core promoter sequence and in other instances, this sequence may also include an enhancer sequence and other regulatory elements which are required for expression of the gene product. The promoter/regulatory sequence may, for example, be one which expresses the gene product in a tissue specific manner.

The term "effective amount" or "therapeutically effective amount" or equivalents thereof refers to a quantity of an agent sufficient to achieve a desired effect in a subject or a cell being treated. For instance, this can be the amount of cells necessary to inhibit or to measurably reduce blood glucose levels and ultimately achieve homeostatic glycemic control. It can also mean an effective amount of an agent to change the function or structure of a cell or subject. A therapeutically effective amount of an agent may be admin-istered in a single dose, or in several doses. However, the effective amount will be dependent on the particular agent applied, the subject being treated, the severity and type of the affliction, and the manner of administration.

The terms "decrease," "disrupted," "reduced," "reduc-tion," and "inhibit" are all used herein generally to mean a decrease, specifically, decrease by a statistically significant amount. However, for avoidance of doubt, "decreased," "reduced," "reduction," "inhibited" includes a decrease by at least 10% as compared to a reference level, for example a decrease by at least about 20%, or at least about 30%, or at least about 40%, or at least about 50%, or at least about 60%, or at least about 70%, or at least about 80%, or at least about 90% or up to and including a 100% decrease (i.e. absent level as compared to a reference sample), or any decrease between 10-100% as compared to a reference level, or at least about a 2-fold, or at least about a 3-fold, or at least about a 4-fold, or at least about a 5-fold, or at least about a 10-fold decrease, or any decrease between 2-fold and 10-fold or greater as compared to a reference level.

The terms "increased," "increase" or "enhance" or "acti-vate" are all used herein to generally mean an increase by a statically significant amount; for the avoidance of any doubt, the terms "increased", "increase" or "enhance" or "activate" means an increase of at least 10% as compared to a reference level, for example an increase of at least about 20%, or at least about 30%, or at least about 40%, or at least about 50%, or at least about 60%, or at least about 70%, or at least about 80%, or at least about 90%, or up to and including a 100% increase, or any increase between 10-100% as compared to a reference level, or at least about a 2-fold, or at least about a 3-fold, or at least about a 4-fold, or at least about a 5-fold, or at least about a 10-fold increase, or any increase between 2-fold and 10-fold or greater as compared to a reference level.

The term "statistically significant" or "significantly" refers to statistical significance and generally means a two standard deviation (2SD) below normal, or lower, concen-tration of a reference. The term can also mean two standard deviation (2SD) above normal, or higher, concentration of the reference. The term refers to statistical evidence that there is a difference. It is defined as the probability of making a decision to reject the null hypothesis when the null hypothesis is actually true. The decision is often made using the p-value.

As used herein, "reduced hypoglycemia" or equivalents thereof means a reduction in the number of hypoglycemic episodes together with no deterioration in glycemic control, defined by ≤0.2% increase in HbA1c.

As used herein "reduced insulin dependence" or equiva-lents thereof means a reduction in the number and/or dose of exogenous insulin injections together with no deterioration in glycemic control, defined by ≤0.2% increase in HbA1c.

As used herein "tissue capsule" or equivalents thereof means the foreign body capsule that forms around an implant or graft. The combination product and/or device or perforated device containing the cells are intended to be retained within the capsule during the implant period.

"Engraftment" or equivalents thereof refers to differen-tiation of a progenitor or immature cell population into a mature cell type. For example, engraftment of a PDX1-positive pancreatic endoderm cell population maturing into a pancreatic endocrine cell population.

"Graft" refers to a differentiated cell population encapsu-lated or delivered in the devices herein. For example, cell populations including but not limited to a pancreatic endo-derm, a pancreatic progenitor, a PDX-1 positive pancreatic endoderm, a pancreatic endocrine precursor, pancreatic endocrine, singly or polyhormonal endocrine, pre-beta, beta, and/or insulin secreting grafts.

The term "essentially" or "substantially" or equivalents thereof means mostly or a de minimus or a reduced amount of a component or cell present in any cell population or culture, e.g., immature beta cell cultures are "essentially or substantially immature beta cells expressing INS, NKX6.1 and PDX1 and not essentially or substantially expressing NGN3". Other examples include but not limited to "essentially or substantially hES cells", "essentially or substantially definitive endoderm cells", "essentially or substantially foregut endoderm cells", "essentially or substantially PDX1-negative foregut endoderm cells", "essentially or substantially PDX1-positive pancreatic endoderm cells", "essentially or substantially pancreatic endocrine precursor cells", "essentially or substantially pancreatic endocrine cells" and the like.

With respect to cells in cell cultures or in cell populations, the term "substantially free of" or equivalents thereof means that the specified cell type of which the cell culture or cell population is free, is present in an amount of less than about 10%, less than about 9%, less than about 8%, less than about 7%, less than about 6%, less than about 5%, less than about 4%, less than about 3%, less than about 2% or less than about 1% of the total number of cells present in the cell culture or cell population.

The term "non-woven fabric" or equivalents thereof, includes, but is not limited to, bonded fabrics, formed fabrics, or engineered fabrics, that are manufactured by processes other than, weaving or knitting.

It is to be understood that the inventions disclosed herein are not limited in their application to the details set forth in the description or as exemplified. The invention encompasses other embodiments and is capable of being practiced or carried out in various ways. Also, it is to be understood that the phraseology and terminology employed herein is for the purpose of description and should not be regarded as limiting.

While certain compositions, methods and assays of the present invention have been described with specificity in accordance with certain embodiments, the following examples serve only to illustrate the methods and compositions of the invention and are not intended to limit the same.

The articles "a" and "an" as used herein in the specification and in the claims, unless clearly indicated to the contrary, should be understood to include the plural referents. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention also includes embodiments in which more than one, or the entire group members are present in, employed in, or otherwise relevant to a given product or process.

Furthermore, it is to be understood that the invention encompasses all variations, combinations, and permutations in which one or more limitations, elements, clauses, descriptive terms, etc., from one or more of the listed claims is introduced into another claim dependent on the same base claim (or, as relevant, any other claim) unless otherwise indicated or unless it would be evident to one of ordinary skill in the art that a contradiction or inconsistency would arise. Where elements are presented as lists, (e.g., in Markush group or similar format) it is to be understood that each subgroup of the elements is also disclosed, and any element(s) can be removed from the group. It should be understood that, in general, where the invention, or aspects of the invention, is/are referred to as comprising particular elements, features, etc., certain embodiments of the invention or aspects of the invention consist, or consist essentially of, such elements, features, etc. For purposes of simplicity those embodiments have not in every case been specifically set forth in so many words herein. It should also be understood that any embodiment or aspect of the invention can be explicitly excluded from the claims, regardless of whether the specific exclusion is recited in the specification. The publications and other reference materials referenced herein to describe the background of the invention and to provide additional detail regarding its practice are hereby incorporated by reference.

EXAMPLES

Example 1: Generation of B2M Deficient HES Cells

B2M deficient hES cells were generated using CyT49 cell line, however, any human pluripotent stem cell line can be used. Targeted disruption of B2M gene generated cells, which do not express any HLA-Class I proteins on their cell surface. Both alleles of the B2M locus in the CyT49 hESC line were disrupted using CRISPR/Cas9 technology using known techniques as outlined in PCT Publication No. WO2016183041A (which is incorporated herein in its entirety). However, other nucleases including zinc-finger nucleases (ZFN) and transcription activator-like effector nuclease (TALEN) can be used to edit genes, as well traditional homologous recombination and the like. Examples of published sequences for B2M are submitted as SEQ ID NOS.: 1, 2, and 3. NEXTGEN™ CRISPR (Transposagen Inc., Lexington Kentucky) was used to edit the gene, which incorporates dual guide RNA's and a catalytically inactive Cas9 protein fused to the FokI nuclease. Plasmids containing the guide RNA's and Cas9 were electroporated into CyT49 hESC, and cells were seeded onto tissue culture plates. Twelve days post-electroporation, cells were sorted for negative reactivity to a B2M antibody (BioLegend Cat #316306) by fluorescence activated cell sorting (FACS). Sorted cells were plated at clonal density. Individual clones were picked and plated at about day 25. Clones were expanded and cryopreserved. Expanded clones that showed a normal karyotype by G-banding, and were negative for expression of B2M protein and for surface expression of HLA-class I proteins by flow cytometry and/or immunofluorescence were chosen for further experimentation.

B2M surface expression in wild type (WT) and knockout cells was assessed by flow cytometry under normal and inflammatory conditions (after exposure to interferon (IFN)-γ). See FIG. 2A: Normal: untreated growth media (Line B); inflammatory: exposed to 100 ng/ml of IFN-γ for 18-24 hours (Line A). Inflammatory response occurs in relation to tissue trauma. This releases proinflammatory cytokines, some of which are IL-1-α, IL-1-β, TNF-α, IL-6, IL-8 and IFN-γ. Although WT and B2M−/− ESC and PEC have been treated with IFN-γ, these observations can be extended with other cytokines as well.

Figure 2A:
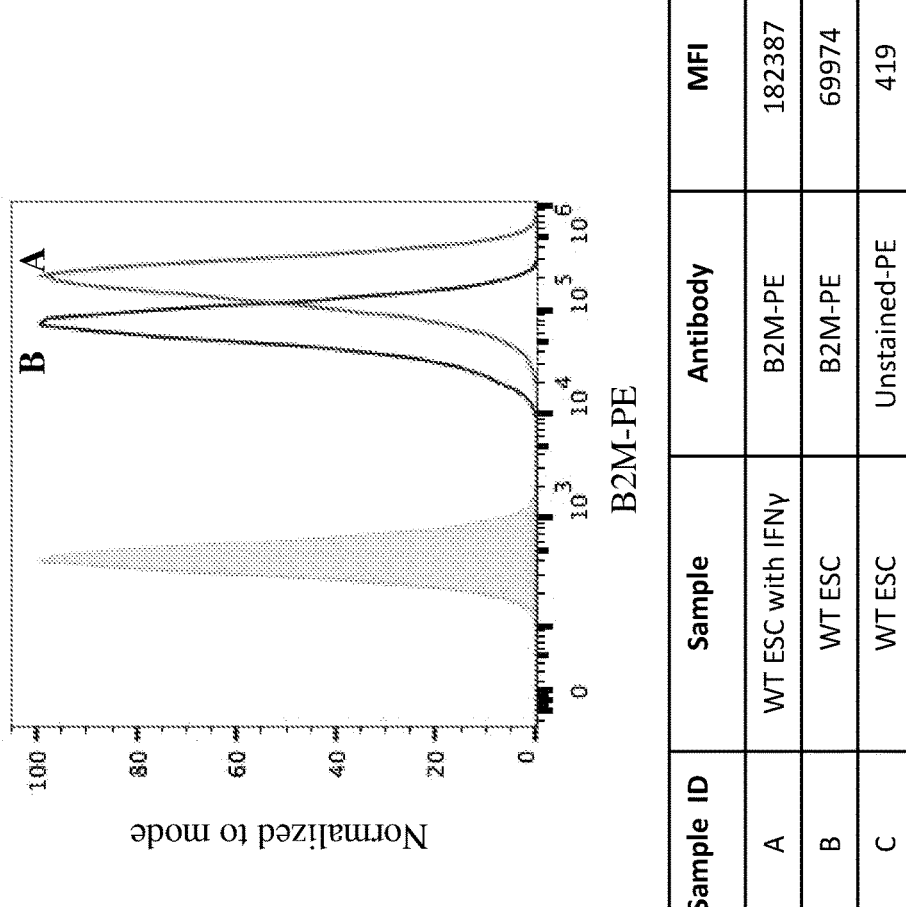
FIG. 2A shows representative flow cytometry analysis of B2M cell surface protein expression on wild-type (WT) hES cells without IFN-γ (Line B) and after exposure to IFN-γ (Line A). The shaded region is background expression with no antibody staining. Exposure to IFN-γ increases B2M cell surface protein expression in WT hES cells.

FIG. 2A shows B2M expression in WT hES cells (Line B) without IFN-γ and B2M expression following exposure of WT hES cells with IFN-γ (Line A). The shift (increase) in florescent intensity in the untreated WT hES cells (Line B) as compared to background (shaded region) indicates that WT hES cells express B2M. The further shift (increase) in florescent intensity beyond WT B2M expression (Line B) following exposure of WT hES cells to IFN-γ suggests that B2M expression increases in WT hES cells following exposure to IFN-γ (Line A). As such expression of HLA-Class I cell surface proteins can be upregulated upon cellular stress and inflammation such as that caused by at least IFN-γ treatment.

Figure 2B:
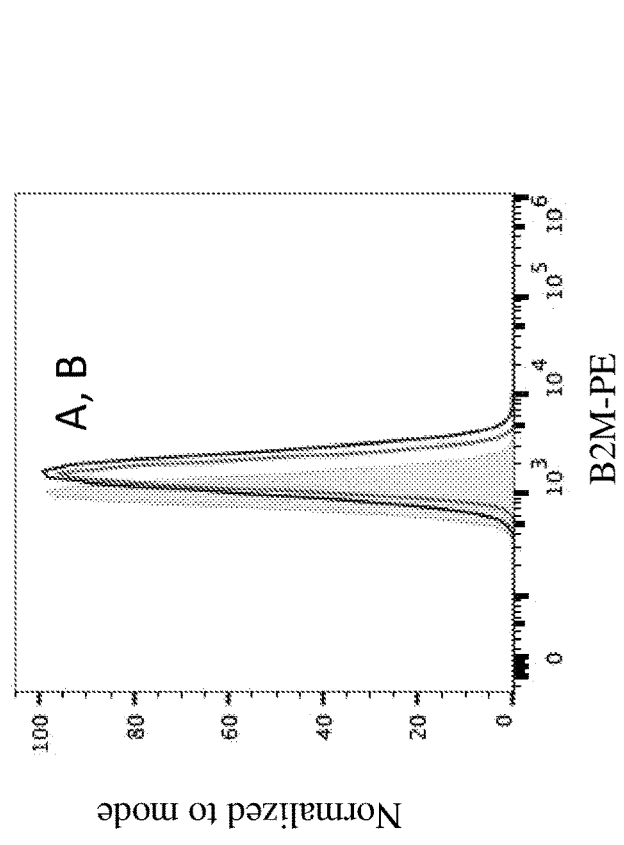
FIG. 2B shows representative flow cytometry analysis of B2M cell surface protein expression on B2M knockout (B2M−/−) hES cells without IFN-γ (Line B) and after exposure to IFN-γ (Line A). B2M−/− hES cells have very little B2M cell surface protein expression which does not significantly change after exposure to IFN-γ.

FIG. 2B shows B2M expression in B2M knockout hES cells, knockout cells were generated using the CRISPR/Cas system. There is substantially no shift (increase) in florescent intensity as compared to the background (shaded region) with or without exposure to IFN-γ suggesting the B2M knockout hES cells had reduced or eliminated B2M surface expression and that expression of B2M could not be induced by IFN-γ treatment. In such B2M knockouts, expression of HLA-Class I cell surface proteins is not upregulated upon cellular stress and inflammation caused by IFN-γ treatment.

This example demonstrates that B2M knockout hES cells had reduced or eliminated B2M surface expression as shown using a B2M antibody.

Example 2: Analysis of HLA Class I Cell Surface Protein Expression in WT and B2M Deficient Cells Next, wild type and B2M knockout hES cells were analyzed using a Pan-HLA-ABC monoclonal antibody (BD Pharmingen, cat #560169) to confirm that these knockout cells did not express HLA-Class I proteins on the cell surface. The Pan-HLA-ABC a ntibody reacts with the human major histocompatibility complex (MHC) class I proteins, HLA-A, -B, and -C. Expression of Pan-HLA-ABC antibody was assessed in wild type and knockout cells by flow cytometry under normal and inflammatory states after exposure to IFN-γ. Normal: without IFN-γ (Line B); inflammatory: exposed to 100 ng/ml of IFN-γ for 18-24 hours (Line A).

Figure 3A:
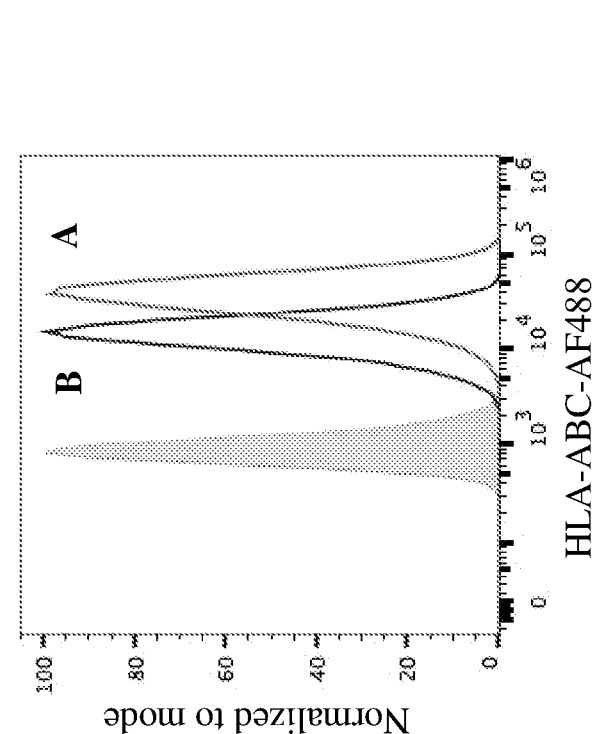
FIG. 3A shows representative flow cytometry analysis of HLA-ABC cell surface protein expression on WT hES cells without IFN-γ (Line B) and after exposure to IFN-γ (Line A) using pan HLA Class I antibody. The shaded region is background expression with no antibody staining.

FIG. 3A shows Pan-HLA-ABC cell surface protein expression in WT hES cells (Line B) and Pan-HLA-ABC cell surface protein expression following treatment of WT hES cells with IFN-γ (Line A). The shift (increase) in florescent intensity in the untreated WT hES cells (Line B) as compared to background (shaded region) suggests that WT hES cells express Pan-HLA-ABC. The shift (increase) in florescent intensity beyond WT hES expression following exposure to IFN-γ suggests that Pan-HLA-ABC expression increases in WT hES cells following exposure to IFN-γ.

Figure 3B:
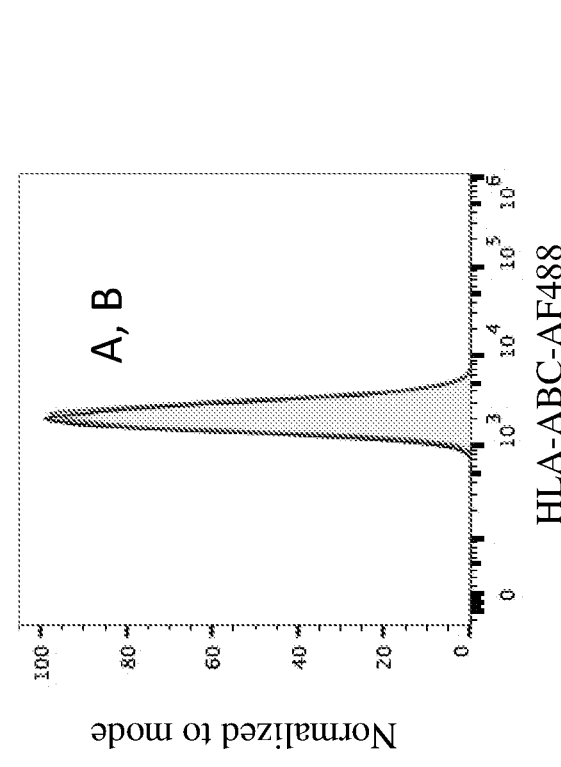
FIG. 3B shows representative flow cytometry analysis of HLA-ABC cell surface protein expression on B2M knockout hES cells without IFN-γ (Line B) and after exposure to IFN-γ (Line A). B2M−/− hES cells have no detectable HLA-ABC cell surface protein expression.

FIG. 3B shows Pan-HLA-ABC cell surface protein expression in B2M knockout hES cells using the CRISPR/Cas system. There is no shift (increase) in florescent intensity as compared to background (shaded region) with or without exposure to IFN-γ suggesting the knockouts had reduced or eliminated HLA-Class I cell surface expression and that expression of HLA-Class I proteins was not induced by IFN-γ treatment.

This example demonstrates that B2M knockout hES cells had reduced or eliminated HLA-Class I cell surface expression as shown using a Pan-HLA-ABC antibody.

Example 3: Differentiation of B2M Deficient Cells to Pancreatic Lineage Cells B2M knockout hES cells were cultured, passaged and proliferated under the same conditions as WT hES cells as described in Schulz et al. A Scalable System for Production of Functional Pancreatic Progenitors from Human Embryonic Stem Cells PLOS One 7:5 1-17 (2012) and as described in U.S. Pat. No. 8,895,300 which are both herein incorporated by reference in their entireties. Specifically, Schulz et. al. describe adherent hESC expansion and suspension-based differentiation.

WT hES cells and B2M−/− hES cells were differentiated in suspension aggregates using a four (4) stage procedure over the course of about 2 weeks (or 14 days) to generate a population of pancreatic cell types including pancreatic progenitors, endocrine progenitors and hormone expressing cells, collectively referred to as pancreatic endoderm cells (PEC). Human ES cells were dissociated using accutase and single cells were aggregated in roller bottles. To initiate differentiation, aggregates were pooled into conical tube(s) and allowed to settle by gravity, followed by a wash using Stage-1 media without growth factors (RPMI+0.2% vol/vol FBS containing 1:5000 dilution of insulin-transferrin-selenium (ITS)). The aggregates were re-settled, then resuspended in day 1 media which comprises of RPMI+0.2% vol/vol FBS containing 1:5000 dilution of insulin-transferrin-selenium (ITS), activin A (100 ng/mL) and wnt3a (50 ng/mL), and distributed to the roller bottles at a density of 2 uL/mL. The roller bottles were placed on FlexiRoll digital cell roller (Argos Technologies) at a speed of 31 rpm. Cultures were rotated at about 31 rpm for the remainder of the differentiation process with daily media exchange to those described in Table 2 below, adapted from Schulz et al., (2012), supra. Growth, passaging and proliferation of hES is substantially as described in U.S. Pat. Nos. 7,964,402; 8,211,699; 8,334,138; 8,008,07; and 8,153,429. A standard manufacturing method used for making pancreatic endoderm cells (PEC) derived from human embryonic stem cells is provided below in Table 2.

TABLE 2

| Standard Manufacturing Method For Making Pancreatic Endoderm Cells (PEC) Derived From hESC | | | | |
|---|---|---|---|---|
| Time point (day) | Stage (1-4) | Media Condition | Roller Bottle Speed (rpm) | 6-well tray Speed (rpm) |
| d(−1) | hESC Agg. | XF HA; SP | 31 | 95 |
| d 0 | 1 | r0.2FBS-ITS1:5000 A100 W50 | 31 | 95 |
| d 1 | | r0.2FBS-ITS1:5000 A100 | 31 | 95 |
| d 2 | 2 | r0.2FBS-ITS1:1000 K25 IV | 31 | 95 |
| d 3 | | r0.2FBS-ITS1:1000 K25 | 31 | 95 |
| d 4 | | r0.2FBS-ITS1:1000 K25 | 31 | 105 |
| d 5 | 3 | db-CTT3 N50 | 31 | 105 |
| d 6 | | db-CTT3 N50 | 31 | 105 |
| d 7 | | db-CTT3 N50 | 31 | 105 |
| d 8 | 4 | db-N50 K50 E50 | 31 | 105 |
| d 9 | | db-N50 K50 E50 | 31 | 95 |
| d 10 | | db-N50 K50 E50 | 31 | 95 |
| d 11 | | db-N50 K50 E50 | 31 | 95 |
| d 12 | | db-N50 K50 E50 | 31 | 95 | hESC Agg.: hESC aggregates; XF HA: DMEM/F12 containing GlutaMAX, supplemented with 10% v/v of Xeno-free KnockOut Serum Replacement, 1% v/v non-essential amino acids, 1% v/v penicillin/streptomycin (all from Life Technologies), 10 ng/mL heregulin-1β (Peprotech) and 10 ng/mL activin A (R&D Systems); SP: StemPro ® hESC SFM (Life Technologies); r0.2FBS: RPMI 1640 (Mediatech); 0.2% FBS (HyClone), 1x GlutaMAX-1 (Life Technologies), 1% v/v penicillin/streptomycin; ITS: Insulin-Transferrin-Selenium (Life Technologies) diluted 1:5000 or 1:1000; A100: 100 ng/mL recombinant human Activin A (R&D Systems); W50: 50 ng/mL recombinant mouse Wnt3A (R&D Systems); K25: 25 ng/mL recombinant human KGF (R&D Systems); IV: 2.5 μM TGF-β RI Kinase inhibitor IV (EMD Bioscience); db: DMEM HI Glucose (HyClone) supplemented with 0.5x B-27 Supplement (Life Technologies), 1x GlutaMAX, and 1% v/v penicillin/streptomycin; CTT3: 0.25 μM KAAD-Cyclopamine (Toronto Research Chemicals) and 3 nM TTNPB (Sigma-Aldrich); N50: 50 ng/mL recombinant human Noggin (R&D Systems); K50: 50 ng/mL recombinant human KGF (R&D Systems); E50: 50 ng/mL recombinant human EGF (R&D Systems).

Differentiated B2M–/– and WT PEC were analyzed using flow cytometry to determine the relative amount of endocrine and pancreatic progenitor cells in the population at stage 4 as shown in Table 3.

TABLE 3

| | | | CHGA– |
| | | | NKX6.1– |
| | CHGA– | CHGA– | PDX1– |
| | NKX6.1+PDX1+ | NKX6.1– | (Triple |
| | or – | PDX1+ | negative; |
| CHGA+ | (Pancreatic | (PDX+ | residual cells) |
| Cell line | (Endocrine) | Progenitors) | only) | |
|---|---|---|---|---|
| Stage 4 Pancreatic Progenitor Cell Compositions (Percent of total Cells) | | | | |
| WT | 44 | 42 | 11 | 2 |
| B2M–/– clone1 | 41 | 52 | 5 | 1 |
| B2M–/– clone2 | 41 | 51 | 7 | 1 |
| B2M–/– clone3 | 41 | 53 | 5 | 1 |

The relative levels of pancreatic endocrine cells, progenitors, PDX-1 only cells and triple negative cells in the B2M–/– differentiated cells in all 3 clones is substantially similar to that observed in WT cells (top row).

This example demonstrates that the B2M–/– hES cells can differentiate down the pancreatic lineage the same as WT hES cells.

Example 4: Analysis of B2M Expression in WT and B2M Deficient Pancreatic Endoderm Cells Next, wild type and B2M knockout pancreatic endoderm cells (PEC) from Example 3 were analyzed using flow cytometry without and with IFN-γ treatment: without IFN-γ (Line B); exposed to 100 ng/ml of IFN-γ for 18-24 hours (Line A).

Figure 4A:
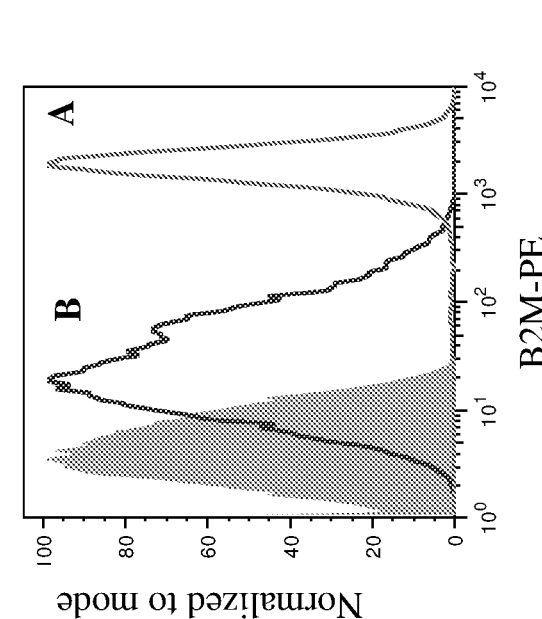
FIG. 4A shows representative flow cytometry analysis of B2M cell surface protein expression on WT pancreatic endoderm cells (PEC) without IFN-γ (Line B) and after exposure to IFN-γ (Line A). The shaded region is background expression with no antibody staining. Exposure to IFN-γ increases B2M cell surface protein expression in WT PEC.
Figure 4B:
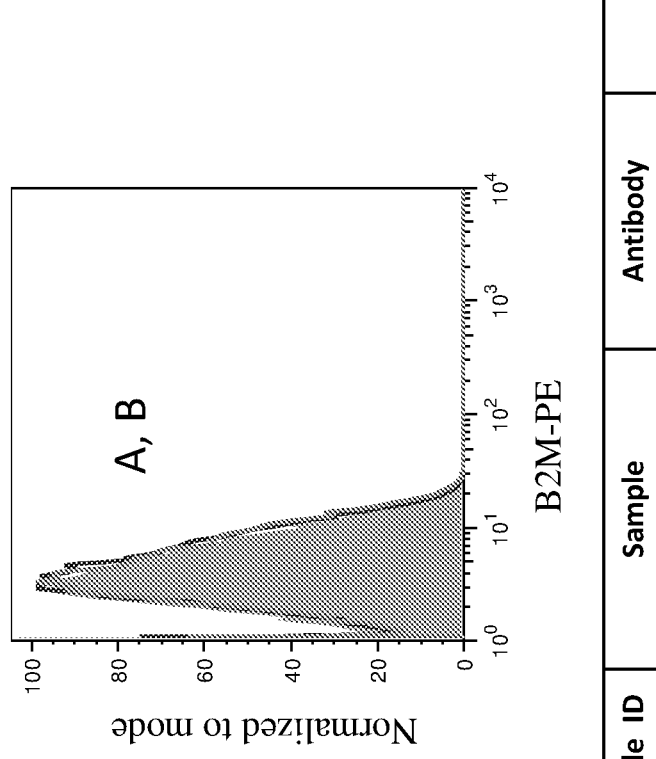
FIG. 4B shows representative flow cytometry analysis of B2M cell surface protein expression on B2M knockout PEC without IFN-γ (Line B) and after exposure to IFN-γ (Line A). B2M−/− PEC have no detectable B2M cell surface protein expression.

FIG. 4A shows B2M expression in WT PEC cells without (Line B) and following treatment with IFN-γ (Line A). The shift (increase) in florescent intensity in the untreated WT PEC cells (Line B) compared to background (shaded region) indicates that WT PEC cells express B2M. The shift (increase) in florescent intensity beyond WT expression following exposure of WT PEC to IFN-γ (Line A) indicates that B2M expression increases in WT PEC cells following exposure to IFN-γ. That is, exposure to IFN-γ increases B2M expression in WT PEC.

FIG. 4B shows B2M expression in PEC cells derived from B2M knockout hES cells. There is no shift (increase) in florescent intensity as compared to the background (shaded region) with or without exposure to IFN-γ, suggesting the B2M knockout PEC had reduced or eliminated B2M cell surface expression and that expression of B2M could not be induced in B2M knockout hES-cell derived PEC by IFN-γ treatment.

This example shows PEC derived from hES cells in which the expression of B2M was modulated/eliminated had reduced or eliminated B2M surface expression.

Example 5: Analysis of HLA Class I Cell Surface Protein Expression in WT and B2M Knockout Pancreatic Endoderm Cells Similar to Example 2, wild type and B2M knockout PEC were analyzed using a Pan-HLA-ABC monoclonal antibody (BD Pharmingen, cat #560169) for HLA Class I cell surface expression. Expression was assessed in wild type and knockout cells by flow cytometry under two conditions (1) untreated (Line B) and (2) treated with 100 ng/ml of IFN-γ for 18-24 hours (Line A).

Figure 5A:
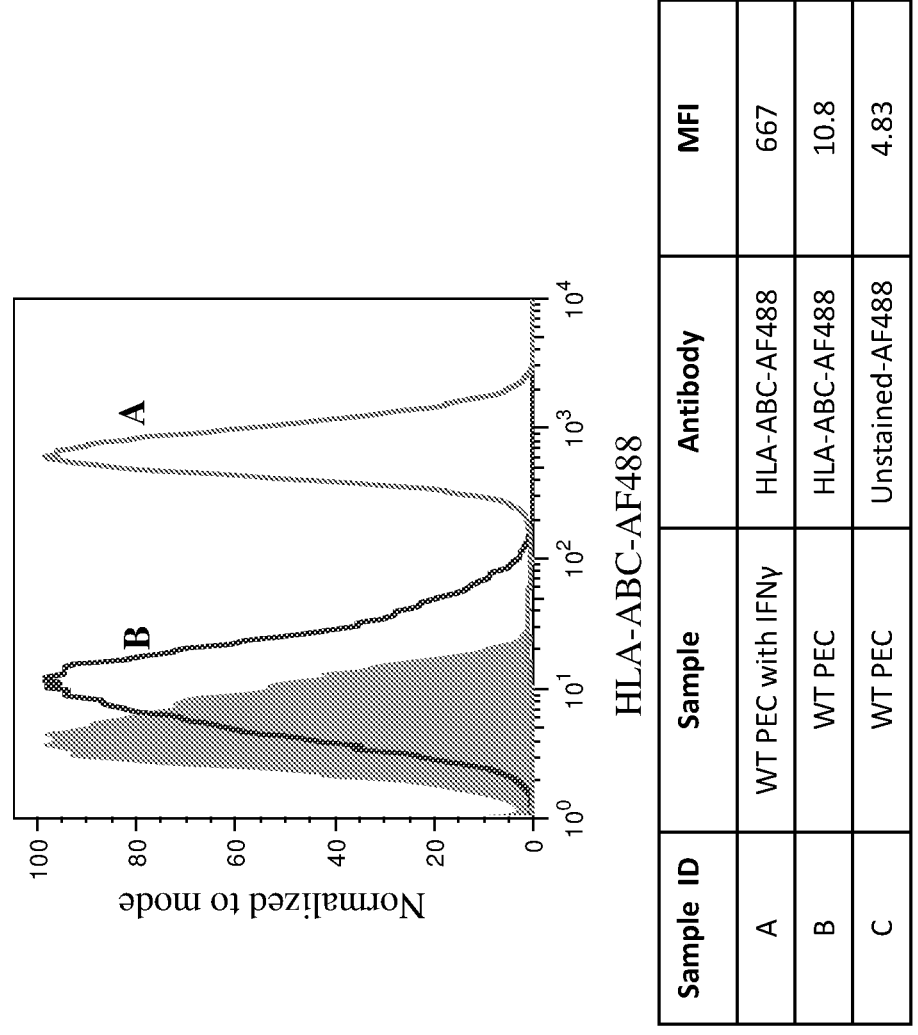
FIG. 5A shows representative flow cytometry analysis of HLA-ABC cell surface protein expression on WT PEC without IFN-γ (Line B) and after exposure to IFN-γ (Line A). The shaded region is background expression with no antibody staining. Exposure to IFN-γ increases HLA-ABC cell surface protein expression in WT PEC.
Figure 5B:
FIG. 5B shows representative flow cytometry analysis of HLA-ABC cell surface protein expression on B2M knockout PEC without IFN-γ (Line B) and after exposure to IFN-γ (Line A). B2M−/− PEC have no detectable HLA-ABC cell surface protein expression.

FIG. 5A shows HLA-Class I cell surface protein expression in WT PEC under untreated condition (Line B) and expression following treatment with IFN-γ (Line A). The shift (increase) in florescent intensity in the untreated WT PEC (Line B) as compared to the background (shaded region) indicates that WT PEC express HLA-Class I on the cell surface. The shift (increase) in florescent intensity beyond WT PEC expression following exposure to IFN-γ suggests that HLA Class I cell surface expression increases in WT PEC cells following exposure to IFN-γ.

FIG. 5B shows HLA-Class I cell surface protein expression in PEC derived from B2M knockout hES cells. There is no shift (increase) in florescent intensity as compared to the background (shaded region) in PEC cells with or without exposure to IFN-γ suggesting the knockout had reduced or eliminated HLA surface expression and that expression of HLA Class I n B2M–/– PEC could not be induced by IFN-γ treatment.

As such, reduced or eliminated HLA Class I cell surface expression was observed in those PEC cells in which the expression of B2M was modulated/eliminated.

Example 6: Analysis of ICAM-1 Cell Surface Protein Expression in WT and B2M Knockout HES Cells To further define the effect of IFN-γ treatment on target cells, ICAM-1 expression in WT and B2M knockout hES cells was assessed by flow cytometry under two conditions: (1) untreated (Line B) and (2) treated with 100 ng/mL of IFN-γ for 18-24 hours (Line A). ICAM-1 is required for several immunological functions including antigen presentation in target cells, and is a known NK activating ligand. In vivo, it is possible to derive immunological benefits by disrupting the intercellular ICAM/LFA binding interaction through the application of specific monoclonal antibodies ("mAbs"), i.e., anti-ICAM-1 or anti-LFA-1. See Isobe et al., Specific Acceptance of Cardiac Allograft After Treatment With Antibodies to ICAM-1 and LFA-1, 255 SCIENCE 1125-1127 (Feb. 1992). Applicants used ICAM-1 antibody from Milteney Biotec Inc., cat #130-103-909.

Figure 6A:
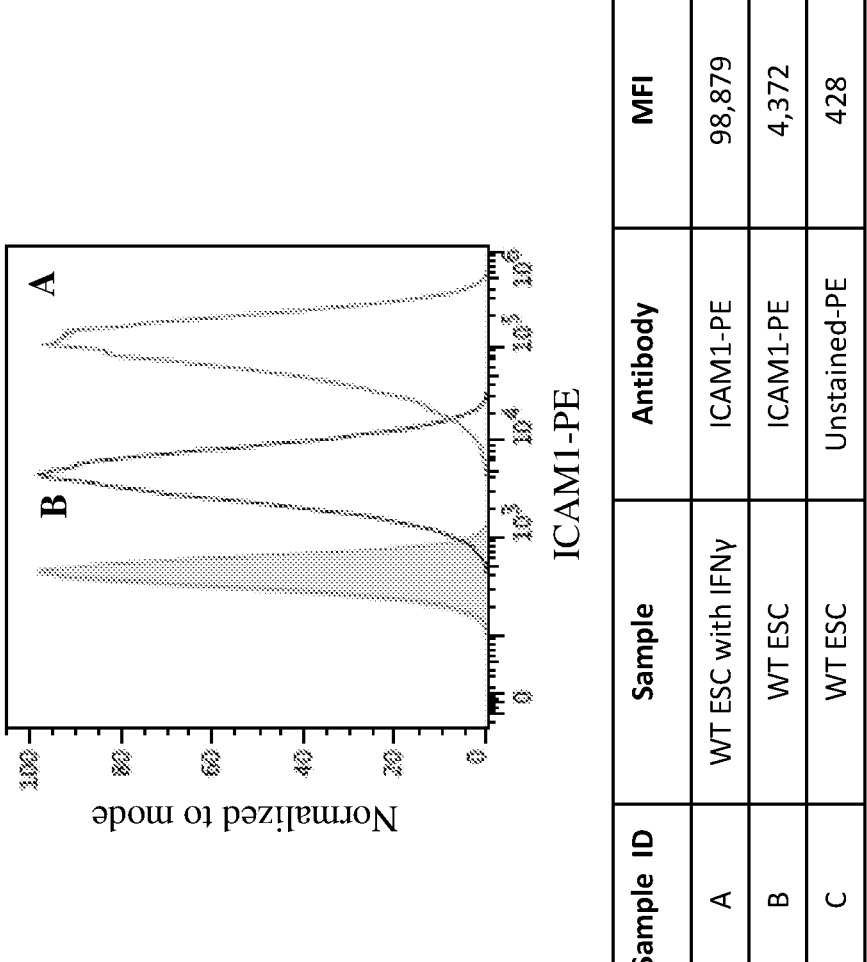
FIG. 6A shows representative flow cytometry analysis of ICAM-1 cell surface protein expression on WT hES cells without IFN-γ (Line B) and after exposure to IFN-γ (Line A). The shaded region is background expression with no antibody staining. Exposure to IFN-γ increases ICAM-1 cell surface protein expression in WT hES cells.

FIG. 6A shows ICAM-1 protein expression on the cell surface in WT hES cells in untreated (Line B) and following treatment with IFN-γ (Line A). The shift (increase) in florescent intensity as compared to the background (shaded region) in untreated WT hES cell (Line B) indicates that WT hES cells express ICAM-1 protein on their cell surface. The shift (increase) in florescent intensity beyond WT expression following exposure of WT hES cells to IFN-γ suggests that ICAM-1 expression increases following exposure to IFN-γ.

Figure 6B:
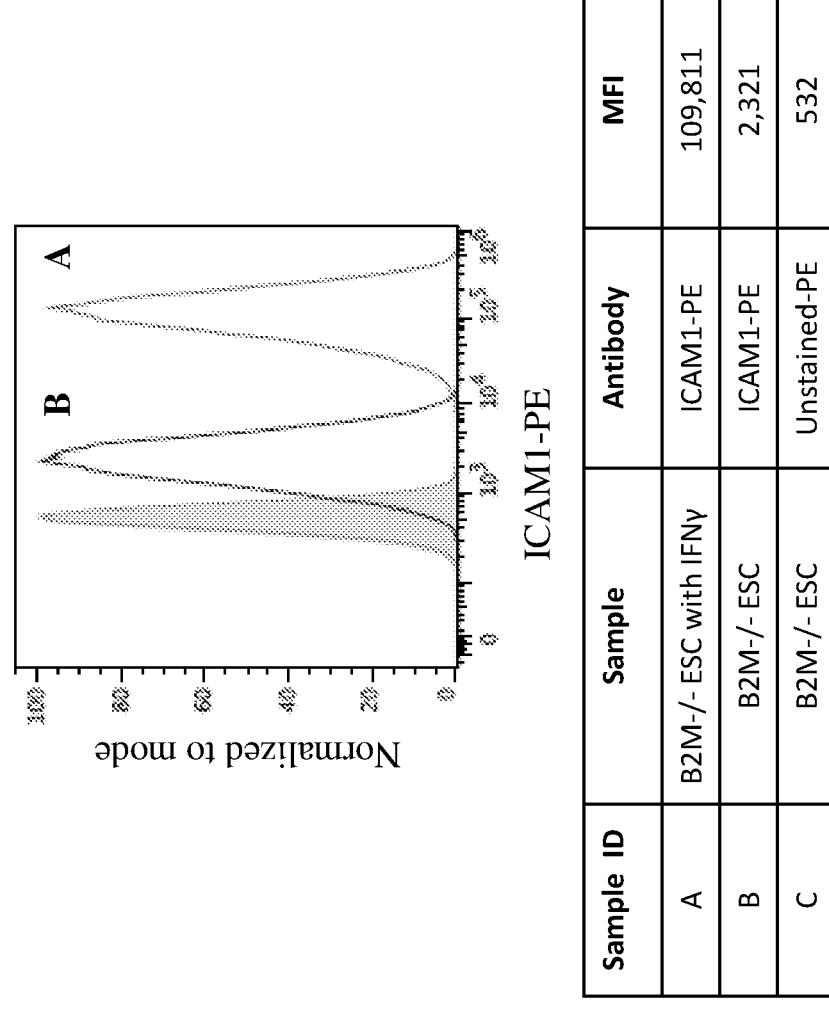
FIG. 6B shows representative flow cytometry analysis of ICAM-1 cell surface protein expression on B2M knockout hES cells without IFN-γ (Line B) and after exposure to IFN-γ (Line A). B2M−/− hES cells have similar ICAM-1 cell surface protein expression as WT hES cells, before and after IFN-γ exposure.

FIG. 6B shows ICAM-1 cell surface protein expression in B2M knockout hES cells in untreated (Line B) and following treatment with IFN-γ (Line A). FIG. 6B shows that ICAM-1 cell surface protein expression in the B2M knockout hES cells was similar to WT hES cells.

This example demonstrates that treatment of WT and B2M knockout hES cells with IFN-γ increases cell surface protein expression of ICAM-1.

Example 7: Analysis of ICAM-1 Cell Surface Protein Expression in WT and B2M Knockout Pancreatic Endoderm Cells Similar to Examples 4 and 5, wild type and B2M knockout PEC were analyzed using an antibody to a known NK activating ligand, e.g. ICAM-1. Cell surface protein expression of ICAM-1 was assessed in WT and knockout PEC by flow cytometry under two conditions (1) untreated and (2) treated with 100 ng/mL of IFN-γ for 18-24 hours.

Figure 7A:
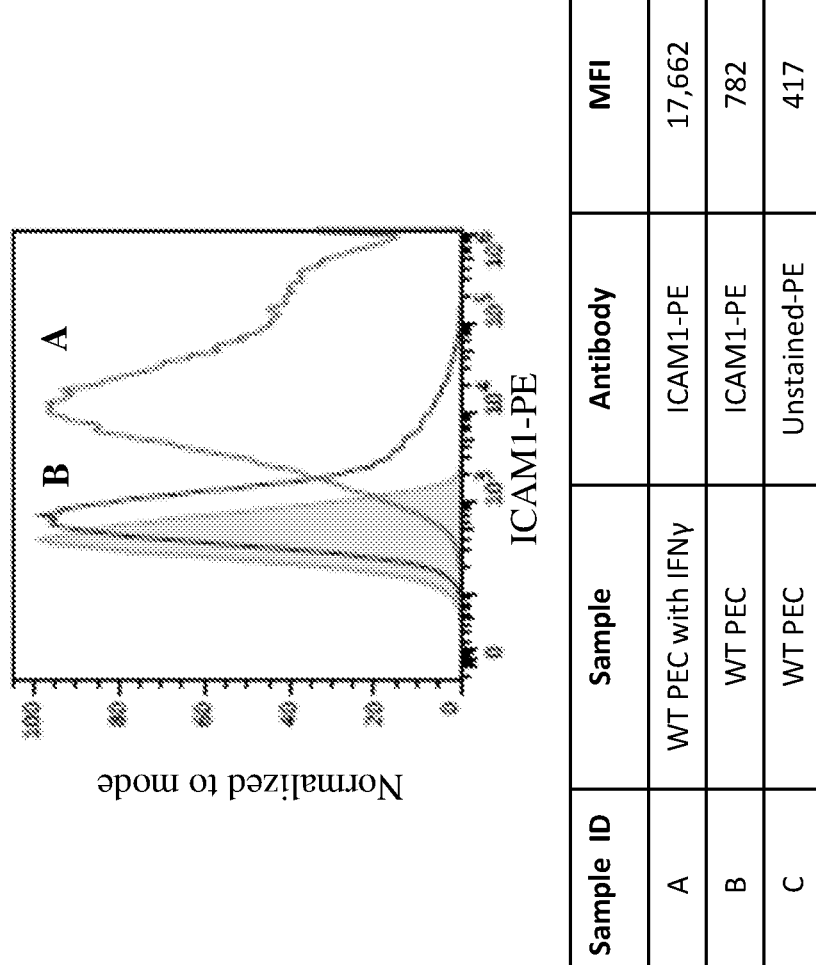
FIG. 7A shows representative flow cytometry analysis of ICAM-1 cell surface protein expression on WT PEC without IFN-γ (Line B) and after exposure to IFN-γ (Line A). The shaded region is background expression with no antibody staining. Exposure to IFN-γ increases ICAM-1 cell surface protein expression in WT PEC.

FIG. 7A shows ICAM-1 cell surface protein expression in WT PEC (Line B) and ICAM-1 cell surface protein expression following treatment of WT PEC with IFN-γ (Line A). The shift (increase) in florescent intensity in the untreated WT PEC (line B) compared to the background (shaded region) indicates that WT PEC express ICAM-1 protein on their cell surface. The further shift (increase) in florescent intensity beyond WT PEC expression following exposure to IFN-γ suggests that ICAM-1 expression increases in WT PEC following exposure to IFN-γ. This demonstrates that NK activating ligands, and in particular ICAM-1, are highly inducible by IFN-γ stimulation.

Figure 7B:
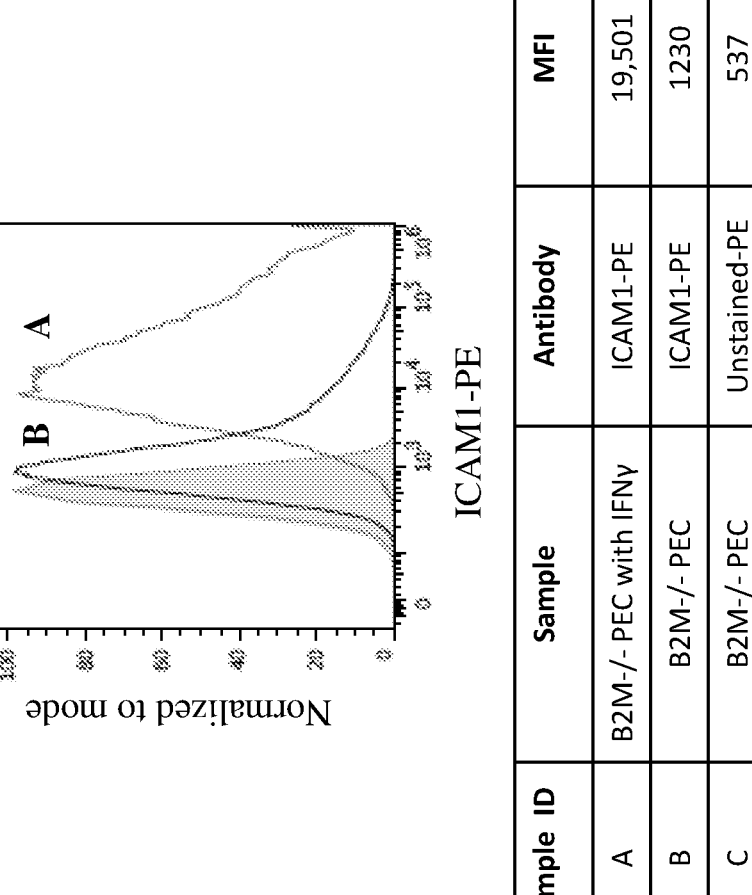
FIG. 7B shows representative flow cytometry analysis of ICAM-1 cell surface protein expression on B2M knockout PEC without IFN-γ (Line B) and after exposure to IFN-γ (Line A). After exposure to IFN-γ, the B2M−/− PEC have similar ICAM-1 cell surface protein expression as WT PEC which is greater than that of the background (shaded region).

FIG. 7B shows ICAM-1 cell surface protein expression in B2M knockout PEC. ICAM-1 cell surface protein expression in the B2M knockout PEC was similar to WT PEC, with and without IFN-γ exposure, with a minor reduction in florescence. Thus, treatment of B2M knockout PEC with IFN-γ increases ICAM-1 cell surface protein expression.

Figure 8:
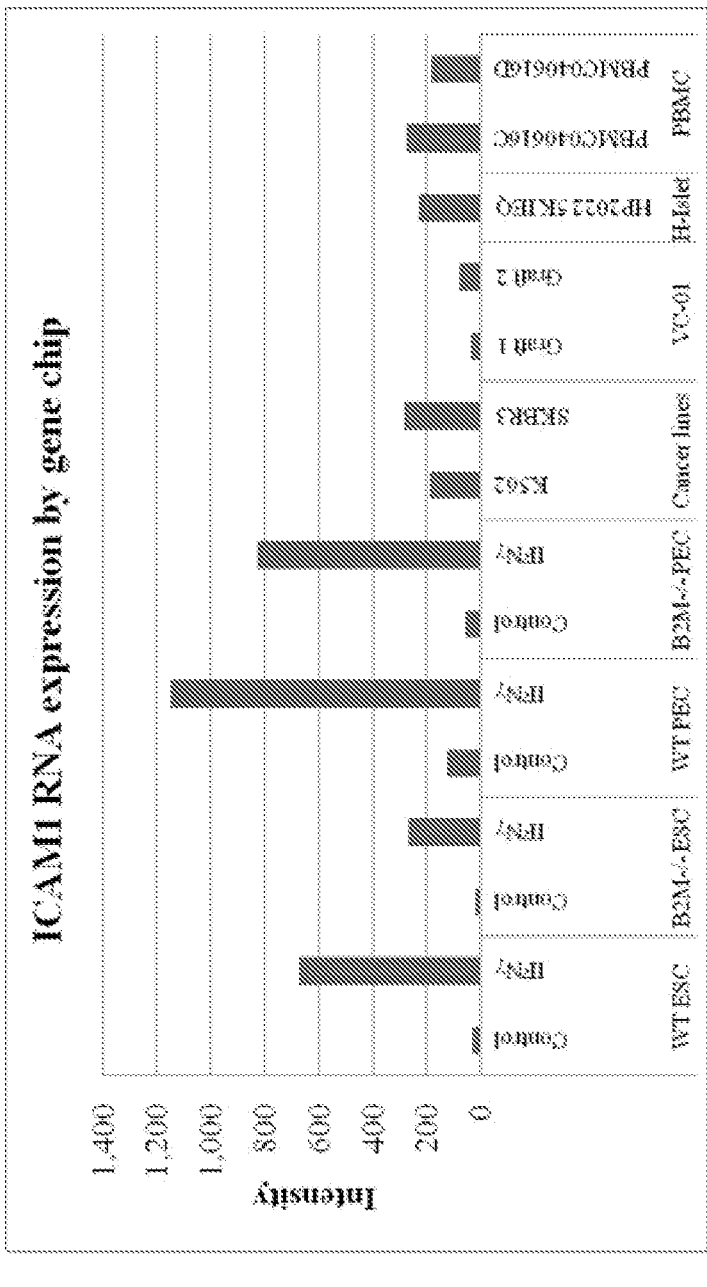
FIG. 8 is a bar graph showing mRNA expression data (Affymetrix expression array) for ICAM-1 in WT hES cells, B2M (−/−) hES cells, WT PEC, and B2M (−/−)PEC each not exposed to IFN-γ (control) or exposed to IFN-γ. ICAM-1 expression is also assessed in cells known to have low ICAM cell surface protein expression: cancer cells (K562 and SKBR3), transplanted PEC that was allowed to mature to insulin producing cells in vivo, human islet cells and two different samples of peripheral blood mononuclear cells (PBMC) (no exposure to IFN-γ). ICAM-1 mRNA expression is increased after exposure of hES cells (WT or B2M−/−) or PEC (WT or B2M−/−) to IFN-γ.

FIG. 8 shows RNA expression array data (Affymetrix), demonstrating that at the mRNA level, exposure to IFN-γ increases ICAM-1 expression in WThESC, B2M−/− hESC, WT PEC and B2M−/− PEC. Applicants discovered that cell surface protein expression of NK activating ligand ICAM-1 increased in the differentiated cell types (WT PEC and B2M−/− PEC) after exposure to IFN-γ Thus, ICAM-1 is highly inducible by IFN-γ stimulation in PEC.

Example 8: Effect of IFN-Gamma Treatment on Additional NK Activating Ligands

To further characterize the effect of IFN-γ treatment on target cells, WT PEC was assessed by flow cytometry under two conditions (1) untreated (Line B) and (2) treated with 100 ng/mL of IFN-γ for 18-24 hours (Line A) and cell surface protein expression of other known NK activating ligands were analyzed.

Figure 9:
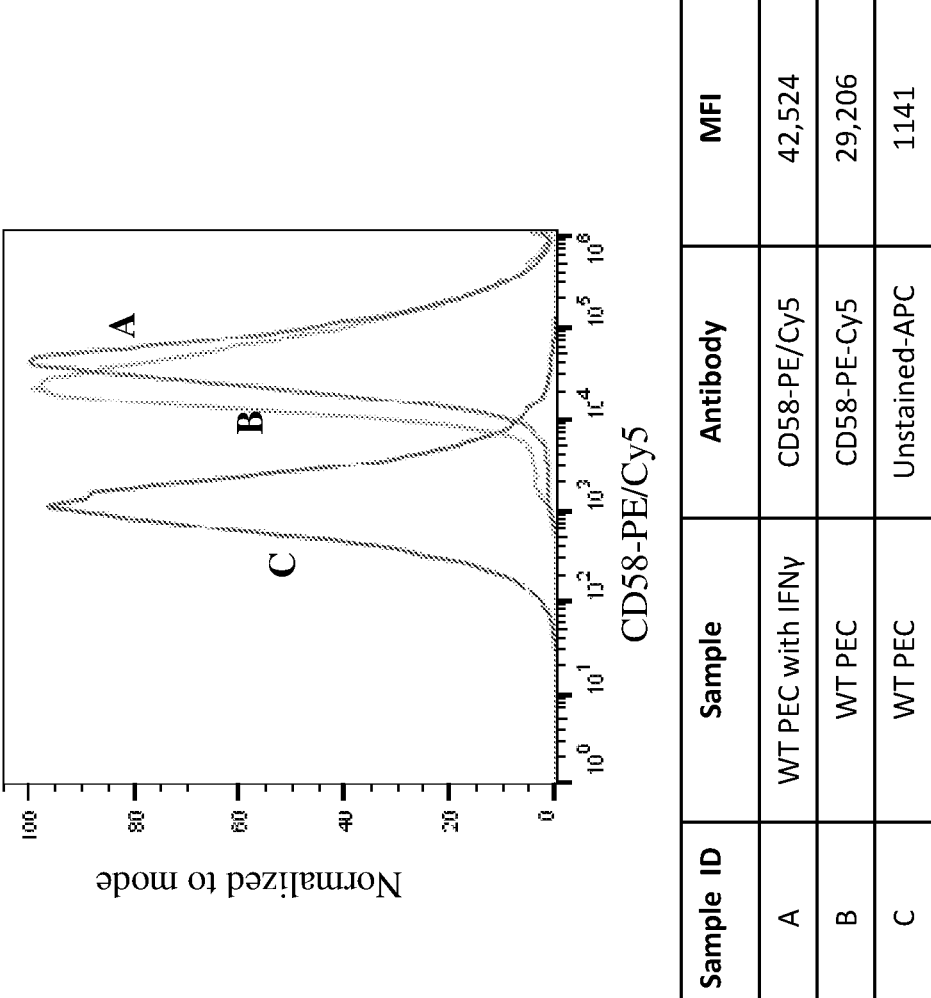
FIG. 9 shows representative flow cytometry analysis of CD58 (alias: LFA-3) cell surface protein expression on WT PEC without exposure to IFN-γ (Line B) and after exposure to IFN-γ (Line A). Line C is background expression with no antibody staining. Exposure to IFN-γ only slightly increases CD58 cell surface protein expression in WT PEC compared to untreated control. Antibody from BioLegend, Cat #330909.

FIG. 9 shows CD58 (also known as LFA-3) cell surface protein expression using an antibody from BioLegend, cat #330909 in WT PEC untreated (Line B) and following treatment of with IFN-γ (Line A). The large shift (increase) in florescent intensity compared to the background (Line C) in the untreated WT hES cells (Line B) indicates that most of the cells express CD58 protein on the surface. There was a small additional shift (increase) in florescent intensity following exposure to IFN-γ.

Figure 10:
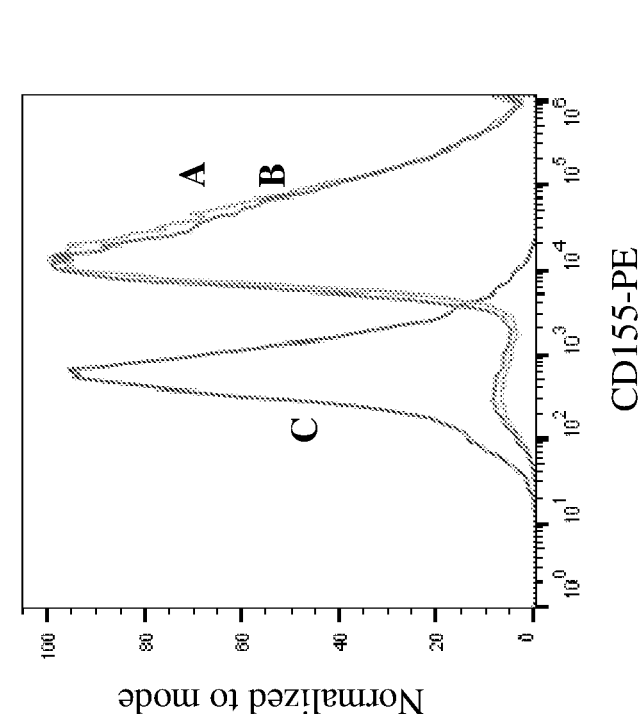
FIG. 10 shows representative flow cytometry analysis of CD155 cell surface protein expression on WT PEC without exposure to IFN-γ (Line B) and after exposure to IFN-γ (Line A). Line C is background expression with no antibody staining. After exposure to IFN-γ, the WT PEC have similar CD155 cell surface protein expression as WT untreated PEC control. Gene symbol PVR (aliases: CD155, NECL-5, HVED). Antibody from Milteneyi Biotech Inc., Cat. #130-105-905.

FIG. 10 shows CD155 (also known as PVR, NECL-5, HVED) cell surface protein expression using an antibody from Milteneyi Biotech Inc., cat #130-105-905in WT PEC untreated (Line B) and following treatment with IFN-γ (Line A). The shift (increase) in florescent intensity compared to the background (Line C) in the untreated WT PEC (Line B) indicates that WT PEC express CD155. There was not an additional increase (increase) in florescent intensity beyond untreated condition, following exposure to IFN-γ suggesting that CD155 expression does not increase in WT PEC following exposure to IFN-γ.

Figure 11:
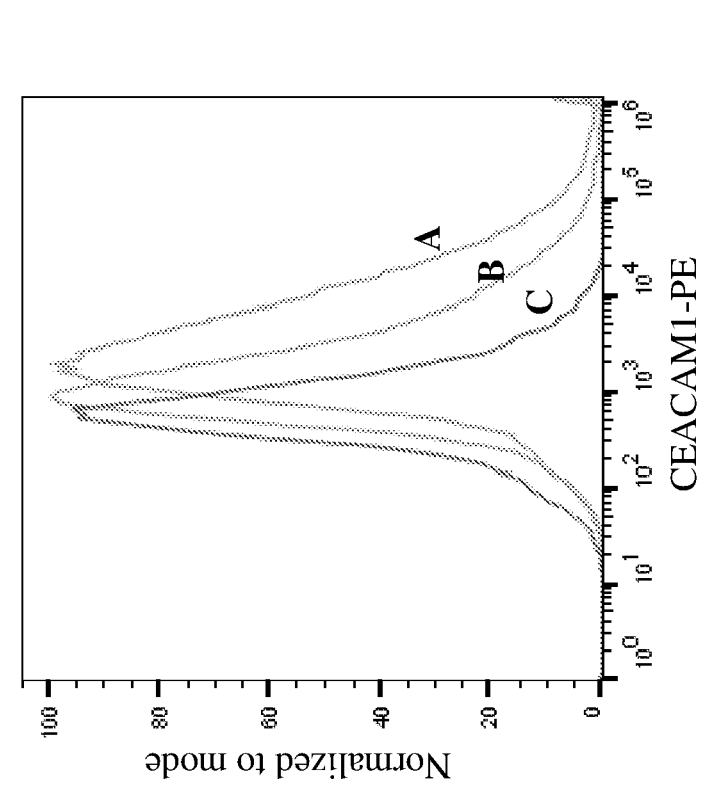
FIG. 11 shows representative flow cytometry analysis of CEACAMI (aliases: CD66a, BGP, BGP1) cell surface protein expression on WT PEC without exposure to IFN-γ (Line B) and after exposure to IFN-γ (Line A). Line C is background expression with no antibody staining. Exposure to IFN-γ slightly increases CEACAMI cell surface protein expression in WT PEC compared to untreated control. Antibody from Milteneyi Biotech Inc., Cat. #130-098-858.

FIG. 11 shows CEACAM1 (also known as CD66a, BGP, and BGP1) cell surface protein expression using an antibody from Milteneyi Biotech Inc., cat #130-098-858 in WT PEC untreated (Line B) and following treatment of with IFN-γ (Line A). The shift (increase) in florescent intensity compared to the background (Line C) in the untreated WT PEC (Line B) indicates that WT PEC express CEACAM1 protein on the cell surface. The shift (increase) in florescent intensity beyond untreated condition following exposure of WT PEC to IFN-γ suggests that CEACAM1 protein expression on cell surface increases in WT PEC following exposure to IFN-γ.

Figure 12:
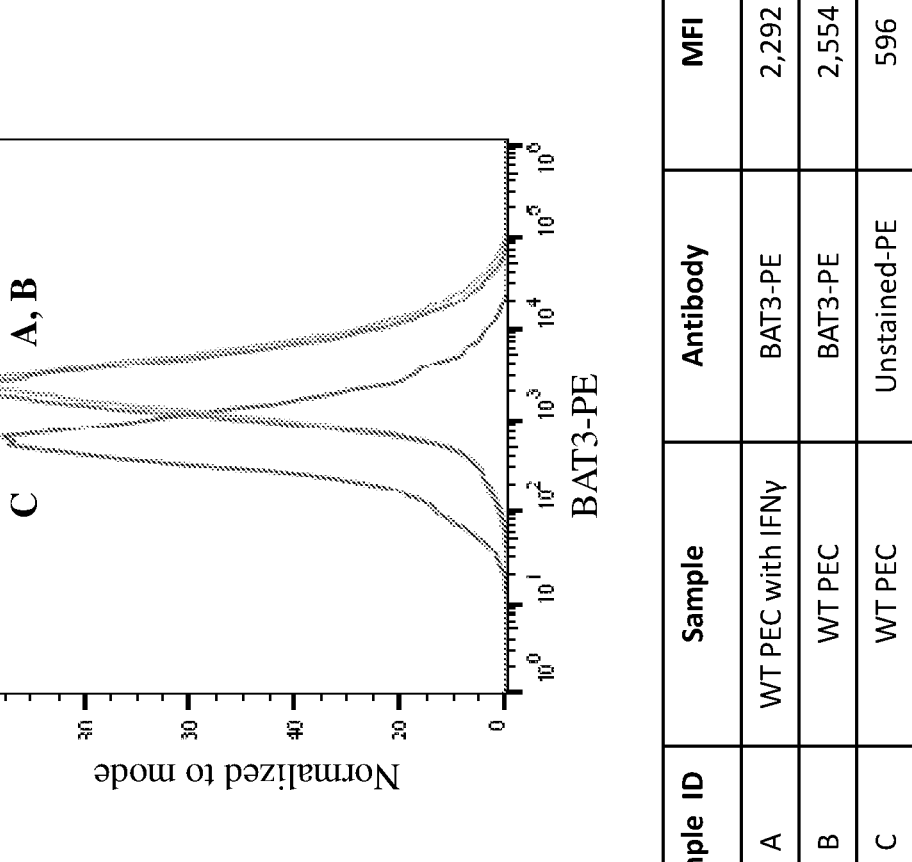
FIG. 12 shows representative flow cytometry analysis of BAT3 cell surface protein expression on WT PEC without exposure to IFN-γ (Line B) and after exposure to IFN-γ (Line A). Line C is background expression with no antibody staining. WT PEC in untreated control have similar BAT3 cell surface protein expression as WT PEC exposed to IFN-γ. Gene symbol BAG6 (aliases: BAT3, HLA-B-associated transcript 3). Antibody from Abcam, Inc., Cat. #ab210838.

FIG. 12 shows BAT3 (also known as BAG6) cell surface protein expression using an antibody from Abcam Inc., cat #ab210838 in WT PEC untreated (Line B) and following treatment with IFN-γ (Line A). The shift (increase) in florescent intensity compared to background (Line C) in the untreated PEC (Line B) suggests that the cells express CEACAM1. There was not an additional shift (increase) in florescent intensity beyond untreated condition following exposure of WT PEC to IFN-γ suggests that BAT3 expression does not increase in WT PEC following exposure to IFN-γ.

Figure 13:
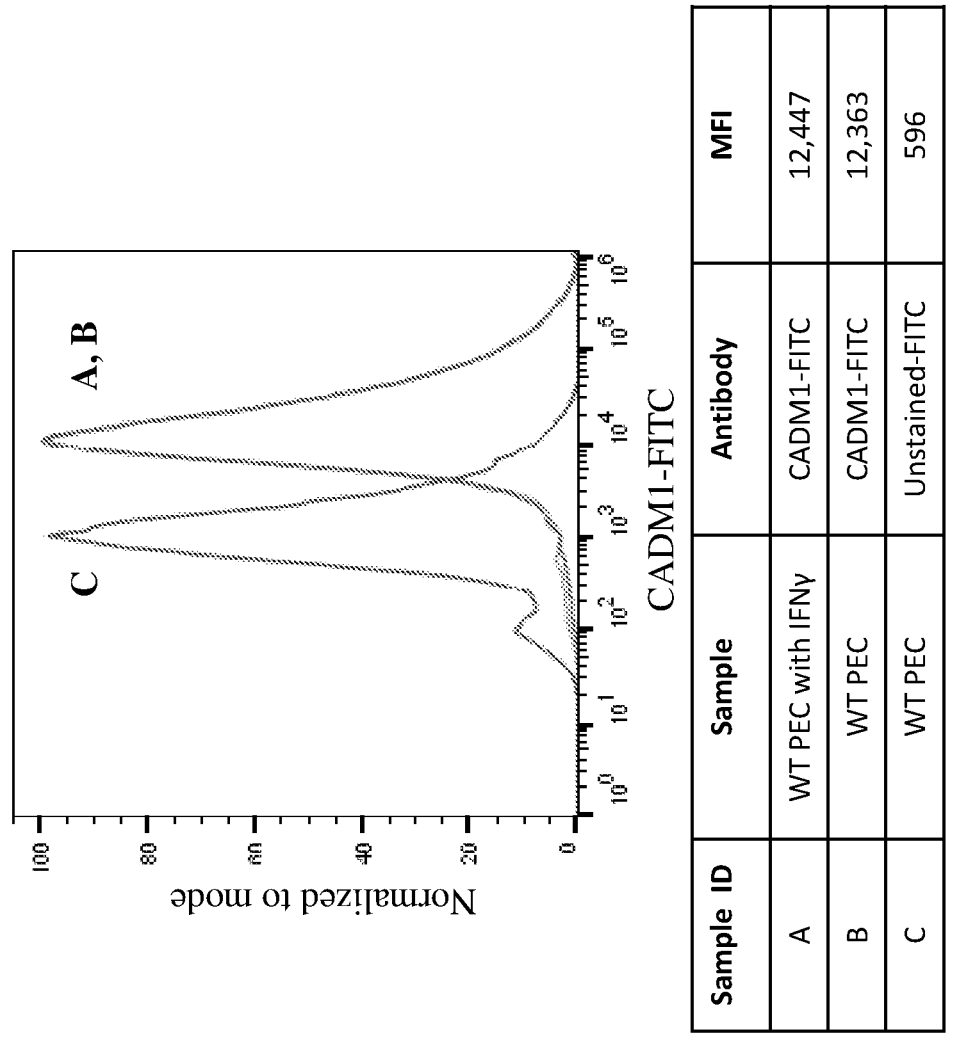
FIG. 13 shows representative flow cytometry analysis of CADMI (aliases: NECL2, TSLC1, IGSF4, RA175) cell surface protein expression on WT PEC without exposure to IFN-γ (Line B) and after exposure to IFN-γ (Line A). Line C is background expression with no antibody staining. After exposure to IFN-γ, WT PEC have similar CADMI cell surface protein expression as untreated control. Antibody from MBL International Corp. Cat. #CM004-4.

FIG. 13 shows CADM1 (also known as NECL2, TSLC1, IGSF4, RA175) cell surface protein expression using an antibody from MBL international Corporation, cat #CM004-4 in WT PEC untreated (Line B) and following treatment with IFN-γ (Line A). The shift (increase) in florescent intensity compared to background (Line C) in the untreated condition (Line B) suggests that WT PEC express CADM1 protein on cell surface. There was not an additional shift (increase) in florescent intensity beyond untreated condition following exposure of PEC to IFN-γ suggests that CADM1 expression does not increase following exposure to IFN-γ.

Figure 14:
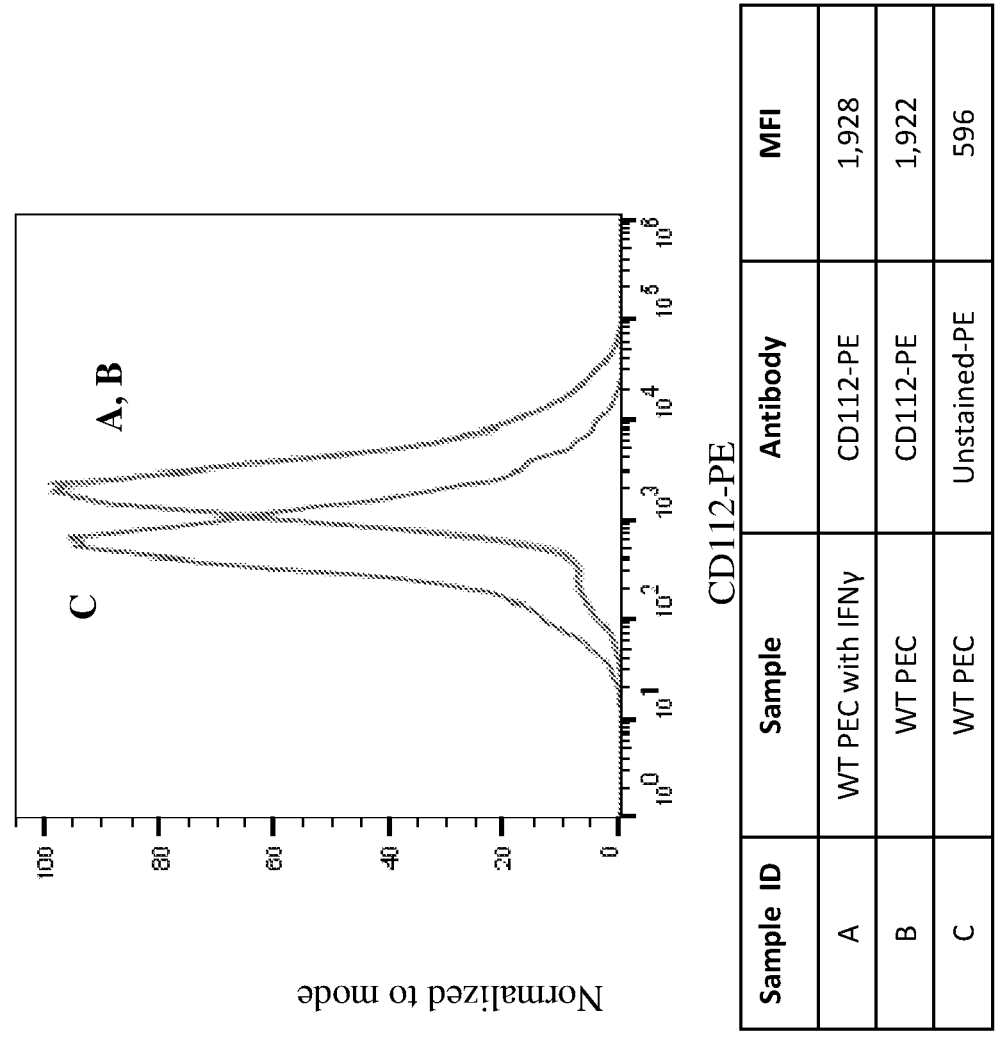
FIG. 14 shows representative flow cytometry analysis of CD112 cell surface protein expression on WT PEC without exposure to IFN-γ (Line B) and after exposure to IFN-γ (Line A). Line C is background expression with no antibody staining. After exposure to IFN-γ, the WT PEC have similar CD112 cell surface protein expression as untreated control. Gene symbol PVRL2 (aliases; CD112, Nectin-2, PVRR2, HVEB). Antibody from Milteneyi Biotech Inc., Cat. #130-109-056.

FIG. 14 shows CD112 (also known as Nectin-2, PVRR2, HVEB) expression using an antibody from Milteneyi Biotech Inc., cat #130-109-056 in WT PEC untreated (Line B) and following treatment with IFN-γ (Line A). The shift (increase) in florescent intensity compared to background (Line C) in the untreated condition (Line B), suggests that WT PEC express CD112 protein on cell surface. There was not an additional shift (increase) in florescent intensity beyond untreated condition, following exposure of PEC to IFN-γ suggesting that CD112 expression does not increase following exposure to IFN-γ.

Example 9: MHC-Class I Deficient, NK Cell-Activating Ligand Deficient Cells Prevent NK Cell Mediated Lysis To test whether the combination of reduced or eliminated HLA-Class I expression and reduced or eliminated NK cell-activating ligand expression is sufficient to prevent NK mediated cell lysis, ICAM-I expression was blocked on target cells using ICAM-1 blocking antibody at concentrations of 5 and 10 ug/mL. Addition of blocking ICAM-1 antibody to WT or B2M−/− ES cells or PEC caused reduction in NK lysis of target cells after IFN-γ treatment (FIG. 15).

Staining of Target Cells with Calcein-AM

Calcein release assay is a non-radioactive alternative for studying NK cell cytotoxicity. The target cells take up the fluorescent dye (calcein AM) and cytoplasmically convert it into the active fluorochrome, which is only released from the cell upon lysis. Lysed cells release the fluorochrome into the supernatant, which is then harvested and the amount of fluorescence quantitated in a fluorometer. The percent cell lysis is calculated from the amount of fluorescence present in the supernatant after incubation in the presence or absence of NK cells (effectors), blocking antibody or both.

Target cells comprised either WT ESC, B2M−/− ESC, WT PEC or B2M−/− PEC treated with or without 100 ng/ml of IFN-γ prior to labelling. To prepare the target cells, the target cell populations were stained with 2 ug/ml Calcein AM staining media (Enzo biosciences 1 mg/mL stock solution (cat #C3100MP)). The target cells were incubated for 1 hr at 37° C. in 8% CO2 incubator with intermittent mixing. The target cells were washed twice to remove any free Calcein AM, and resuspended at 1×105 cells/ml in RPMI complete media (RPMI, 10% heat inactivated FBS and 1% antibiotics).

Co-Culture Target, NK Cells and Blocking Antibody

Calcein AM labeled target cells were then incubated with NK cells (effector cells) with an effector-to-target ratio (E:T ratio) of 10:1. Specifically, 100 uL of NK cells at a density of 1×106 cells/mL were added per well in a 96 well V bottom plate and then 100 μL of Calcein stained ESC or PEC cells were added (1×105 cells/well). Where indicated, blocking antibody to human ICAM-1 surface antigen (R&D Systems, Inc., cat #BBA3) at concentration of 5 and 10 ug/mL was added to the wells to determine if NK-mediated cell lysis could be reduced.

Plates were incubated for 4 hours at 37° C. in a 8% CO2 incubator. After the incubation period, plates were centrifuged at 200×g for 2 minutes. 100 uL of supernatant was removed carefully and transferred to a black pigmented 96 well plate and fluorescence measured using a Molecular Device plate reader (excitation filter: 485 nm/emission filter: 530 nm). Specific lysis was calculated by using the formula, % lysis=100×[(mean fluorescence with antibody-mean spontaneous fluorescence)/(mean maximum fluorescence-mean spontaneous fluorescence)]. Maximum fluorescence was determined by the lysis of cells incubated with detergent (1% Triton X-100) and spontaneous lysis was the fluorescence obtained with target cells without any antibody or effector cells.

Results

As shown in FIG. 1, the goal is to move from scenario C (NK cells attack target cells) to scenario A (no response or reduced response). In FIG. 15, this scenario is shown in conditions 4 and 8. In conditions 4 and 8 the target cells (B2M–/– hES cells or PEC) lack functional HLA-Class I surface expression and are exposed to IFN-γ. As discussed above and seen in conditions 4 and 8 exposure to IFN-γ causes an increase in NK activating ligands (ICAM-1) which results in greater cell lysis compared to HLA-Class I knockouts without exposure to IFN-γ (compare first bars in condition 3 vs. 4 and condition 7 vs. 8). However, once treated with an ICAM-1 inhibitory antibody which serves to block expression of the NK activating signal on the target cell, NK mediated cell lysis falls from 83% to 73% in B2M–/– hES cells and 72% to 61% in B2M–/– PEC treated with IFN-γ. The percentage NK mediated cell lysis does not drop to zero because, ICAM-1 cell surface protein expression may not be completely blocked using the blocking antibody and as discussed above, the target cells express more than one NK activating ligand. The percentage of NK mediated cell lysis is expected to fall to a greater extent when ICAM-1 expression is inhibited further and other NK activating ligands are blocked in the target cells. Therefore, the ICAM-1 inhibitory antibody can be combined with additional NK activating ligand inhibitory antibodies including inhibitory antibodies to any of the ligands listed in Table 1 and preferably those in category 1 (Known activating ligands) and 2 (Potential candidates for activating ligands identified from gene chip data, those are upregulated in PEC and/or ESC after IFNγ). In one embodiment, the ICAM1 gene and other NK activating ligand genes are disrupted in order to completely block their activity.

Scenario D from FIG. 1 is presented in the first bars of conditions 2 and 6 of FIG. 15. In conditions 2 and 6, the WT hES cells and PEC have upregulated cell surface protein expression of both HLA-Class I antigens and NK activating ligands as a result of their exposure to IFN-γ. When the cells are incubated with the ICAM-1 inhibitory antibody, this represents a situation of moving from Scenario D towards Scenario B of FIG. 1. Upon incubation with ICAM1 inhibitory antibody, cell death decreases: 79% to 60% in WT hES cells and 53% to 27% in WT PEC exposed to IFN-γ. Indeed, when WT PEC is exposed to IFN-γ and incubated with the ICAM-1 inhibitory antibody, NK cell lysis falls below that of untreated WT PEC: 27% for WT PEC, IFN-γ and ICAM-1 inhibitory antibody compared to 37% WT PEC, ICAM-1 inhibitory antibody with no IFN-γ.

Scenario B from FIG. 1 is exemplified by the ICAM1 antibody treated bars in conditions 1, 2, 5 and 6 in FIG. 15. There, the target hES cells and PEC have HLA-Class I and NK activating ligands, but when the target cells are not exposed to IFN-γ, there is no increase in cell surface protein expression of ICAM-1. As a result, the ICAM-1 inhibitory antibody has less of an effect. Hence, cell lysis remains about the same: 58% to 57% in hES cells and 33% to 37% in PEC cells.

Scenario C from FIG. 1 is similar to the first bars in conditions 3, 4, 7 and 8 in FIG. 15. In these conditions, the cells have no HLA-Class I cell surface expression as a result of B2M–/–. Therefore, when NK activating ligands are not activated by IFN-γ exposure of the cells to the ICAM-1 inhibitory antibody has little effect. 71% to 70% in hES cells and 54% to 57% in PEC.

As a general observation, NK mediated cell lysis is less in differentiated cell populations (WT PEC and B2M–/– PEC) compared to undifferentiated cell populations (WT hES and B2M–/– hES). NK mediated cell lysis increases to a greater extent when cells (WT or B2M–/– knockout, hES or PEC) are activated with IFN-γ.

Example 10: Generation of NK Activating Ligand Deficient B2M–/– Knockout HES Cells Example 9 describes that inhibiting or quenching ICAM-1 expression protects the IFN-γ treated B2M–/– PEC from NK mediated cell killing activity. Hence, to protect B2M–/– PEC from NK cell mediated killing post-transplant, it will be desirable to disrupt NK cell activating ligand genes. For example, based on the examples above, ICAM-1, a known NK activating ligand gene can be disrupted or 'knocked out'. Preferably, both alleles of the ICAM-1 locus in the B2M–/– CyT49 hESC line can be disrupted using CRISPR/Cas9 or any other gene editing technology now known or in the future should be known See PCT Publication No. WO2016183041A, which is incorporated herein by reference in its entirety. Examples of published sequences for ICAM-1 are submitted as SEQ ID NOS.: 4, 5, and 6. For example, in one embodiment of the invention, NEXTGEN™ CRISPR (Transposagen Inc., Lexington Kentucky), which incorporates dual guide RNA's and a catalytically inactive Cas9 protein fused to the FokI nuclease, is used to gene edit the cells.

Plasmids containing the guide RNAs and Cas9 can be electroporated into B2M–/– CyT49 hESC, and seeded onto tissue culture plates. Post-electroporation, cells can be sorted for negative reactivity to an ICAM-1 antibody by flow cytometry. Sorted cells can be plated at clonal density. Individual clones can be picked and re-plated. Clones can be expanded and cryopreserved. Expanded clones that showed a normal karyotype by G-banding, and are negative for expression of ICAM-1 protein and for surface expression of ICAM-1 proteins by flow cytometry and/or immunofluorescence can be chosen for further experimentation.

As described above, cells deficient for ICAM1 and B2M cannot express at least one NK activating ligand and at least one or all MHC-Class I protein on their cell surface and therefore should not bind to NK cell activating receptors and are protected from NK mediated cell death.

Example 11: Generation of Multiple NK Activating Ligand Deficient B2M–/– Knockout HES Cells Example 9 and 10 demonstrate that inhibiting functional cell surface expression (anti-NK activating ligand) and gene disruption of NK cell activating ligand (e.g., ICAM1–/–) in combination with a disruption of MHC-Class I cell surface expression (e.g., B2M–/–) can provide target cells protection from NK mediated cell death. Transplantation of a cell deficient in more than one NK cell activating ligand can be produced and confer further protection from NK mediated cell death.

The CD58 gene is selected as the NK activating ligand gene to knockout. Both alleles of the CD58 locus can be disrupted using CRISPR/Cas9 technology, using known techniques as outlined in WO2016183041A, in the B2M–/–: ICAM–/– double knockout CyT49 hESC line. Examples of published sequences for CEACAM1 are submitted as SEQ ID NOS .: 7, 8, and 9. Again, the version of editing can be NEXTGEN™ CRISPR (Transposagen Inc., Lexington Kentucky).

Plasmids containing the guide RNAs and Cas9 can be electroporated into B2M–/–, ICAM–/– knockout CyT49 hESC, and seeded onto tissue culture plates. Post-electroporation, cells can be sorted for negative reactivity to a CD58 antibody by flow cytometry. Sorted cells can be plated at clonal density. Individual clones can be picked and re-plated. Clones can be expanded and cryopreserved. Expanded clones that showed a normal karyotype by G-banding, and are negative for expression of CD58 protein and for surface expression of CD58 proteins by flow cytometry and/or immunofluorescence can be chosen for further experimentation.

As described above, cells with disrupted, deleted or modified ICAM1. CD58 and B2M cannot express ICAM1. CD58 nor MHC Class I proteins on their cell surface and therefore should not bind to NK cell activating receptors and are protected from NK mediated cell death.

The invention claimed is:

1. A method of producing insulin in a human subject with type I diabetes, comprising:

transplanting a cell encapsulation device comprising pancreatic endoderm cells (PEC) that are CHGA⁻, NKX6.1⁺, PDX1⁺ into a location in the human subject, wherein the function of at least one major histocompatibility complex (MHC)-Class I gene and at least one natural killer (NK) cell activating ligand is disrupted or inhibited in the PEC, resulting in reduced binding of the NK activating ligand to a NK activating receptor in PEC, and wherein the PEC mature in the human subject to produce insulin in response to glucose stimulation.

2. The method of claim 1, wherein the location is subcutaneous in the human subject.

3. The method of claim 1, wherein the cell encapsulation device is perforated.

4. The method of claim 1, wherein the PEC further express a protein which when expressed in the presence of a cell death inducing agent, the cell death inducing agent is capable of killing cells in the cell encapsulation device.

5. The method of claim 4, wherein the protein is herpes simplex virus thymidine kinase and the cell death inducing agent is ganciclovir.

6. The method of claim 1, wherein the MHC-Class I gene codes for beta-2 microglobulin (B2M).

7. The method of claim 1, wherein the NK cell activating ligand is Intercellular Adhesion Molecule 1 (ICAM1), CD58, CD155, Carcinoembryonic Antigen-Related Cell Adhesion Molecule 1 (CEACAM1), Cell Adhesion Molecule 1 (CADM1), MHC-Class I Polypeptide-Related Sequence A (MICA), MHC-Class I Polypeptide-Related Sequence B (MICB), or a combination thereof.

8. The method of claim 1, wherein the NK cell activating ligand is ICAM1 and CD58.

9. The method of claim 1, wherein the NK cell activating ligand is ICAM1, CD58, CD155, CEACAM1, CADM1, MICA and MICB.

10. The method of claim 1, wherein the NK cell activating ligand is ICAM-1, CD58, and CD155.

11. The method of claim 1, wherein the NK cell activating ligand is ICAM1, CD58, CD155, and CADM1.

12. The method of claim 1, wherein the NK cell activating ligand is CD58 and CADM1.

13. The method of claim 1, wherein the NK cell activating ligand is ICAM-1, CADM1, and CD155.

* * * * *

SEQUENCE LISTING

```
Sequence total quantity: 9
SEQ ID NO: 1              moltype = DNA  length = 23
FEATURE                   Location/Qualifiers
source                    1..23
                          mol_type = genomic DNA
                          organism = Homo sapiens
SEQUENCE: 1
cgcgagcaca gctaaggcca cgg                                          23

SEQ ID NO: 2              moltype = DNA  length = 23
FEATURE                   Location/Qualifiers
source                    1..23
                          mol_type = genomic DNA
                          organism = Homo sapiens
SEQUENCE: 2
cagtaagtca acttcaatgt cgg                                          23

SEQ ID NO: 3              moltype = DNA  length = 23
FEATURE                   Location/Qualifiers
source                    1..23
                          mol_type = genomic DNA
                          organism = Homo sapiens
SEQUENCE: 3
gagtagcgcg agcacagcta agg                                          23

SEQ ID NO: 4              moltype = DNA  length = 23
FEATURE                   Location/Qualifiers
source                    1..23
                          mol_type = genomic DNA
                          organism = Homo sapiens
SEQUENCE: 4
cctcaaaagt catcctgccc cgg                                          23

SEQ ID NO: 5              moltype = DNA  length = 23
FEATURE                   Location/Qualifiers
source                    1..23
                          mol_type = genomic DNA
                          organism = Homo sapiens
SEQUENCE: 5
agcaactcct ttttaggcaa cgg                                          23

SEQ ID NO: 6              moltype = DNA  length = 23
FEATURE                   Location/Qualifiers
source                    1..23
```

```
                              mol_type = genomic DNA
                              organism = Homo sapiens
SEQUENCE: 6
ccgcactcct ggtcctgctc ggg                                                  23

SEQ ID NO: 7          moltype = DNA  length = 23
FEATURE               Location/Qualifiers
source                1..23
                      mol_type = genomic DNA
                      organism = Homo sapiens
SEQUENCE: 7
gagtgcgtgt accctggcag ggg                                                  23

SEQ ID NO: 8          moltype = DNA  length = 23
FEATURE               Location/Qualifiers
source                1..23
                      mol_type = genomic DNA
                      organism = Homo sapiens
SEQUENCE: 8
ggtacacgca ctctgtgaag tgg                                                  23

SEQ ID NO: 9          moltype = DNA  length = 23
FEATURE               Location/Qualifiers
source                1..23
                      mol_type = genomic DNA
                      organism = Homo sapiens
SEQUENCE: 9
tacacgcact ctgtgaagtg ggg                                                  23
```